United States Patent
Wu et al.

(10) Patent No.: US 12,030,957 B2
(45) Date of Patent: Jul. 9, 2024

(54) PLAP-CAR-EFFECTOR CELLS

(71) Applicants: ProMab Biotechnologies, Inc., Richmond, CA (US); Forevertek Biotechnology Co., Ltd, Hunan (CN)

(72) Inventors: Lijun Wu, Albany, CA (US); Vita Golubovskaya, Richmond, CA (US)

(73) Assignees: ProMab Biotechnologies, Inc., Richmond, CA (US); Forevertek Biotechnology Co., Ltd, Changsha (CN)

( * ) Notice: Subject to any disclaimer, the term of this patent is extended or adjusted under 35 U.S.C. 154(b) by 796 days.

(21) Appl. No.: 17/115,591

(22) Filed: Dec. 8, 2020

(65) Prior Publication Data

US 2021/0107996 A1 Apr. 15, 2021

Related U.S. Application Data

(63) Continuation of application No. PCT/US2019/033953, filed on May 24, 2019.
(Continued)

(51) Int. Cl.
*C07K 14/725* (2006.01)
*A61K 35/17* (2015.01)
(Continued)

(52) U.S. Cl.
CPC .............. *C07K 16/40* (2013.01); *A61K 35/17* (2013.01); *A61P 35/00* (2018.01);
(Continued)

(58) Field of Classification Search
CPC ... A61K 35/17; A61K 2039/505; A61P 35/00; C07K 14/7051; C07K 16/2803;
(Continued)

(56) References Cited

U.S. PATENT DOCUMENTS

2015/0307623 A1 10/2015 Abbot et al.
2017/0281766 A1* 10/2017 Wiltzius ........... C07K 14/70575
(Continued)

FOREIGN PATENT DOCUMENTS

EP 0429242 B1 6/1995
WO WO1991007500 * 5/1991
(Continued)

OTHER PUBLICATIONS

Beth Kenkel, Antibodies 101: Single Chain Fragment Variables (scFvs), Addgene Blog, Jun. 3, 2021 (Year: 2021).*
(Continued)

*Primary Examiner* — Louise W Humphrey
*Assistant Examiner* — Mary A Crum
(74) *Attorney, Agent, or Firm* — Perkins Coie LLP; Viola Kung

(57) ABSTRACT

The present invention is directed to a chimeric antigen receptor (CAR) fusion protein comprising from N-terminus to C-terminus: (i) a single-chain variable fragment (scFv) comprising $V_H$ and $V_L$, wherein scFv binds to human PLAP (placental alkaline phosphatase), (ii) a transmembrane domain, (iii) a co-stimulatory domain of CD28, OX-40, GITR, or 4-1BB, and (iv) CD3 an activating domain. The present invention is also directed to T cells, natural killer (NK) cells, or macrophages, modified to express the CAR of the present invention. The present invention is further directed to a method for treating PLAP-positive cancer cells by administering PLAP-CAR-T cells, PLAP-CAR-NK cells, or PLAP-CAR-macrophages to the patients.

7 Claims, 22 Drawing Sheets

Specification includes a Sequence Listing.

Related U.S. Application Data

(60) Provisional application No. 62/792,344, filed on Jan. 14, 2019, provisional application No. 62/683,999, filed on Jun. 12, 2018.

(51) Int. Cl.
*A61P 35/00* (2006.01)
*C07K 14/705* (2006.01)
*C07K 16/28* (2006.01)
*C07K 16/40* (2006.01)
*A61K 39/00* (2006.01)

(52) U.S. Cl.
CPC .... *C07K 14/7051* (2013.01); *C07K 14/70517* (2013.01); *C07K 14/70521* (2013.01); *C07K 16/2803* (2013.01); *C07K 16/2818* (2013.01); *C07K 16/2827* (2013.01); *A61K 2039/505* (2013.01); *A61K 2039/5156* (2013.01); *A61K 2039/5158* (2013.01); *C07K 2317/24* (2013.01); *C07K 2317/567* (2013.01); *C07K 2317/622* (2013.01); *C07K 2317/76* (2013.01); *C07K 2319/02* (2013.01); *C07K 2319/03* (2013.01); *C07K 2319/30* (2013.01); *C07K 2319/33* (2013.01)

(58) Field of Classification Search
CPC ............ C07K 16/2818; C07K 2317/24; C07K 2317/622; C07K 2317/76
See application file for complete search history.

(56) References Cited

U.S. PATENT DOCUMENTS

| | | |
|---|---|---|
| 2018/0021378 A1 | 1/2018 | Kang et al. |
| 2018/0273640 A1 | 9/2018 | Liang et al. |

FOREIGN PATENT DOCUMENTS

| | | | | |
|---|---|---|---|---|
| WO | WO-2017143094 A1 | * | 8/2017 | ............. A61K 35/17 |
| WO | 2018200713 A1 | | 11/2018 | |

OTHER PUBLICATIONS

Appendix A scFv alignment mouse h1-h5 (Year: 2023).*
GenBank ACR16187.1 Immunoglobulin heavy chain variable region partial *Homo sapiens*, published Apr. 2010 (Year: 2010).*
Appendix B VH aligment SEQ 21 MoVHPLAP (Year: 2023).*
Martineau, Pierre, Peter Jones, and Greg Winter. "Expression of an antibody fragment at high levels in the bacterial cytoplasm." Journal of molecular biology 280.1 (1998): 117-127 (Year: 1998).*
CAA12399.1 (GenBank CAA12399.1 anti-beta-galactosidase ScFv antibody, published Apr. 2010) (Year: 2002).*
Appendix C alignment SEQ23 MoVHPLAP HuVKPLAP modified CAA12399.1 (Year: 2023).*
Kulemzin, S. V., et al. "Modular lentiviral vector system for chimeric antigen receptor design optimization." Russian Journal of Bioorganic Chemistry 43 (2017): 107-114 (Year: 2017).*
Appendix D Alignment SEQ ID 20 (Year: 2023).*
Almagro et al. Humanization of Antibodies, Frontiers in Bioscience 13, 1619-1633, 2008 (Year: 2008).*
Janeway et al. Immunobiology: the Immune System in Health and Disease (2001), Elsevier Science Ltd/Garland Publishing, New York, NY, Fifth Edition (Year: 2001).*
Goel et al. "Plasticity within the Antigen Combining Site May Manifest as Molecular Mimicry in the Humoral Immune Response", The Journal of Immunology 173(12):7358-7367, 2004 (Year: 2004).*
Edwards et al. "The remarkable flexibility of the human antibody repertoire; isolation of over one thousand different antibodies to a single protein, BLyS" J. Mol. Biol. (2003) 334, 103-118, DOI: 10.1016/j.jmb.2003.09.054 (Year: 2003).*
Lloyd et al. Modelling the human immune response: performance of a 10e11 human antibody repertoire against a broad panel of therapeutically relevant antigens. Protein Engineering, Design and Selection, vol. 22, Issue 3, Mar. 1, 2009 (Year: 2009).*
Brown et al. "Tolerance of single, but not multiple, amino acid replacements in antibody VH CDR 2: a means of minimizing B cell wastage from somatic hypermutation?", J Immunol. May 1996;156(9):3285-91 (Year: 1996).*
Vajdos et al. "Comprehensive functional maps of the antigen-binding site of an anti-ErbB2 antibody obtained with shotgun scanning mutagenesis" J Mol Biol. Jul. 5, 2002;320(2):415-28 (Year: 2002).*
Early, Philip, et al. "An immunoglobulin heavy chain variable region gene is generated from three segments of DNA: VH, D and JH." Cell 19.4 (1980): 981-992 (Year: 1980).*
International Search Report for PCT Application No. PCT/US2019/033953, dated Sep. 3, 2019. 1 pages.
Kulemzin, S. et al. "Engineering Chimeric Antigen Receptors" ACTA Naturae, 2017, vol. 9, pp. 6-14.
Supplemental European Search Report for European Application No. 19820564, dated Feb. 3, 2022. 3 pages.
Smans, K. et al. "Tumor-cell Lysis by In-Situ-Activated Human Peripheral-Blood Mononuclear cells" International Journal of Cancer, 1991, vol. 47, pp. 431-438.
Smans, K. et al. "Bispecific Antibody-Mediated Lysis of Primary Cultures of Ovarian Carcinoma Cells Using Multiple Target Antigens" International Journal of Cancer, 1999, vol. 83, pp. 270-277.
Zhukovsky, E. et al. "Bispecific antibodies and CARs: generalized immunotherapeutics harnessing T cell redirection" Current Opinion in Immunology, 2016, vol. 40, pp. 24-35.
Extended European Search Report dated May 6, 2022 for European Application No. 19820654.3. 3 pages.

* cited by examiner

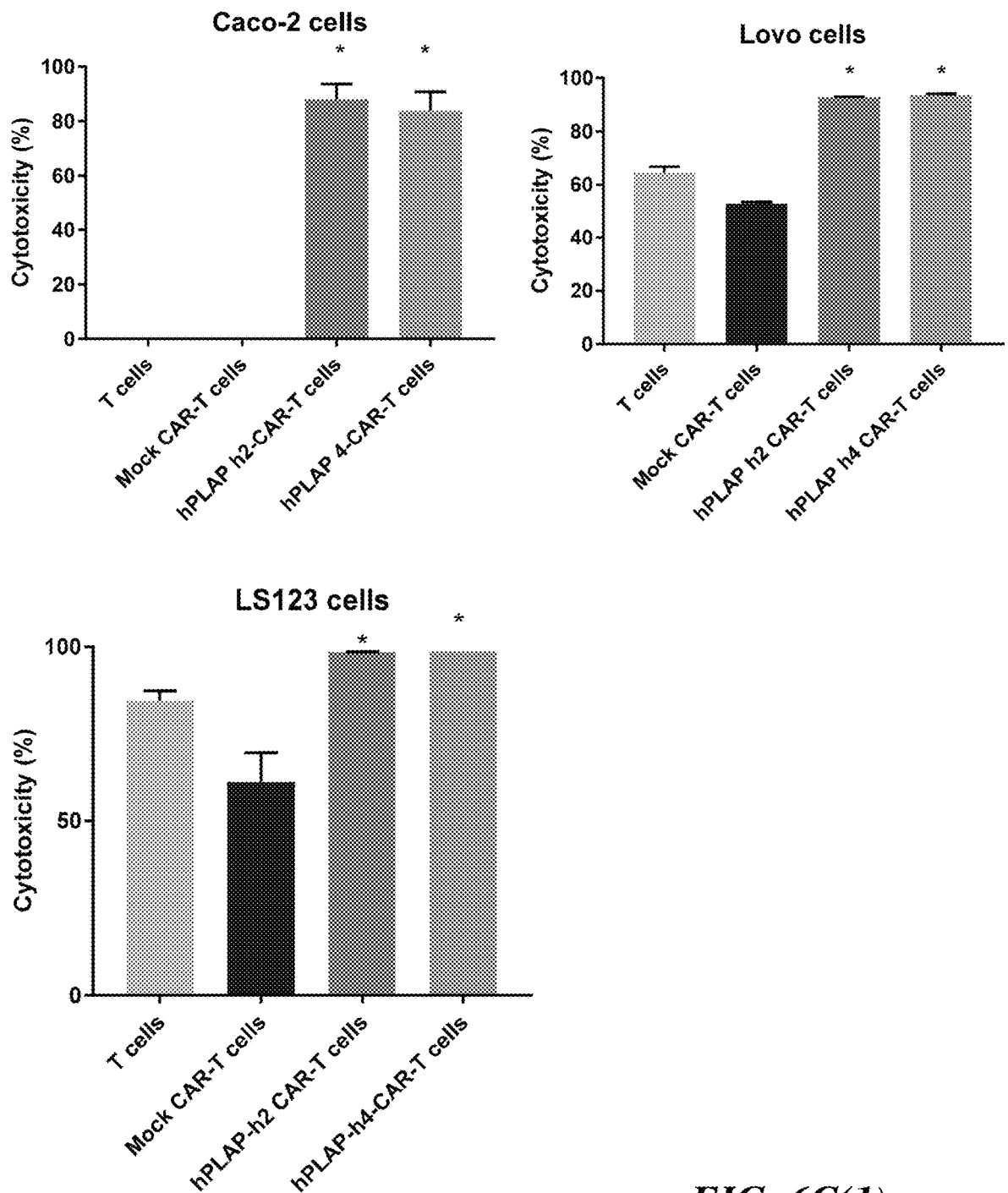
FIG. 6C(1)

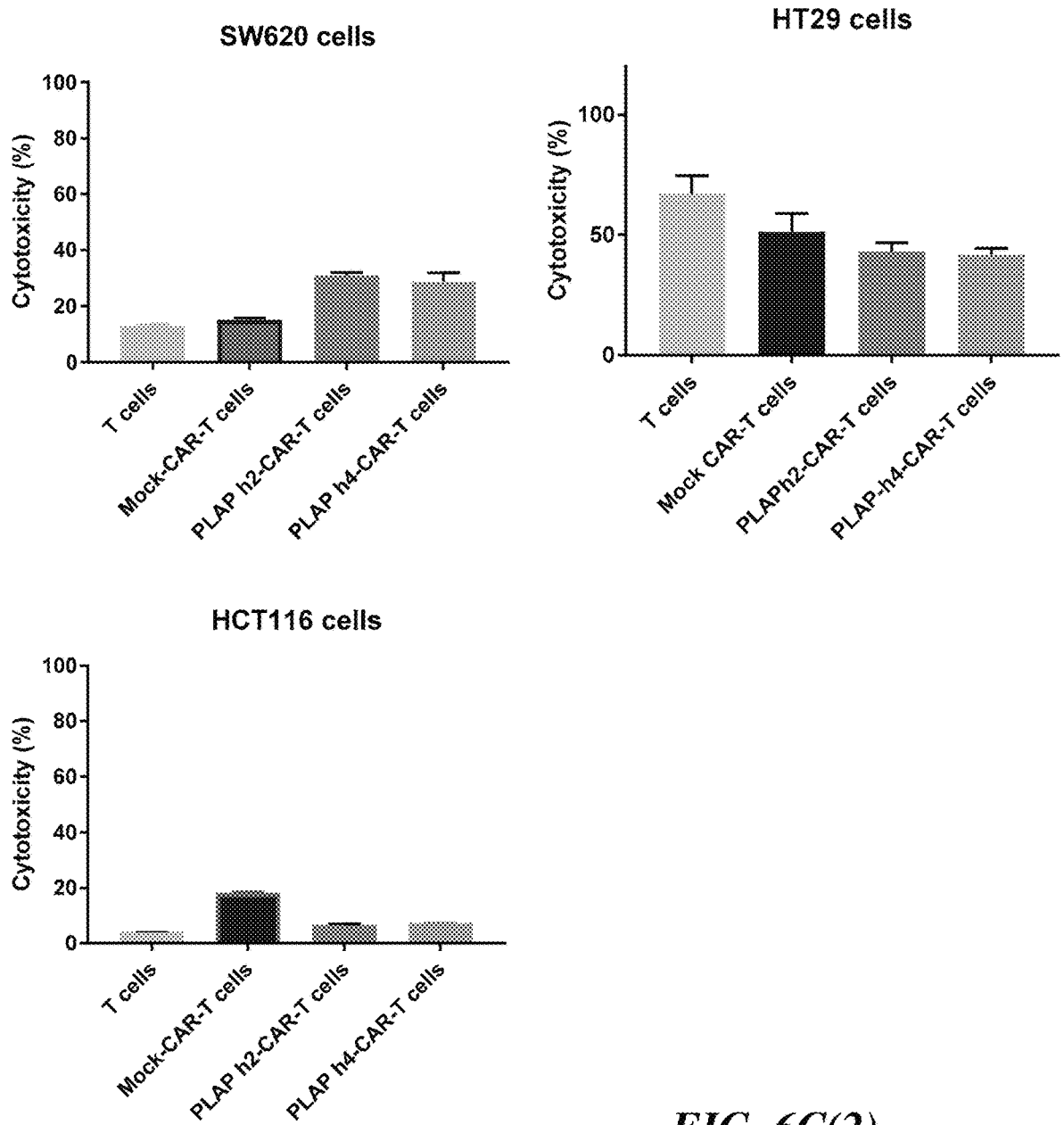
FIG. 6C(2)

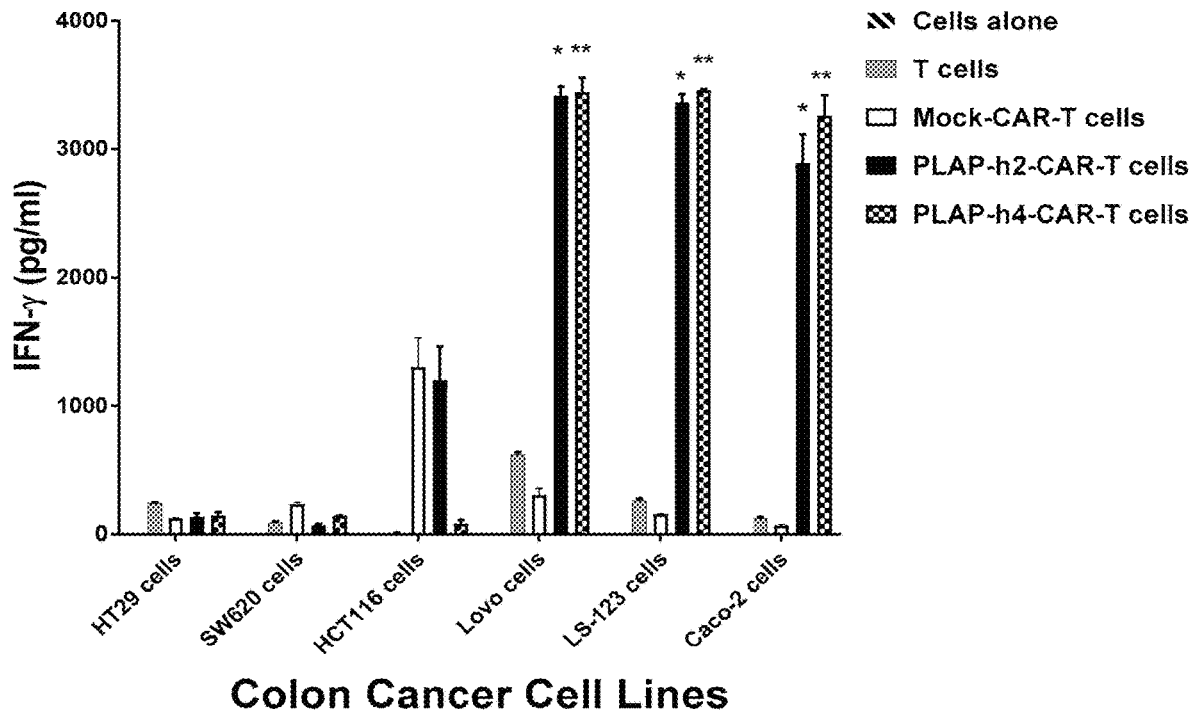
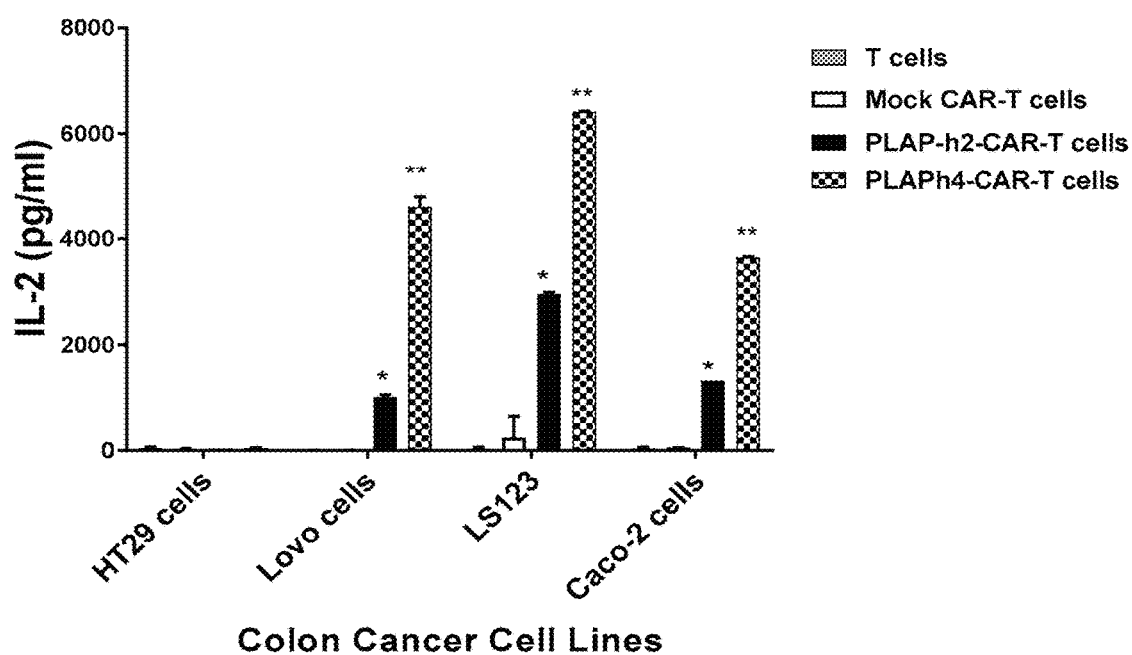
*FIG. 6D(1)*

*FIG. 6D(2)*

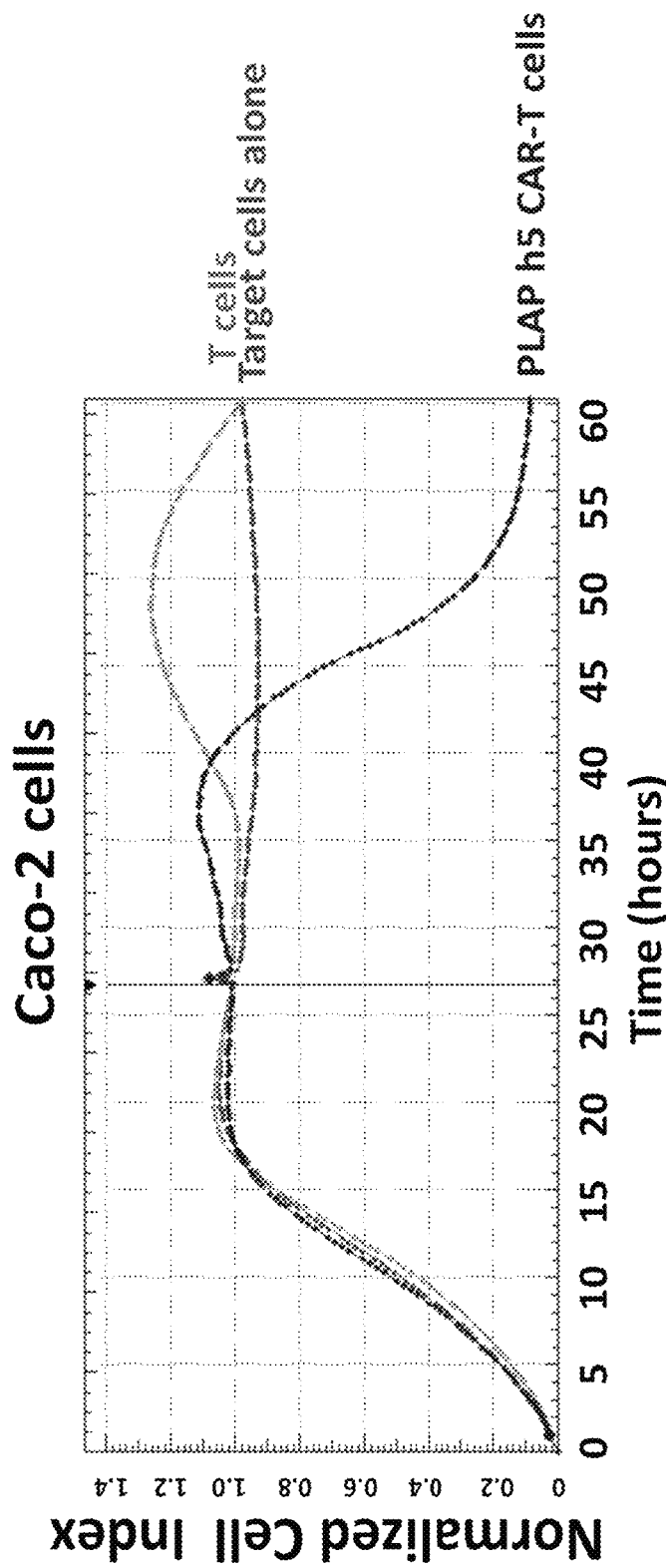
FIG. 8A(1)

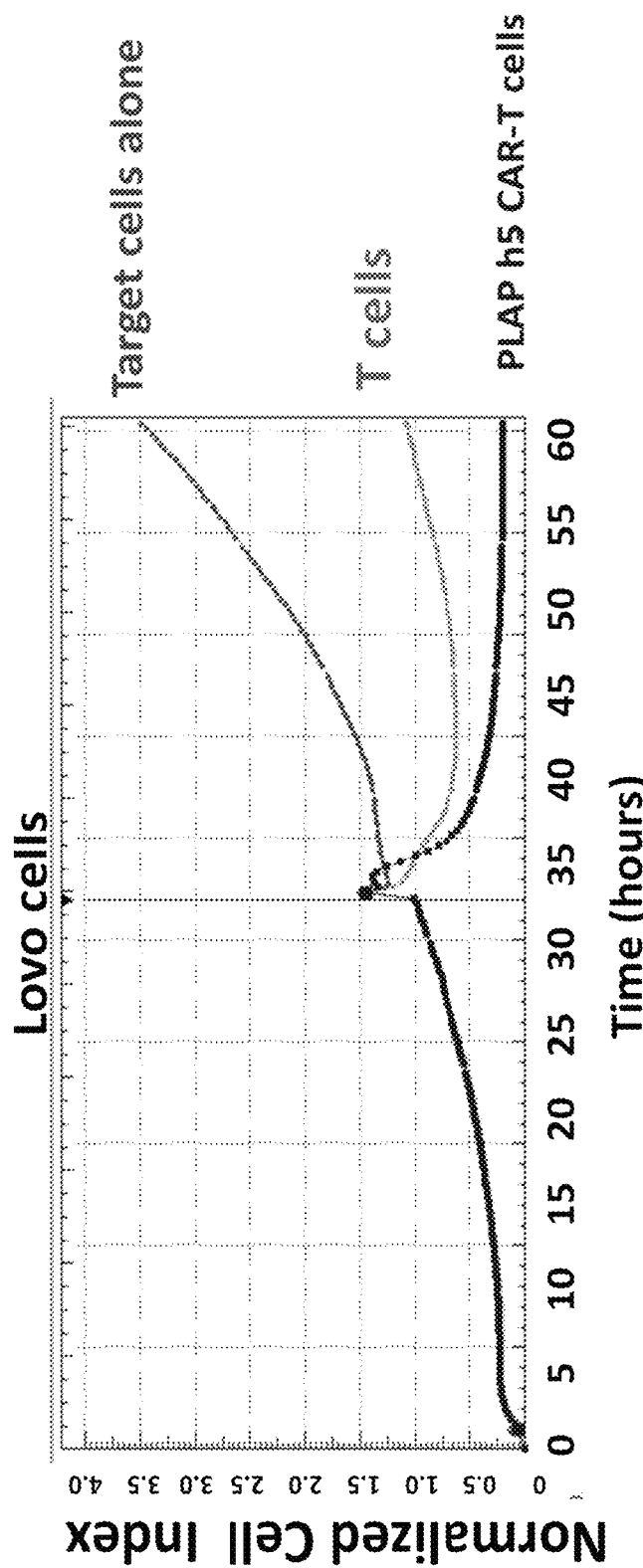
FIG. 8A(2)

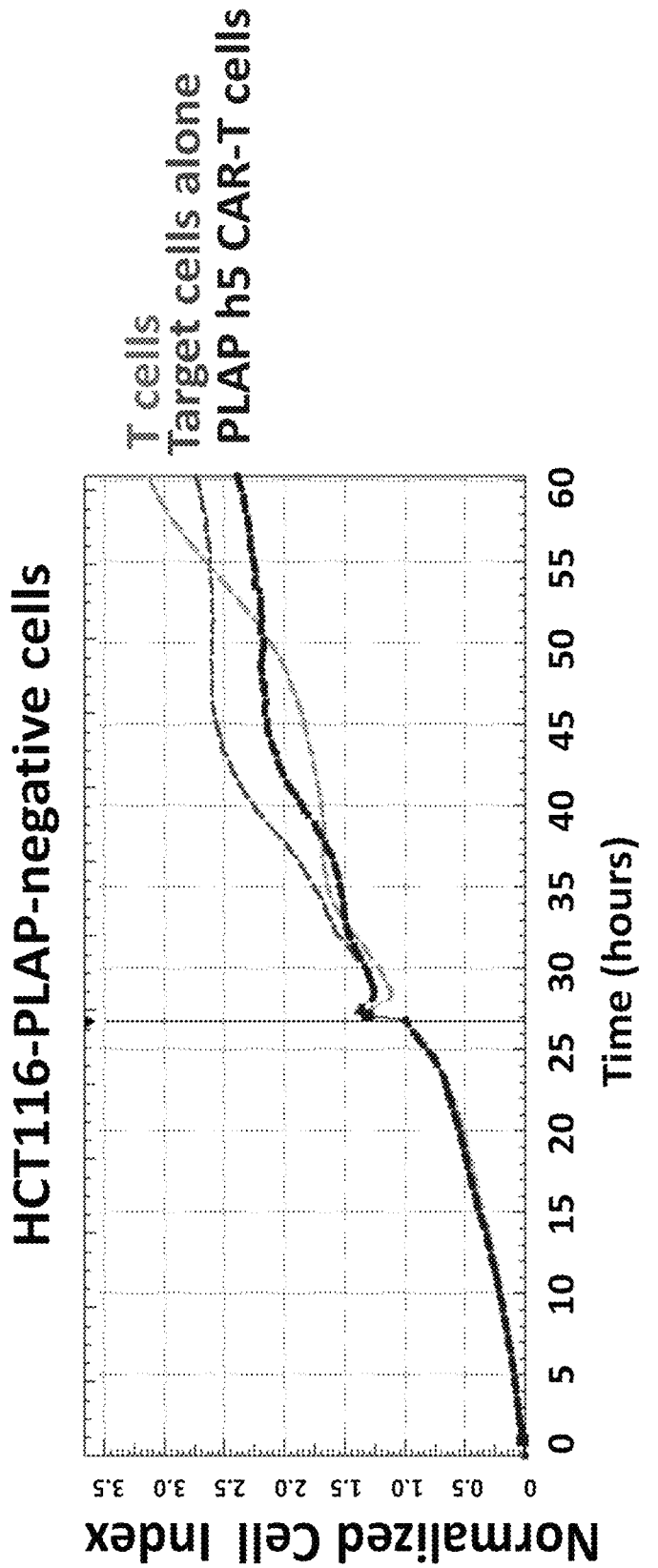
FIG. 8A(3)

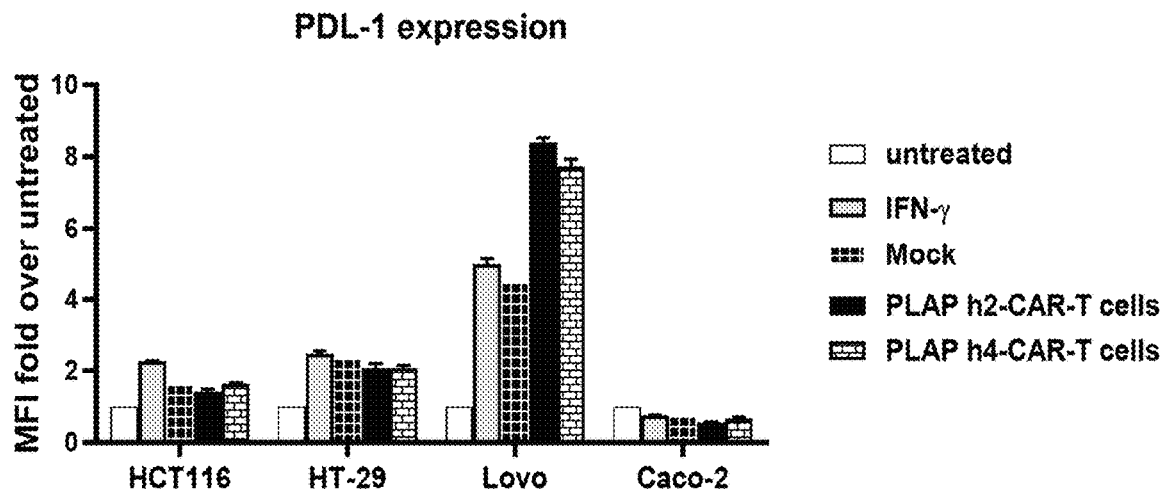
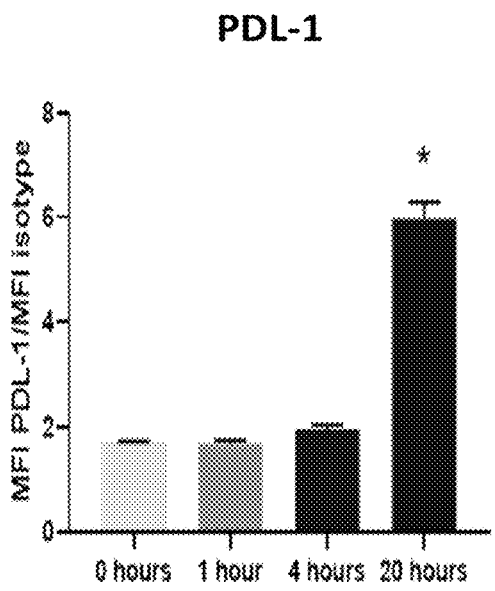
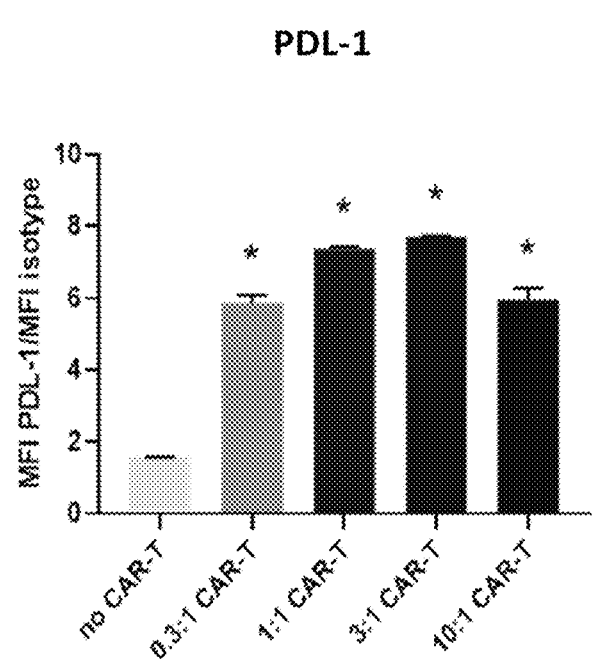
FIG. 9A
FIG. 9B
FIG. 9C

SEQUENCE LISTING

```
<160> NUMBER OF SEQ ID NOS: 35

<210> SEQ ID NO 1
<211> LENGTH: 535
<212> TYPE: PRT
<213> ORGANISM: Homo sapiens

<400> SEQUENCE: 1

Met Leu Gly Pro Cys Met Leu Leu Leu Leu Leu Leu Gly Leu Arg
1               5                   10                  15

Leu Gln Leu Ser Leu Gly Ile Ile Pro Val Glu Glu Asn Pro Asp
            20                  25                  30

Phe Trp Asn Arg Glu Ala Ala Glu Ala Leu Gly Ala Ala Lys Lys Leu
            35                  40                  45

Gln Pro Ala Gln Thr Ala Ala Lys Asn Leu Ile Ile Phe Leu Gly Asp
    50                  55                  60

Gly Met Gly Val Ser Thr Val Thr Ala Ala Arg Ile Leu Lys Gly Gln
65                  70                  75                  80

Lys Lys Asp Lys Leu Gly Pro Glu Ile Pro Leu Ala Met Asp Arg Phe
                85                  90                  95

Pro Tyr Val Ala Leu Ser Lys Thr Tyr Asn Val Asp Lys His Val Pro
            100                 105                 110

Asp Ser Gly Ala Thr Ala Thr Ala Tyr Leu Cys Gly Val Lys Gly Asn
        115                 120                 125

Phe Gln Thr Ile Gly Leu Ser Ala Ala Ala Arg Phe Asn Gln Cys Asn
    130                 135                 140

Thr Thr Arg Gly Asn Glu Val Ile Ser Val Met Asn Arg Ala Lys Lys
145                 150                 155                 160
```

Ala Gly Lys Ser Val Gly Val Thr Thr Arg Val Gln His Ala
            165             170             175

Ser Pro Ala Gly Thr Tyr Ala His Thr Val Asn Arg Asn Trp Tyr Ser
        180             185             190

Asp Ala Asp Val Pro Ala Ser Ala Arg Gln Glu Gly Cys Gln Asp Ile
        195             200             205

Ala Thr Gln Leu Ile Ser Asn Met Asp Ile Asp Val Ile Leu Gly Gly
210             215             220

Gly Arg Lys Tyr Met Phe Arg Met Gly Thr Pro Asp Pro Glu Tyr Pro
225             230             235             240

Asp Asp Tyr Ser Gln Gly Gly Thr Arg Leu Asp Gly Lys Asn Leu Val
            245             250             255

Gln Glu Trp Leu Ala Lys Arg Gln Gly Ala Arg Tyr Val Trp Asn Arg
            260             265             270

Thr Glu Leu Met Gln Ala Ser Leu Asp Pro Ser Val Thr His Leu Met
            275             280             285

Gly Leu Phe Glu Pro Gly Asp Met Lys Tyr Glu Ile His Arg Asp Ser
        290             295             300

Thr Leu Asp Pro Ser Leu Met Glu Met Thr Glu Ala Ala Leu Arg Leu
305             310             315             320

Leu Ser Arg Asn Pro Arg Gly Phe Phe Leu Phe Val Glu Gly Gly Arg
                325             330             335

Ile Asp His Gly His His Glu Ser Arg Ala Tyr Arg Ala Leu Thr Glu
            340             345             350

Thr Ile Met Phe Asp Asp Ala Ile Glu Arg Ala Gly Gln Leu Thr Ser
            355             360             365

Glu Glu Asp Thr Leu Ser Leu Val Thr Ala Asp His Ser His Val Phe
        370             375             380

Ser Phe Gly Gly Tyr Pro Leu Arg Gly Ser Ser Ile Phe Gly Leu Ala
385             390             395             400

Pro Gly Lys Ala Arg Asp Arg Lys Ala Tyr Thr Val Leu Leu Tyr Gly
            405             410             415

Asn Gly Pro Gly Tyr Val Leu Lys Asp Gly Ala Arg Pro Asp Val Thr
            420             425             430

Glu Ser Glu Ser Gly Ser Pro Glu Tyr Arg Gln Gln Ser Ala Val Pro
        435             440             445

Leu Asp Glu Glu Thr His Ala Gly Glu Asp Val Ala Val Phe Ala Arg
450             455             460

Gly Pro Gln Ala His Leu Val His Gly Val Gln Glu Gln Thr Phe Ile
465             470             475             480

Ala His Val Met Ala Phe Ala Cys Leu Glu Pro Tyr Thr Ala Cys
            485             490             495

Asp Leu Ala Pro Pro Ala Gly Thr Thr Asp Ala Ala His Pro Gly Arg
            500             505             510

Ser Val Val Pro Ala Leu Leu Pro Leu Leu Ala Gly Thr Leu Leu Leu
            515             520             525

Leu Glu Thr Ala Thr Ala Pro
            530             535

<210> SEQ ID NO 2
<211> LENGTH: 15
<212> TYPE: DNA
<213> ORGANISM: Artificial Sequence
<220> FEATURE:

<223> OTHER INFORMATION: Synthetic

<400> SEQUENCE: 2
tctagagccg ccacc                                                            15

<210> SEQ ID NO 3
<211> LENGTH: 1500
<212> TYPE: DNA
<213> ORGANISM: Mus musculus

<400> SEQUENCE: 3
atggccttac cagtgaccgc cttgctcctg ccgctggcct tgctgctcca cgccgccagg            60
ccggctagcc aggtgcagct gaaggagtca ggacctggcc tggtggcgcc ctcacagagc          120
ctgtccatca catgcactgt ctcagggttc tcattaacca gttatggtgt aagctgggtt          180
cgccagcctc caagaaaggg tctggagtgg ctggagtaa tatgggaaga cgggagcaca           240
aattatcatt cagctctcat atccagactg agcatcaaca aggataactc caagagccaa          300
gttttcttaa aactgaacag tctgcaaact gatgacacag ccacgtacta ctgtgccaaa          360
ccccactacg gtagcagcta cgtgggggct atggaatact ggggtcaagg aacctcagtc          420
accgtctcct caggtggcgg tggttctggt ggcggtggtt ctggtggcgg tggttctgac          480
atccagatga ctcagtctcc agcctcccta actgcatctg tgggagaaac tgtcaccatc          540
acctgtcgag caagtgaaaa tatttacagt tatgtagcat ggtatcagca gaaacaggga          600
aaatctcctc agttcctggt ctataatgca aaatccttag cagagggtgt gccatcaagg          660
ttcagtggca gyggatcagg cacacagttt tctctgaaga tcaacagcct gcagcctgaa          720
gattttggga attattactg tcaacatcat tatgttagtc cgtggacgtt cggtggaggc          780
accaagctgg aaatcagacg gctcgagaag cccaccacga cgccagcgcc gcgaccacca          840
acaccggcgc ccaccatcgc gtcgcagccc ctgtccctgc gcccagaggc gagccggcca          900
gcggcggggg gcgcagtgca cacgaggggg ctggacttcg ccagtgataa gccccttttgg         960
gtgctggtgg tggttggtgg agtcctggct tgctatagct tgctagtaac agtggccttt         1020
attattttct gggtgaggag taagaggagc aggctcctgc acagtgacta catgaacatg         1080
actccccgcc gccccgggcc caccegcaag cattaccagc cctatgcccc accacgcgac         1140
ttcgcagcct atcgctccag agtgaagttc agcaggagcg cagacgcccc cgcgtaccag         1200
cagggccaga accagctcta taacgagctc aatctaggac gaagagagga gtacgatgtt         1260
ttggacaaga gacgtggccg ggaccctgag atgggggggaa agccgcagag aaggaagaac         1320
cctcaggaag gcctgtacaa tgaactgcag aaagataaga tggcggaggc ctacagtgag         1380
attgggatga aggcgagcg ccggagggggc aaggggcacg atggccttta ccagggtctc          1440
agtacagcca ccaaggacac ctacgacgcc cttcacatgc aggccctgcc ccctcgctaa         1500

<210> SEQ ID NO 4
<211> LENGTH: 9
<212> TYPE: DNA
<213> ORGANISM: Artificial Sequence
<220> FEATURE:
<223> OTHER INFORMATION: Synthetic

<400> SEQUENCE: 4 taggaattc                                                                    9

<210> SEQ ID NO 5
<211> LENGTH: 501

```
<212> TYPE: PRT
<213> ORGANISM: Mus musculus
<220> FEATURE:
<221> NAME/KEY: misc_feature
<222> LOCATION: (224)..(224)
<223> OTHER INFORMATION: Xaa can be any naturally occurring amino acid

<400> SEQUENCE: 5
```

| | | | | | | | | | | | | | | | |
|---|---|---|---|---|---|---|---|---|---|---|---|---|---|---|---|
| Met | Ala | Leu | Pro | Val | Thr | Ala | Leu | Leu | Leu | Pro | Leu | Ala | Leu | Leu | Leu |
| 1 | | | | 5 | | | | | 10 | | | | | 15 | |
| His | Ala | Ala | Arg | Pro | Ala | Ser | Gln | Val | Gln | Leu | Lys | Glu | Ser | Gly | Pro |
| | | | 20 | | | | | 25 | | | | | 30 | | |
| Gly | Leu | Val | Ala | Pro | Ser | Gln | Ser | Leu | Ser | Ile | Thr | Cys | Thr | Val | Ser |
| | | | 35 | | | | | 40 | | | | | 45 | | |
| Gly | Phe | Ser | Leu | Thr | Ser | Tyr | Gly | Val | Ser | Trp | Val | Arg | Gln | Pro | Pro |
| | 50 | | | | | 55 | | | | | 60 | | | | |
| Arg | Lys | Gly | Leu | Glu | Trp | Leu | Gly | Val | Ile | Trp | Glu | Asp | Gly | Ser | Thr |
| 65 | | | | | 70 | | | | | 75 | | | | | 80 |
| Asn | Tyr | His | Ser | Ala | Leu | Ile | Ser | Arg | Leu | Ser | Ile | Asn | Lys | Asp | Asn |
| | | | | 85 | | | | | 90 | | | | | 95 | |
| Ser | Lys | Ser | Gln | Val | Phe | Leu | Lys | Leu | Asn | Ser | Leu | Gln | Thr | Asp | Asp |
| | | | 100 | | | | | 105 | | | | | 110 | | |
| Thr | Ala | Thr | Tyr | Tyr | Cys | Ala | Lys | Pro | His | Tyr | Gly | Ser | Ser | Tyr | Val |
| | | | 115 | | | | | 120 | | | | | 125 | | |
| Gly | Ala | Met | Glu | Tyr | Trp | Gly | Gln | Gly | Thr | Ser | Val | Thr | Val | Ser | Ser |
| | | | 130 | | | | | 135 | | | | | 140 | | |
| Gly | Gly | Gly | Gly | Ser | Gly | Gly | Gly | Ser | Gly | Gly | Gly | Gly | Ser | Asp | |
| 145 | | | | | 150 | | | | | 155 | | | | | 160 |
| Ile | Gln | Met | Thr | Gln | Ser | Pro | Ala | Ser | Leu | Thr | Ala | Ser | Val | Gly | Glu |
| | | | | 165 | | | | | 170 | | | | | 175 | |
| Thr | Val | Thr | Ile | Thr | Cys | Arg | Ala | Ser | Glu | Asn | Ile | Tyr | Ser | Tyr | Val |
| | | | 180 | | | | | 185 | | | | | 190 | | |
| Ala | Trp | Tyr | Gln | Gln | Lys | Gln | Gly | Lys | Ser | Pro | Gln | Phe | Leu | Val | Tyr |
| | | | 195 | | | | | 200 | | | | | 205 | | |
| Asn | Ala | Lys | Ser | Leu | Ala | Glu | Gly | Val | Pro | Ser | Arg | Phe | Ser | Gly | Xaa |
| | 210 | | | | | 215 | | | | | 220 | | | | |
| Gly | Ser | Gly | Thr | Gln | Phe | Ser | Leu | Lys | Ile | Asn | Ser | Leu | Gln | Pro | Glu |
| 225 | | | | | 230 | | | | | 235 | | | | | 240 |
| Asp | Phe | Gly | Asn | Tyr | Tyr | Cys | Gln | His | His | Tyr | Val | Ser | Pro | Trp | Thr |
| | | | | 245 | | | | | 250 | | | | | 255 | |
| Phe | Gly | Gly | Gly | Thr | Lys | Leu | Glu | Ile | Arg | Arg | Leu | Glu | Lys | Pro | Thr |
| | | | 260 | | | | | 265 | | | | | 270 | | |
| Thr | Thr | Pro | Ala | Pro | Arg | Pro | Pro | Thr | Pro | Ala | Pro | Thr | Ile | Ala | Ser |
| | | | | 275 | | | | | 280 | | | | | 285 | |
| Gln | Pro | Leu | Ser | Leu | Arg | Pro | Glu | Ala | Ser | Arg | Pro | Ala | Ala | Gly | Gly |
| | | 290 | | | | | 295 | | | | | 300 | | | |
| Ala | Val | His | Thr | Arg | Gly | Leu | Asp | Phe | Ala | Ser | Asp | Lys | Pro | Phe | Trp |
| 305 | | | | | 310 | | | | | 315 | | | | | 320 |
| Val | Leu | Val | Val | Val | Gly | Gly | Val | Leu | Ala | Cys | Tyr | Ser | Leu | Leu | Val |
| | | | | 325 | | | | | 330 | | | | | 335 | |
| Thr | Val | Ala | Phe | Ile | Ile | Phe | Trp | Val | Arg | Ser | Lys | Arg | Ser | Arg | Leu |
| | | | 340 | | | | | 345 | | | | | 350 | | |
| Leu | His | Ser | Asp | Tyr | Met | Asn | Met | Thr | Pro | Arg | Arg | Pro | Gly | Pro | Thr |
| | | | | 355 | | | | | 360 | | | | | 365 | |
| Arg | Lys | His | Tyr | Gln | Pro | Tyr | Ala | Pro | Pro | Arg | Asp | Phe | Ala | Ala | Tyr |

-continued

```
                370                 375                 380
Arg Ser Arg Val Lys Phe Ser Arg Ser Ala Asp Ala Pro Ala Tyr Gln
385                 390                 395                 400

Gln Gly Gln Asn Gln Leu Tyr Asn Glu Leu Asn Leu Gly Arg Arg Glu
                405                 410                 415

Glu Tyr Asp Val Leu Asp Lys Arg Arg Gly Arg Asp Pro Glu Met Glu
                420                 425                 430

Thr Gly Gly Lys Pro Gln Arg Arg Lys Asn Pro Gln Glu Gly Leu Tyr
                435                 440                 445

Asn Glu Leu Gln Lys Asp Lys Met Ala Glu Ala Tyr Ser Glu Ile Gly
                450                 455                 460

Met Lys Gly Glu Arg Arg Gly Lys Gly His Asp Gly Leu Tyr Gln
465                 470                 475                 480

Gly Leu Ser Thr Ala Thr Lys Asp Thr Tyr Asp Ala Leu His Met Gln
                485                 490                 495

Ala Leu Pro Pro Arg
                500
```

```
<210> SEQ ID NO 6
<211> LENGTH: 121
<212> TYPE: PRT
<213> ORGANISM: Mus musculus

<400> SEQUENCE: 6

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
                20                  25                  30

Gly Val Ser Trp Val Arg Gln Pro Pro Arg Lys Gly Leu Glu Trp Leu
            35                  40                  45

Gly Val Ile Trp Glu Asp Gly Ser Thr Asn Tyr His Ser Ala Leu Ile
        50                  55                  60

Ser Arg Leu Ser Ile Asn Lys Asp Asn Ser Lys Ser Gln Val Phe Leu
65              70                  75                  80

Lys Leu Asn Ser Leu Gln Thr Asp Asp Thr Ala Thr Tyr Tyr Cys Ala
                85                  90                  95

Lys Pro His Tyr Gly Ser Ser Tyr Val Gly Ala Met Glu Tyr Trp Gly
                100                 105                 110

Gln Gly Thr Ser Val Thr Val Ser Ser
            115                 120
```

```
<210> SEQ ID NO 7
<211> LENGTH: 108
<212> TYPE: PRT
<213> ORGANISM: Mus musculus
<220> FEATURE:
<221> NAME/KEY: misc_feature
<222> LOCATION: (65)..(65)
<223> OTHER INFORMATION: Xaa can be any naturally occurring amino acid

<400> SEQUENCE: 7

Asp Ile Gln Met Thr Gln Ser Pro Ala Ser Leu Thr Ala Ser Val Gly
1               5                   10                  15

Glu Thr Val Thr Ile Thr Cys Arg Ala Ser Glu Asn Ile Tyr Ser Tyr
                20                  25                  30

Val Ala Trp Tyr Gln Gln Lys Gln Gly Lys Ser Pro Gln Phe Leu Val
            35                  40                  45
```

```
Tyr Asn Ala Lys Ser Leu Ala Glu Gly Val Pro Ser Arg Phe Ser Gly
         50                  55                  60

Xaa Gly Ser Gly Thr Gln Phe Ser Leu Lys Ile Asn Ser Leu Gln Pro
 65                  70                  75                  80

Glu Asp Phe Gly Asn Tyr Tyr Cys Gln His His Tyr Val Ser Pro Trp
                     85                  90                  95

Thr Phe Gly Gly Gly Thr Lys Leu Glu Ile Arg Arg
                100                 105

<210> SEQ ID NO 8
<211> LENGTH: 244
<212> TYPE: PRT
<213> ORGANISM: Mus musculus
<220> FEATURE:
<221> NAME/KEY: misc_feature
<222> LOCATION: (201)..(201)
<223> OTHER INFORMATION: Xaa can be any naturally occurring amino acid

<400> SEQUENCE: 8

Gln Val Gln Leu Lys Glu Ser Gly Pro Gly Leu Val Ala Pro Ser Gln
  1               5                  10                  15

Ser Leu Ser Ile Thr Cys Thr Val Ser Gly Phe Ser Leu Thr Ser Tyr
                 20                  25                  30

Gly Val Ser Trp Val Arg Gln Pro Pro Arg Lys Gly Leu Glu Trp Leu
             35                  40                  45

Gly Val Ile Trp Glu Asp Gly Ser Thr Asn Tyr His Ser Ala Leu Ile
         50                  55                  60

Ser Arg Leu Ser Ile Asn Lys Asp Asn Ser Lys Ser Gln Val Phe Leu
 65                  70                  75                  80

Lys Leu Asn Ser Leu Gln Thr Asp Asp Thr Ala Thr Tyr Tyr Cys Ala
                 85                  90                  95

Lys Pro His Tyr Gly Ser Ser Tyr Val Gly Ala Met Glu Tyr Trp Gly
                100                 105                 110

Gln Gly Thr Ser Val Thr Val Ser Ser Gly Gly Gly Ser Gly Gly
                115                 120                 125

Gly Gly Ser Gly Gly Gly Ser Asp Ile Gln Met Thr Gln Ser Pro
            130                 135                 140

Ala Ser Leu Thr Ala Ser Val Gly Glu Thr Val Thr Ile Thr Cys Arg
145                 150                 155                 160

Ala Ser Glu Asn Ile Tyr Ser Tyr Val Ala Trp Tyr Gln Gln Lys Gln
                165                 170                 175

Gly Lys Ser Pro Gln Phe Leu Val Tyr Asn Ala Lys Ser Leu Ala Glu
                180                 185                 190

Gly Val Pro Ser Arg Phe Ser Gly Xaa Gly Ser Gly Thr Gln Phe Ser
            195                 200                 205

Leu Lys Ile Asn Ser Leu Gln Pro Glu Asp Phe Gly Asn Tyr Tyr Cys
210                 215                 220

Gln His His Tyr Val Ser Pro Trp Thr Phe Gly Gly Gly Thr Lys Leu
225                 230                 235                 240

Glu Ile Arg Arg

<210> SEQ ID NO 9
<211> LENGTH: 63
<212> TYPE: DNA
<213> ORGANISM: Homo sapiens

<400> SEQUENCE: 9
```
atggccttac cagtgaccgc cttgctcctg ccgctggcct tgctgctcca cgccgccagg    60
ccg                                                                  63

<210> SEQ ID NO 10
<211> LENGTH: 801
<212> TYPE: DNA
<213> ORGANISM: Mus musculus

<400> SEQUENCE: 10
atggccttac cagtgaccgc cttgctcctg ccgctggcct tgctgctcca cgccgccagg    60
ccggctagcc aggtgcagct gaaggagtca ggacctggcc tggtggcgcc ctcacagagc   120
ctgtccatca catgcactgt ctcagggttc tcattaacca gttatggtgt aagctgggtt   180
cgccagcctc caagaaaggg tctggagtgg ctgggagtaa tatgggaaga cgggagcaca   240
aattatcatt cagctctcat atccagactg agcatcaaca aggataactc caagagccaa   300
gttttcttaa aactgaacag tctgcaaact gatgacacag ccacgtacta ctgtgccaaa   360
ccccactacg gtagcagcta cgtgggggct atggaatact ggggtcaagg aacctcagtc   420
accgtctcct caggtggcgg tggttctggt ggcggtggtt ctggtggcgg tggttctgac   480
atccagatga ctcagtctcc agcctcccta actgcatctg tgggagaaac tgtcaccatc   540
acctgtcgag caagtgaaaa tatttacagt tatgtagcat ggtatcagca gaaacaggga   600
aaatctcctc agttcctggt ctataatgca aaatccttag cagagggtgt gccatcaagg   660
ttcagtggca gyggatcagg cacacagttt tctctgaaga tcaacagcct gcagcctgaa   720
gattttggga attattactg tcaacatcat tatgttagtc cgtggacgtt cggtggaggc   780
accaagctgg aaatcagacg g                                             801

<210> SEQ ID NO 11
<211> LENGTH: 147
<212> TYPE: DNA
<213> ORGANISM: Homo sapiens

<400> SEQUENCE: 11
aagcccacca cgacgccagc gccgcgacca ccaacaccgg cgcccaccat cgcgtcgcag    60 ccctgtccc tgcgcccaga ggcgagccgg ccagcggcgg ggggcgcagt gcacacgagg    120
gggctggact cgccagtga taagccc                                        147

<210> SEQ ID NO 12
<211> LENGTH: 204
<212> TYPE: DNA
<213> ORGANISM: Homo sapiens

<400> SEQUENCE: 12
ttttgggtgc tggtggtggt tggtggagtc ctggcttgct atagcttgct agtaacagtg    60
gcctttatta ttttctgggt gaggagtaag aggagcaggc tcctgcacag tgactacatg   120
aacatgactc cccgccgccc cgggcccacc cgcaagcatt accagcccta tgccccacca   180
cgcgacttcg cagcctatcg ctcc                                          204

<210> SEQ ID NO 13
<211> LENGTH: 342
<212> TYPE: DNA
<213> ORGANISM: Homo sapiens

<400> SEQUENCE: 13
agagtgaagt tcagcaggag cgcagacgcc cccgcgtacc agcagggcca gaaccagctc    60

```
tataacgagc tcaatctagg acgaagagag gagtacgatg ttttggacaa gagacgtggc    120
cgggaccctg agatggggg  aaagccgaga aggaagaacc ctcaggaagg cctgtacaat    180
gaactgcaga aagataagat ggcggaggcc tacagtgaga ttgggatgaa aggcgagcgc    240
cggaggggca aggggcacga tggcctttac cagggtctca gtacagccac caaggacacc    300
tacgacgccc ttcacatgca ggccctgccc cctcgctaat ag                       342
```

```
<210> SEQ ID NO 14
<211> LENGTH: 1500
<212> TYPE: DNA
<213> ORGANISM: Homo sapiens

<400> SEQUENCE: 14
atggccttac cagtgaccgc cttgctcctg ccgctggcct tgctgctcca cgccgccagg     60
ccggctagcc aggtccaact gcaggagagc ggtccaggtc ttgtgagacc tagccagacc    120
ctgagcctga cctgcaccgt gtctggcttc accttcacca gttatggtgt aagctgggtg    180
agacagccac ctggacgagg tcttgagtgg attggagtaa tatgggaaga cgggagcaca    240
aattatcatt cagctctcat atccagagtg acaatgctgg tagacaccag caagaaccag    300
ttcagcctga gactcagcag cgtgacagcc gccgacaccg cggtctatta ttgtgcaaga    360
ccccactacg gtagcagcta cgtggggggct atggaatact gggtcaagg  cagcctcgtc    420 acagtctcct caggtggcgg tggttctggt ggcggtggtt ctggtggcgg tggttctgac    480
atccagatga cccagagccc aagcagcctg agcgccagcg tgggtgacag agtgaccatc    540
acctgtcgag caagtgaaaa tatttacagt tatgtagcat ggtaccagca gaagccaggt    600
aaggctccaa agctgctgat ctacaatgca aatccttag  cagagggtgt gccaagcaga    660
ttcagcggta gcggtagcgg taccgacttc accttcacca tcagcagcct ccagccagag    720
gacatcgcca cctactactg ccaacatcat tatgttagtc cgtggacgtt cggccaaggg    780
accaaggtgg aaatcaaacg tctcgagaag cccaccacga cgccagcgcc gcgaccacca    840
acaccggcgc ccaccatcgc gtcgcagccc ctgtccctgc gcccagaggc gagcggcca    900 gcggcggggg gcgcagtgca cacgaggggg ctggacttcg ccagtgataa gcccttttgg    960
gtgctggtgg tggttggtgg agtcctggct tgctatagct tgctagtaac agtggccttt   1020
attattttct gggtgaggag taagaggagc aggctcctgc acagtgacta catgaacatg   1080
actccccgcc gccccgggcc cacccgcaag cattaccagc cctatgcccc accacgcgac   1140
ttcgcagcct atcgctccag agtgaagttc agcaggagcg cagacgcccc cgcgtaccag   1200
cagggccaga accagctcta taacgagctc aatctaggac gaagagagga gtacgatgtt   1260
ttggacaaga cgtggccg  ggaccctgag atgggggaa agccgcagag aaggaagaac   1320
cctcaggaag gcctgtacaa tgaactgcag aaagataaga tggcggaggc ctacagtgag   1380
attgggatga aaggcgagcg ccggaggggc aaggggcacg atggccttta ccagggtctc   1440
agtacagcca ccaaggacac ctacgacgcc cttcacatgc aggccctgcc cctcgctaa    1500
```

```
<210> SEQ ID NO 15
<211> LENGTH: 499
<212> TYPE: PRT
<213> ORGANISM: Homo sapiens

<400> SEQUENCE: 15

Met Ala Leu Pro Val Thr Ala Leu Leu Leu Pro Leu Ala Leu Leu Leu
1               5                   10                  15
```

```
His Ala Ala Arg Pro Ala Ser Gln Val Gln Leu Gln Glu Ser Gly Pro
             20                  25                  30
Gly Leu Val Arg Pro Ser Gln Thr Leu Ser Leu Thr Cys Thr Val Ser
         35                  40                  45
Gly Phe Thr Phe Thr Ser Tyr Gly Val Ser Trp Val Arg Gln Pro Pro
 50                  55                  60
Gly Arg Gly Leu Glu Trp Ile Gly Val Ile Trp Glu Asp Gly Ser Thr
 65                  70                  75                  80
Asn Tyr His Ser Ala Leu Ile Ser Arg Val Thr Met Leu Val Asp Thr
             85                  90                  95
Ser Lys Asn Gln Phe Ser Leu Arg Leu Ser Ser Val Thr Ala Ala Asp
            100                 105                 110
Thr Ala Val Tyr Tyr Cys Ala Arg Pro His Tyr Gly Ser Ser Tyr Val
            115                 120                 125
Gly Ala Met Glu Tyr Trp Gly Gln Gly Ser Leu Val Thr Val Ser Ser
            130                 135                 140
Gly Gly Gly Gly Ser Gly Gly Gly Ser Gly Gly Gly Gly Ser Asp
145                 150                 155                 160
Ile Gln Met Thr Gln Ser Pro Ser Ser Leu Ser Ala Ser Val Gly Asp
                165                 170                 175
Arg Val Thr Ile Thr Cys Arg Ala Ser Glu Asn Ile Tyr Ser Tyr Val
                180                 185                 190
Ala Trp Tyr Gln Gln Lys Pro Gly Lys Ala Pro Lys Leu Leu Ile Tyr
            195                 200                 205
Asn Ala Lys Ser Leu Ala Glu Gly Val Pro Ser Arg Phe Ser Gly Ser
            210                 215                 220
Gly Ser Gly Thr Asp Phe Thr Phe Thr Ile Ser Ser Leu Gln Pro Glu
225                 230                 235                 240
Asp Ile Ala Thr Tyr Tyr Cys Gln His His Tyr Val Ser Pro Trp Thr
                245                 250                 255
Phe Gly Gln Gly Thr Lys Val Glu Ile Lys Arg Leu Glu Lys Pro Thr
                260                 265                 270
Thr Thr Pro Ala Pro Arg Pro Pro Thr Pro Ala Pro Thr Ile Ala Ser
            275                 280                 285
Gln Pro Leu Ser Leu Arg Pro Glu Ala Ser Arg Pro Ala Ala Gly Gly
            290                 295                 300
Ala Val His Thr Arg Gly Leu Asp Phe Ala Ser Asp Lys Pro Phe Trp
305                 310                 315                 320
Val Leu Val Val Val Gly Gly Val Leu Ala Cys Tyr Ser Leu Leu Val
                325                 330                 335
Thr Val Ala Phe Ile Ile Phe Trp Val Arg Ser Lys Arg Ser Arg Leu
                340                 345                 350
Leu His Ser Asp Tyr Met Asn Met Thr Pro Arg Arg Pro Gly Pro Thr
            355                 360                 365
Arg Lys His Tyr Gln Pro Tyr Ala Pro Pro Arg Asp Phe Ala Ala Tyr
            370                 375                 380
Arg Ser Arg Val Lys Phe Ser Arg Ser Ala Asp Ala Pro Ala Tyr Gln
385                 390                 395                 400
Gln Gly Gln Asn Gln Leu Tyr Asn Glu Leu Asn Leu Gly Arg Arg Glu
                405                 410                 415
Glu Tyr Asp Val Leu Asp Lys Arg Arg Gly Arg Asp Pro Glu Met Gly
            420                 425                 430
```

```
Gly Lys Pro Gln Arg Arg Lys Asn Pro Gln Glu Gly Leu Tyr Asn Glu
            435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg
```

<210> SEQ ID NO 16
<211> LENGTH: 121
<212> TYPE: PRT
<213> ORGANISM: Homo sapiens

<400> SEQUENCE: 16

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Ser Tyr
            20                  25                  30

Gly Val Ser Trp Val Arg Gln Pro Pro Gly Arg Gly Leu Glu Trp Ile
        35                  40                  45

Gly Val Ile Trp Glu Asp Gly Ser Thr Asn Tyr His Ser Ala Leu Ile
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Pro His Tyr Gly Ser Ser Tyr Val Gly Ala Met Glu Tyr Trp Gly
            100                 105                 110

Gln Gly Ser Leu Val Thr Val Ser Ser
        115                 120
```

<210> SEQ ID NO 17
<211> LENGTH: 108
<212> TYPE: PRT
<213> ORGANISM: Homo sapiens

<400> SEQUENCE: 17

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Val Ala Trp Tyr Gln Gln Lys Pro Gly Lys Ala Pro Lys Leu Leu Ile
        35                  40                  45

Tyr Asn Ala Lys Ser Leu Ala Glu Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln His His Tyr Val Ser Pro Trp
                85                  90                  95

Thr Phe Gly Gln Gly Thr Lys Val Glu Ile Lys Arg
            100                 105
```

<210> SEQ ID NO 18
<211> LENGTH: 244
<212> TYPE: PRT

<213> ORGANISM: Homo sapiens

<400> SEQUENCE: 18

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Ser Tyr
            20                  25                  30

Gly Val Ser Trp Val Arg Gln Pro Pro Gly Arg Gly Leu Glu Trp Ile
        35                  40                  45

Gly Val Ile Trp Glu Asp Gly Ser Thr Asn Tyr His Ser Ala Leu Ile
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Pro His Tyr Gly Ser Ser Tyr Val Gly Ala Met Glu Tyr Trp Gly
            100                 105                 110

Gln Gly Ser Leu Val Thr Val Ser Gly Gly Gly Ser Gly Gly
        115                 120                 125

Gly Gly Ser Gly Gly Gly Ser Asp Ile Gln Met Thr Gln Ser Pro
    130                 135                 140

Ser Ser Leu Ser Ala Ser Val Gly Asp Arg Val Thr Ile Thr Cys Arg
145                 150                 155                 160

Ala Ser Glu Asn Ile Tyr Ser Tyr Val Ala Trp Tyr Gln Lys Pro
                165                 170                 175

Gly Lys Ala Pro Lys Leu Leu Ile Tyr Asn Ala Lys Ser Leu Ala Glu
            180                 185                 190

Gly Val Pro Ser Arg Phe Ser Gly Ser Gly Ser Gly Thr Asp Phe Thr
        195                 200                 205

Phe Thr Ile Ser Ser Leu Gln Pro Glu Asp Ile Ala Thr Tyr Tyr Cys
    210                 215                 220

Gln His His Tyr Val Ser Pro Trp Thr Phe Gly Gln Gly Thr Lys Val
225                 230                 235                 240

Glu Ile Lys Arg
```

<210> SEQ ID NO 19
<211> LENGTH: 1497
<212> TYPE: DNA
<213> ORGANISM: Homo sapiens

<400> SEQUENCE: 19

```
atggcctta c cagtgaccgc cttgctcctg ccgctggcct tgctgctcca cgccgccagg      60
ccggctagcc aggtgcagct tcaggaaagt ggaccgggcc ttgtcaaacc gtcagagacc     120
ctttcactga cttgcactgt aagtggtttc tccctgacaa gctacggagt ctcctggata     180
cgccagccag cggggaaagg gcttgagtgg atcggtgtga tctgggaaga cgggagtaca     240
aactatcact cagcactcat tagtcgagta acaatgtccg ttgacacttc caagaatcaa     300
ttcagtttga aactgtctag tgtgacggct gcggatacag cggtttatta ctgtgccagg     360
cctcattacg gaagttctta tgttggtgca atggagtatt ggggagccgg cacaactgtc     420
actgtgagct ccggcggggg cggaagtggg ggaggaggct caggcggagg tggaagtgat     480
atacagatga cccagagtcc tagctcactc tctgcgtccg taggggaccg ggtaaccatc     540
acatgccgcg ccagcgagaa tatatacagt tacgttgcat ggtaccagca aaaacctggc     600
```

```
aaggcgccga agctgttgat ctacaacgcc aaaagtctcg cttccggggt ccccagccga   660
ttttctggct caggtagtgg cacagatttc acactcacaa taagctctct ccagcccgaa   720
gactttgcga cgtactactg ccagcatcat tatgttagtc cttggacgtt tggcggaggc   780
acaaaattgg aaataaaact cgagaagccc accacgacgc cagcgccgcg accaccaaca   840
ccggcgccca ccatcgcgtc gcagcccctg tccctgcgcc cagaggcgag ccggccagcg   900
gcggggggcg cagtgcacac gagggggctg gacttcgcca gtgataagcc cttttgggtg   960
ctggtggtgg ttggtggagt cctggcttgc tatagcttgc tagtaacagt ggcctttatt  1020
attttctggg tgaggagtaa gaggagcagg ctcctgcaca gtgactacat gaacatgact  1080
ccccgccgcc ccgggcccac ccgcaagcat taccagccct atgccccacc acgcgacttc  1140
gcagcctatc gctccagagt gaagttcagc aggagcgcag acgccccgc gtaccagcag  1200 ggccagaacc agctctataa cgagctcaat ctaggacgaa gagaggagta cgatgttttg  1260
gacaagagac gtggccggga ccctgagatg gggggaaagc cgcagagaag gaagaaccct  1320
caggaaggcc tgtacaatga actgcagaaa gataagatgg cggaggccta cagtgagatt  1380
gggatgaaag gcgagcgccg gaggggcaag gggcacgatg gcctttacca gggtctcagt  1440
acagccacca aggacaccta cgacgcccctt cacatgcagg ccctgccccc tcgctaa     1497
```

<210> SEQ ID NO 20
<211> LENGTH: 498
<212> TYPE: PRT
<213> ORGANISM: Homo sapiens

<400> SEQUENCE: 20

```
Met Ala Leu Pro Val Thr Ala Leu Leu Leu Pro Leu Ala Leu Leu Leu
1               5                   10                  15

His Ala Ala Arg Pro Ala Ser Gln Val Gln Leu Gln Glu Ser Gly Pro
            20                  25                  30

Gly Leu Val Lys Pro Ser Glu Thr Leu Ser Leu Thr Cys Thr Val Ser
        35                  40                  45

Gly Phe Ser Leu Thr Ser Tyr Gly Val Ser Trp Ile Arg Gln Pro Ala
    50                  55                  60

Gly Lys Gly Leu Glu Trp Ile Gly Val Ile Trp Glu Asp Gly Ser Thr
65                  70                  75                  80

Asn Tyr His Ser Ala Leu Ile Ser Arg Val Thr Met Ser Val Asp Thr
                85                  90                  95

Ser Lys Asn Gln Phe Ser Leu Lys Leu Ser Ser Val Thr Ala Ala Asp
            100                 105                 110

Thr Ala Val Tyr Tyr Cys Ala Arg Pro His Tyr Gly Ser Ser Tyr Val
        115                 120                 125

Gly Ala Met Glu Tyr Trp Gly Ala Gly Thr Thr Val Thr Val Ser Ser
    130                 135                 140

Gly Gly Gly Gly Ser Gly Gly Gly Gly Ser Gly Gly Gly Gly Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Arg Ala Ser Glu Asn Ile Tyr Ser Tyr Val
            180                 185                 190

Ala Trp Tyr Gln Gln Lys Pro Gly Lys Ala Pro Lys Leu Leu Ile Tyr
        195                 200                 205

Asn Ala Lys Ser Leu Ala Ser Gly Val Pro Ser Arg Phe Ser Gly Ser
    210                 215                 220
```

```
Gly Ser Gly Thr Asp Phe Thr Leu Thr Ile Ser Ser Leu Gln Pro Glu
225                 230                 235                 240

Asp Phe Ala Thr Tyr Tyr Cys Gln His His Tyr Val Ser Pro Trp Thr
            245                 250                 255

Phe Gly Gly Gly Thr Lys Leu Glu Ile Lys Leu Glu Lys Pro Thr Thr
        260                 265                 270

Thr Pro Ala Pro Arg Pro Pro Thr Pro Ala Pro Thr Ile Ala Ser Gln
    275                 280                 285

Pro Leu Ser Leu Arg Pro Glu Ala Ser Arg Pro Ala Ala Gly Gly Ala
290                 295                 300

Val His Thr Arg Gly Leu Asp Phe Ala Ser Asp Lys Pro Phe Trp Val
305                 310                 315                 320

Leu Val Val Val Gly Gly Val Leu Ala Cys Tyr Ser Leu Leu Val Thr
                325                 330                 335

Val Ala Phe Ile Ile Phe Trp Val Arg Ser Lys Arg Ser Arg Leu Leu
                340                 345                 350

His Ser Asp Tyr Met Asn Met Thr Pro Arg Arg Pro Gly Pro Thr Arg
            355                 360                 365

Lys His Tyr Gln Pro Tyr Ala Pro Pro Arg Asp Phe Ala Ala Tyr Arg
370                 375                 380

Ser Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Gln Arg Arg Lys Asn Pro Gln Glu Gly Leu Tyr Asn Glu Leu
            435                 440                 445

Gln Lys Asp Lys Met Ala Glu Ala Tyr Ser Glu Ile Gly Met Lys Gly
    450                 455                 460

Glu Arg Arg Arg Gly Lys Gly His Asp Gly Leu Tyr Gln Gly Leu Ser
465                 470                 475                 480

Thr Ala Thr Lys Asp Thr Tyr Asp Ala Leu His Met Gln Ala Leu Pro
                485                 490                 495

Pro Arg

<210> SEQ ID NO 21
<211> LENGTH: 121
<212> TYPE: PRT
<213> ORGANISM: Homo sapiens

<400> SEQUENCE: 21

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val Ser Trp Ile Arg Gln Pro Ala Gly Lys Gly Leu Glu Trp Ile
        35                  40                  45

Gly Val Ile Trp Glu Asp Gly Ser Thr Asn Tyr His Ser Ala Leu Ile
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95
```

```
Arg Pro His Tyr Gly Ser Ser Tyr Val Gly Ala Met Glu Tyr Trp Gly
            100                 105                 110

Ala Gly Thr Thr Val Thr Val Ser Ser
            115                 120
```

<210> SEQ ID NO 22
<211> LENGTH: 107
<212> TYPE: PRT
<213> ORGANISM: Homo sapiens

<400> SEQUENCE: 22

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Val Ala Trp Tyr Gln Gln Lys Pro Gly Lys Ala Pro Lys Leu Leu Ile
        35                  40                  45

Tyr Asn Ala Lys Ser Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Val Ser Pro Trp
                85                  90                  95

Thr Phe Gly Gly Gly Thr Lys Leu Glu Ile Lys
            100                 105
```

<210> SEQ ID NO 23
<211> LENGTH: 243
<212> TYPE: PRT
<213> ORGANISM: Homo sapiens

<400> SEQUENCE: 23

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val Ser Trp Ile Arg Gln Pro Ala Gly Lys Gly Leu Glu Trp Ile
        35                  40                  45

Gly Val Ile Trp Glu Asp Gly Ser Thr Asn Tyr His Ser Ala Leu Ile
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Pro His Tyr Gly Ser Ser Tyr Val Gly Ala Met Glu Tyr Trp Gly
            100                 105                 110

Ala Gly Thr Thr Val Thr Val Ser Ser Gly Gly Gly Ser Gly Gly
            115                 120                 125

Gly Gly Ser Gly Gly Gly Ser Asp Ile Gln Met Thr Gln Ser Pro
        130                 135                 140

Ser Ser Leu Ser Ala Ser Val Gly Asp Arg Val Thr Ile Thr Cys Arg
145                 150                 155                 160

Ala Ser Glu Asn Ile Tyr Ser Tyr Val Ala Trp Tyr Gln Gln Lys Pro
                165                 170                 175

Gly Lys Ala Pro Lys Leu Leu Ile Tyr Asn Ala Lys Ser Leu Ala Ser
            180                 185                 190
```

Gly Val Pro Ser Arg Phe Ser Gly Ser Gly Ser Gly Thr Asp Phe Thr
            195                 200                 205

Leu Thr Ile Ser Ser Leu Gln Pro Glu Asp Phe Ala Thr Tyr Tyr Cys
        210                 215                 220

Gln His His Tyr Val Ser Pro Trp Thr Phe Gly Gly Gly Thr Lys Leu
225                 230                 235                 240

Glu Ile Lys

<210> SEQ ID NO 24
<211> LENGTH: 1500
<212> TYPE: DNA
<213> ORGANISM: Homo sapiens

<400> SEQUENCE: 24

| | | | | | |
|---|---|---|---|---|---|
| atggccttac | cagtgaccgc | cttgctcctg | ccgctggcct | tgctgctcca | cgccgccagg | 60 |
| ccggctagcc | aggttcaact | tcaagaatca | ggaccgggct | tggttaaacc | ttccgaaact | 120 |
| ctgagcctta | cttgtacagt | gtctggtgga | tctattacga | gctacggagt | aagttggatc | 180 |
| cggcaaccac | ccgggaaagg | gctcgaatgg | ataggggtga | tatgggagga | tggttcaacc | 240 |
| aactaccata | gcgctctgat | cagccgggtg | accattagtg | tcgacacttc | caaaaaccag | 300 |
| ttttcattga | gctctcaag | cgtaactgcg | gcggataccg | ccgtatacta | ttgtgcgcgg | 360 |
| ccacattacg | ggtcctctta | tgttggggcg | atggaatatt | gggggcagg | tacaacggtc | 420 |
| acggtgtctt | caggaggagg | agggtcaggt | ggtggtggtt | caggaggcgg | gggtagcgac | 480 |
| atacagatga | ctcaaagccc | ctcttcactg | tctgcatcag | tcggggacag | agtcacaata | 540 |
| acctgcagag | cgagcgagaa | tatctactct | tatgtagcct | ggtatcagca | aaaacccggc | 600 |
| aaggcgccga | aattgctcat | ctataatgcg | aaatccttgg | ccagtggggt | cccatcacgg | 660 |
| ttcagtggct | ccggctctgg | aaccgatttc | acactcacaa | tctctagcct | ccagcccgaa | 720 |
| gacttcgcca | catactattg | ccaacatcac | tatgtcagcc | catggacatt | tggggaggt | 780 |
| acgaaacttg | aaattaaact | cgagaagccc | accacgacgc | cagcgccgcg | accaccaaca | 840 |
| ccggcgccca | ccatcgcgtc | gcagcccctg | tccctgcgcc | cagaggcgag | ccggccagcg | 900 |
| gcgggggggcg | cagtgcacac | gagggggctg | gacttcgcca | gtgataagcc | ttttgggtg | 960 |
| ctggtggtgt | ttggtggagt | cctggcttgc | tatagcttgc | tagtaacagt | ggcctttatt | 1020 |
| attttctggg | tgaggagtaa | gaggagcagg | ctcctgcaca | gtgactacat | gaacatgact | 1080 |
| ccccgccgcc | ccgggcccac | ccgcaagcat | accagcccct | atgccccacc | acgcgacttc | 1140 |
| gcagcctatc | gctccagagt | gaagttcagc | aggagcgcag | acgcccccgc | gtaccagcag | 1200 |
| ggccagaacc | agctctataa | cgagctcaat | ctaggacgaa | gagaggagta | cgatgttttg | 1260 |
| gacaagagac | gtggccggga | ccctgagatg | ggggaaagc | cgcagagaag | gaagaaccct | 1320 |
| caggaaggcc | tgtacaatga | actgcagaaa | gataagatgg | cggaggccta | cagtgagatt | 1380 |
| gggatgaaag | gcgagcgccg | gaggggcaag | gggcacgatg | gcctttacca | gggtctcagt | 1440 |
| acagccacca | aggacaccta | cgacgccctt | cacatgcagg | ccctgccccc | tcgctaatag | 1500 |

<210> SEQ ID NO 25
<211> LENGTH: 498
<212> TYPE: PRT
<213> ORGANISM: Homo sapiens

<400> SEQUENCE: 25

Met Ala Leu Pro Val Thr Ala Leu Leu Leu Pro Leu Ala Leu Leu Leu

-continued

```
1               5                   10                  15
His Ala Ala Arg Pro Ala Ser Gln Val Gln Leu Gln Glu Ser Gly Pro
                20                  25                  30
Gly Leu Val Lys Pro Ser Glu Thr Leu Ser Leu Thr Cys Thr Val Ser
                35                  40                  45
Gly Gly Ser Ile Thr Ser Tyr Gly Val Ser Trp Ile Arg Gln Pro Pro
                50                  55                  60
Gly Lys Gly Leu Glu Trp Ile Gly Val Ile Trp Glu Asp Gly Ser Thr
65              70                  75                  80
Asn Tyr His Ser Ala Leu Ile Ser Arg Val Thr Ile Ser Val Asp Thr
                85                  90                  95
Ser Lys Asn Gln Phe Ser Leu Lys Leu Ser Ser Val Thr Ala Ala Asp
                100                 105                 110
Thr Ala Val Tyr Tyr Cys Ala Arg Pro His Tyr Gly Ser Ser Tyr Val
                115                 120                 125
Gly Ala Met Glu Tyr Trp Gly Ala Gly Thr Thr Val Thr Val Ser Ser
                130                 135                 140
Gly Gly Gly Gly Ser Gly Gly Gly Ser Gly Gly Gly Gly Ser Asp
145                 150                 155                 160
Ile Gln Met Thr Gln Ser Pro Ser Ser Leu Ser Ala Ser Val Gly Asp
                165                 170                 175
Arg Val Thr Ile Thr Cys Arg Ala Ser Glu Asn Ile Tyr Ser Tyr Val
                180                 185                 190
Ala Trp Tyr Gln Gln Lys Pro Gly Lys Ala Pro Lys Leu Leu Ile Tyr
                195                 200                 205
Asn Ala Lys Ser Leu Ala Ser Gly Val Pro Ser Arg Phe Ser Gly Ser
                210                 215                 220
Gly Ser Gly Thr Asp Phe Thr Leu Thr Ile Ser Ser Leu Gln Pro Glu
225                 230                 235                 240
Asp Phe Ala Thr Tyr Tyr Cys Gln His His Tyr Val Ser Pro Trp Thr
                245                 250                 255
Phe Gly Gly Gly Thr Lys Leu Glu Ile Lys Leu Glu Lys Pro Thr Thr
                260                 265                 270
Thr Pro Ala Pro Arg Pro Pro Thr Pro Ala Pro Thr Ile Ala Ser Gln
                275                 280                 285
Pro Leu Ser Leu Arg Pro Glu Ala Ser Arg Pro Ala Ala Gly Gly Ala
                290                 295                 300
Val His Thr Arg Gly Leu Asp Phe Ala Ser Asp Lys Pro Phe Trp Val
305                 310                 315                 320
Leu Val Val Val Gly Gly Val Leu Ala Cys Tyr Ser Leu Leu Val Thr
                325                 330                 335
Val Ala Phe Ile Ile Phe Trp Val Arg Ser Lys Arg Ser Arg Leu Leu
                340                 345                 350
His Ser Asp Tyr Met Asn Met Thr Pro Arg Arg Pro Gly Pro Thr Arg
                355                 360                 365
Lys His Tyr Gln Pro Tyr Ala Pro Pro Arg Asp Phe Ala Ala Tyr Arg
                370                 375                 380
Ser Arg Val Lys Phe Ser Arg Ser Ala Asp Ala Pro Ala Tyr Gln Gln
385                 390                 395                 400
Gly Gln Asn Gln Leu Tyr Asn Glu Leu Asn Leu Gly Arg Arg Glu Glu
                405                 410                 415
Tyr Asp Val Leu Asp Lys Arg Arg Gly Arg Asp Pro Glu Met Gly Gly
                420                 425                 430
```

Lys Pro Gln Arg Arg Lys Asn Pro Gln Glu Gly Leu Tyr Asn Glu Leu
            435                 440                 445

Gln Lys Asp Lys Met Ala Glu Ala Tyr Ser Glu Ile Gly Met Lys Gly
        450                 455                 460

Glu Arg Arg Arg Gly Lys Gly His Asp Gly Leu Tyr Gln Gly Leu Ser
465                 470                 475                 480

Thr Ala Thr Lys Asp Thr Tyr Asp Ala Leu His Met Gln Ala Leu Pro
                485                 490                 495

Pro Arg

<210> SEQ ID NO 26
<211> LENGTH: 121
<212> TYPE: PRT
<213> ORGANISM: Homo sapiens

<400> SEQUENCE: 26

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Ser Tyr
            20                  25                  30

Gly Val Ser Trp Ile Arg Gln Pro Pro Gly Lys Gly Leu Glu Trp Ile
        35                  40                  45

Gly Val Ile Trp Glu Asp Gly Ser Thr Asn Tyr His Ser Ala Leu Ile
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Pro His Tyr Gly Ser Ser Tyr Val Gly Ala Met Glu Tyr Trp Gly
            100                 105                 110

Ala Gly Thr Thr Val Thr Val Ser Ser
        115                 120

<210> SEQ ID NO 27
<211> LENGTH: 243
<212> TYPE: PRT
<213> ORGANISM: Homo sapiens

<400> SEQUENCE: 27

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Ser Tyr
            20                  25                  30

Gly Val Ser Trp Ile Arg Gln Pro Pro Gly Lys Gly Leu Glu Trp Ile
        35                  40                  45

Gly Val Ile Trp Glu Asp Gly Ser Thr Asn Tyr His Ser Ala Leu Ile
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Pro His Tyr Gly Ser Ser Tyr Val Gly Ala Met Glu Tyr Trp Gly
            100                 105                 110

Ala Gly Thr Thr Val Thr Val Ser Ser Gly Gly Gly Gly Ser Gly Gly
        115                 120                 125

Gly Gly Ser Gly Gly Gly Ser Asp Ile Gln Met Thr Gln Ser Pro
    130             135                 140

Ser Ser Leu Ser Ala Ser Val Gly Asp Arg Val Thr Ile Thr Cys Arg
145             150                 155                 160

Ala Ser Glu Asn Ile Tyr Ser Tyr Val Ala Trp Tyr Gln Gln Lys Pro
                165                 170                 175

Gly Lys Ala Pro Lys Leu Leu Ile Tyr Asn Ala Lys Ser Leu Ala Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
210                 215                 220

Gln His His Tyr Val Ser Pro Trp Thr Phe Gly Gly Gly Thr Lys Leu
225                 230                 235                 240

Glu Ile Lys

<210> SEQ ID NO 28
<211> LENGTH: 1500
<212> TYPE: DNA
<213> ORGANISM: Homo sapiens

<400> SEQUENCE: 28

```
atggccttac cagtgaccgc cttgctcctg ccgctggcct tgctgctcca cgccgccagg      60
ccggctagcc aggttcaatt gcaagaatca ggccctgggc ttgttaagcc gtcagagacg     120
ctttcactga cctgtaccgt gagcgggttc agcctcactt cctatggtgt ttcttggata     180
cgacaaccac ccggaaaggg cctggaatgg atcgggtca tttgggaaga tggatccaca     240
aactacaatc cttcacttaa atcccgagtt actatctctg ttgacaccag taaaaatcaa     300
ttcagtctca aactgtccag tgtgacagcc gccgacacag cagtctacta ttgcgctcgc     360
ccacattacg gctccagcta cgttggggcg atgaatattg ggggagctgg taccacagtc     420
acggttagta gtggaggagg tggttccggg ggagggggga gcggcggagg tggatctgat     480
atccagatga ctcagtctcc aagttcccctt tctgcaagcg taggtgatcg agtcactatc     540
acatgcaggg cgtccgagaa catatacagt tatgttgcat ggtaccaaca gaagccaggt     600
aaagcgccta agctgcttat ttataacgct aaatctcttg cttctggggt accatcccga     660
ttctcagggt ctggaagtgg cactgatttc acgttgacta tttcctccct tcaaccggag     720
gattttgcaa cgtactactg tcagcatcat tatgtcagcc cgtggacgtt cggtggcggc     780
acgaaacttg agattaaact cgagaagccc accacgacgc cagcgccgcg accaccaaca     840
ccggcgccca ccatcgcgtc gcagcccctg tccctgcgcc cagaggcgag ccggccagcg     900
gcggggggcg cagtgcacac gagggggctg gacttcgcca gtgataagcc cttttgggtg     960
ctggtggtgg ttggtggagt cctggcttgc tatagcttgc tagtaacagt ggcctttatt    1020
attttctggg tgaggagtaa gaggagcagg ctcctgcaca gtgactacat gaacatgact    1080
ccccgccgcc ccgggcccac cgcaagcat accagccct atgcccacc acgcgacttc    1140
gcagcctatc gctccagagt gaagttcagc aggagcgcag acgcccccgc gtaccagcag    1200
ggccagaacc agctctataa cgagctcaat ctaggacgaa gagaggagta cgatgttttg    1260
gacaagagac gtggccggga ccctgagatg gggggaaagc cgcagagaag gaagaaccct    1320
caggaaggcc tgtacaatga actgcagaaa gataagatgg cggaggccta cagtgagatt    1380
gggatgaaag gcgagcgccg gaggggcaag gggcacgatg gcctttacca gggtctcagt    1440
```

```
acagccacca aggacaccta cgacgccctt cacatgcagg ccctgccccc tcgctaatag    1500
```

<210> SEQ ID NO 29
<211> LENGTH: 498
<212> TYPE: PRT
<213> ORGANISM: Homo sapiens

<400> SEQUENCE: 29

Met Ala Leu Pro Val Thr Ala Leu Leu Leu Pro Leu Ala Leu Leu Leu
1               5                   10                  15

His Ala Ala Arg Pro Ala Ser Gln Val Gln Leu Gln Glu Ser Gly Pro
            20                  25                  30

Gly Leu Val Lys Pro Ser Glu Thr Leu Ser Leu Thr Cys Thr Val Ser
        35                  40                  45

Gly Phe Ser Leu Thr Ser Tyr Gly Val Ser Trp Ile Arg Gln Pro Pro
    50                  55                  60

Gly Lys Gly Leu Glu Trp Ile Gly Val Ile Trp Glu Asp Gly Ser Thr
65                  70                  75                  80

Asn Tyr Asn Pro Ser Leu Lys Ser Arg Val Thr Ile Ser Val Asp Thr
                85                  90                  95

Ser Lys Asn Gln Phe Ser Leu Lys Leu Ser Ser Val Thr Ala Ala Asp
            100                 105                 110

Thr Ala Val Tyr Tyr Cys Ala Arg Pro His Tyr Gly Ser Ser Tyr Val
        115                 120                 125

Gly Ala Met Glu Tyr Trp Gly Ala Gly Thr Thr Val Thr Val Ser Ser
    130                 135                 140

Gly Gly Gly Gly Ser Gly Gly Gly Ser Gly Gly Gly Gly Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Arg Ala Ser Glu Asn Ile Tyr Ser Tyr Val
            180                 185                 190

Ala Trp Tyr Gln Gln Lys Pro Gly Lys Ala Pro Lys Leu Leu Ile Tyr
        195                 200                 205

Asn Ala Lys Ser Leu Ala Ser Gly Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln His His Tyr Val Ser Pro Trp Thr
                245                 250                 255

Phe Gly Gly Gly Thr Lys Leu Glu Ile Lys Leu Glu Lys Pro Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Ser Arg Pro Ala Ala Gly Gly Ala
    290                 295                 300

Val His Thr Arg Gly Leu Asp Phe Ala Ser Asp Lys Pro Phe Trp Val
305                 310                 315                 320

Leu Val Val Val Gly Gly Val Leu Ala Cys Tyr Ser Leu Leu Val Thr
                325                 330                 335

Val Ala Phe Ile Ile Phe Trp Val Arg Ser Lys Arg Ser Arg Leu Leu
            340                 345                 350

His Ser Asp Tyr Met Asn Met Thr Pro Arg Arg Pro Gly Pro Thr Arg
        355                 360                 365

Lys His Tyr Gln Pro Tyr Ala Pro Arg Asp Phe Ala Ala Tyr Arg
        370             375             380

Ser Arg Val Lys Phe Ser Arg Ser Ala Asp Ala Pro Ala Tyr Gln Gln
385             390             395             400

Gly Gln Asn Gln Leu Tyr Asn Glu Leu Asn Leu Gly Arg Arg Glu Glu
                405             410             415

Tyr Asp Val Leu Asp Lys Arg Gly Arg Asp Pro Glu Met Gly Gly
            420             425             430

Lys Pro Gln Arg Arg Lys Asn Pro Gln Glu Gly Leu Tyr Asn Glu Leu
                435             440             445

Gln Lys Asp Lys Met Ala Glu Ala Tyr Ser Glu Ile Gly Met Lys Gly
450             455             460

Glu Arg Arg Arg Gly Lys Gly His Asp Gly Leu Tyr Gln Gly Leu Ser
465             470             475             480

Thr Ala Thr Lys Asp Thr Tyr Asp Ala Leu His Met Gln Ala Leu Pro
                485             490             495

Pro Arg

<210> SEQ ID NO 30
<211> LENGTH: 121
<212> TYPE: PRT
<213> ORGANISM: Homo sapiens

<400> SEQUENCE: 30

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val Ser Trp Ile Arg Gln Pro Pro Gly Lys Gly Leu Glu Trp Ile
        35                  40                  45

Gly Val Ile Trp Glu Asp Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Pro His Tyr Gly Ser Ser Tyr Val Gly Ala Met Glu Tyr Trp Gly
            100                 105                 110

Ala Gly Thr Thr Val Thr Val Ser Ser
        115                 120

<210> SEQ ID NO 31
<211> LENGTH: 243
<212> TYPE: PRT
<213> ORGANISM: Homo sapiens

<400> SEQUENCE: 31

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val Ser Trp Ile Arg Gln Pro Pro Gly Lys Gly Leu Glu Trp Ile
        35                  40                  45

Gly Val Ile Trp Glu Asp Gly Ser Thr Asn Tyr Asn Pro Ser Leu Lys
    50                  55                  60

Ser Arg Val Thr Ile Ser Val Asp Thr Ser Lys Asn Gln Phe Ser Leu

-continued

```
                65                  70                  75                  80
Lys Leu Ser Ser Val Thr Ala Ala Asp Thr Ala Val Tyr Tyr Cys Ala
                    85                  90                  95

Arg Pro His Tyr Gly Ser Ser Tyr Val Gly Ala Met Glu Tyr Trp Gly
                100                 105                 110

Ala Gly Thr Thr Val Thr Val Ser Gly Gly Gly Ser Gly Gly
            115                 120                 125

Gly Gly Ser Gly Gly Gly Ser Asp Ile Gln Met Thr Gln Ser Pro
        130                 135                 140

Ser Ser Leu Ser Ala Ser Val Gly Asp Arg Val Thr Ile Thr Cys Arg
145                 150                 155                 160

Ala Ser Glu Asn Ile Tyr Ser Tyr Val Ala Trp Tyr Gln Gln Lys Pro
                165                 170                 175

Gly Lys Ala Pro Lys Leu Leu Ile Tyr Asn Ala Lys Ser Leu Ala Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln His His Tyr Val Ser Pro Trp Thr Phe Gly Gly Gly Thr Lys Leu
225                 230                 235                 240

Glu Ile Lys
```

<210> SEQ ID NO 32
<211> LENGTH: 729
<212> TYPE: DNA
<213> ORGANISM: Homo sapiens

<400> SEQUENCE: 32

```
caggtccagc tgcaagaatc aggaccagga ctggtaaagc cgtccgaaac gctcagtttg      60
acgtgcaccg tgtcaggcgg cagtataaca tcctacgggg tcagctggat ccgccaaccg     120
cctgggaaag gcctcgaatg gataggggtg atttggaag acgggagtac aaactacaat     180
ccgagtttga agagccgcgt gacgataagc gttgacacaa gtaagaacca gtttagtctc     240
aaactctcca gtgtaacagc tgctgataca gcagtgtact actgcgctcg acctcactat     300
ggctctagtt acgtcggagc tatggaatac tgggggctg gcactacagt tactgtgagt     360
tccggtggcg gaggatctgg tggcggtggt tccggtgggg aggatccga catacagatg     420
acgcagtccc caagtagctt gagcgcatca gtaggagaca gagtcaccat tacatgccga     480
gcttccgaga acatctacag ttacgtagct tggtatcagc aaaaaccggg aaagcacct     540
aaacttctca tctacaacgc aaaaagtctg gcgagtgggg ttccctcaag gttctctgga     600
agcgggagcg gaacggattt tactctgact attagtagtt tgcaaccaga gactttgcc     660
acgtactact gtcagcatca ctatgtctcc ccttggacgt tcggaggagg gaccaagctc     720
gaaatcaaa                                                            729
```

<210> SEQ ID NO 33
<211> LENGTH: 498
<212> TYPE: PRT
<213> ORGANISM: Homo sapiens

<400> SEQUENCE: 33

```
Met Ala Leu Pro Val Thr Ala Leu Leu Leu Pro Leu Ala Leu Leu Leu
1               5                   10                  15
```

```
His Ala Ala Arg Pro Ala Ser Gln Val Gln Leu Gln Glu Ser Gly Pro
             20                  25                  30
Gly Leu Val Lys Pro Ser Glu Thr Leu Ser Leu Thr Cys Thr Val Ser
             35                  40                  45
Gly Gly Ser Ile Thr Ser Tyr Gly Val Ser Trp Ile Arg Gln Pro Pro
     50                  55                  60
Gly Lys Gly Leu Glu Trp Ile Gly Val Ile Trp Glu Asp Gly Ser Thr
65                  70                  75                  80
Asn Tyr Asn Pro Ser Leu Lys Ser Arg Val Thr Ile Ser Val Asp Thr
                 85                  90                  95
Ser Lys Asn Gln Phe Ser Leu Lys Leu Ser Ser Val Thr Ala Ala Asp
            100                 105                 110
Thr Ala Val Tyr Tyr Cys Ala Arg Pro His Tyr Gly Ser Ser Tyr Val
        115                 120                 125
Gly Ala Met Glu Tyr Trp Gly Ala Gly Thr Thr Val Thr Val Ser Ser
        130                 135                 140
Gly Gly Gly Gly Ser Gly Gly Gly Ser Gly Gly Gly Gly Ser Asp
145                 150                 155                 160
Ile Gln Met Thr Gln Ser Pro Ser Ser Leu Ser Ala Ser Val Gly Asp
                165                 170                 175
Arg Val Thr Ile Thr Cys Arg Ala Ser Glu Asn Ile Tyr Ser Tyr Val
            180                 185                 190
Ala Trp Tyr Gln Gln Lys Pro Gly Lys Ala Pro Lys Leu Leu Ile Tyr
        195                 200                 205
Asn Ala Lys Ser Leu Ala Ser Gly Val Pro Ser Arg Phe Ser Gly Ser
210                 215                 220
Gly Ser Gly Thr Asp Phe Thr Leu Thr Ile Ser Ser Leu Gln Pro Glu
225                 230                 235                 240
Asp Phe Ala Thr Tyr Tyr Cys Gln His His Tyr Val Ser Pro Trp Thr
                245                 250                 255
Phe Gly Gly Gly Thr Lys Leu Glu Ile Lys Leu Glu Lys Pro Thr Thr
            260                 265                 270
Thr Pro Ala Pro Arg Pro Pro Thr Pro Ala Pro Thr Ile Ala Ser Gln
        275                 280                 285
Pro Leu Ser Leu Arg Pro Glu Ala Ser Arg Pro Ala Ala Gly Gly Ala
        290                 295                 300
Val His Thr Arg Gly Leu Asp Phe Ala Ser Asp Lys Pro Phe Trp Val
305                 310                 315                 320
Leu Val Val Val Gly Gly Val Leu Ala Cys Tyr Ser Leu Leu Val Thr
                325                 330                 335
Val Ala Phe Ile Ile Phe Trp Val Arg Ser Lys Arg Ser Arg Leu Leu
            340                 345                 350
His Ser Asp Tyr Met Asn Met Thr Pro Arg Arg Pro Gly Pro Thr Arg
        355                 360                 365
Lys His Tyr Gln Pro Tyr Ala Pro Pro Arg Asp Phe Ala Ala Tyr Arg
        370                 375                 380
Ser Arg Val Lys Phe Ser Arg Ser Ala Asp Ala Pro Ala Tyr Gln Gln
385                 390                 395                 400
Gly Gln Asn Gln Leu Tyr Asn Glu Leu Asn Leu Gly Arg Arg Glu Glu
                405                 410                 415
Tyr Asp Val Leu Asp Lys Arg Gly Arg Asp Pro Glu Met Gly Gly
            420                 425                 430
Lys Pro Gln Arg Arg Lys Asn Pro Gln Glu Gly Leu Tyr Asn Glu Leu
```

```
            435                 440                 445
Gln Lys Asp Lys Met Ala Glu Ala Tyr Ser Glu Ile Gly Met Lys Gly
        450                 455                 460

Glu Arg Arg Arg Gly Lys Gly His Asp Gly Leu Tyr Gln Gly Leu Ser
465                 470                 475                 480

Thr Ala Thr Lys Asp Thr Tyr Asp Ala Leu His Met Gln Ala Leu Pro
                485                 490                 495

Pro Arg

<210> SEQ ID NO 34
<211> LENGTH: 121
<212> TYPE: PRT
<213> ORGANISM: Homo sapiens

<400> SEQUENCE: 34

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Ser Tyr
            20                  25                  30

Gly Val Ser Trp Ile Arg Gln Pro Pro Gly Lys Gly Leu Glu Trp Ile
        35                  40                  45

Gly Val Ile Trp Glu Asp Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Pro His Tyr Gly Ser Ser Tyr Val Gly Ala Met Glu Tyr Trp Gly
            100                 105                 110

Ala Gly Thr Thr Val Thr Val Ser Ser
        115                 120

<210> SEQ ID NO 35
<211> LENGTH: 243
<212> TYPE: PRT
<213> ORGANISM: Homo sapiens

<400> SEQUENCE: 35

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Ser Tyr
            20                  25                  30

Gly Val Ser Trp Ile Arg Gln Pro Pro Gly Lys Gly Leu Glu Trp Ile
        35                  40                  45

Gly Val Ile Trp Glu Asp Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Pro His Tyr Gly Ser Ser Tyr Val Gly Ala Met Glu Tyr Trp Gly
            100                 105                 110

Ala Gly Thr Thr Val Thr Val Ser Ser Gly Gly Gly Gly Ser Gly Gly
        115                 120                 125

Gly Gly Ser Gly Gly Gly Gly Ser Asp Ile Gln Met Thr Gln Ser Pro
    130                 135                 140
```

```
Ser Ser Leu Ser Ala Ser Val Gly Asp Arg Val Thr Ile Thr Cys Arg
145                 150                 155                 160

Ala Ser Glu Asn Ile Tyr Ser Tyr Val Ala Trp Tyr Gln Gln Lys Pro
                165                 170                 175

Gly Lys Ala Pro Lys Leu Leu Ile Tyr Asn Ala Lys Ser Leu Ala Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln His His Tyr Val Ser Pro Trp Thr Phe Gly Gly Gly Thr Lys Leu
225                 230                 235                 240

Glu Ile Lys
```

PLAP-CAR-EFFECTOR CELLS

This application is a continuation of PCT/US2019/033953, filed May 24, 2019; which claims the priority of U.S. Provisional Applications No. 62/683,999, filed Jun. 12, 2018, and 62/792,344, filed Jan. 14, 2019. The contents of the above-identified applications are incorporated herein by reference in their entireties.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of May 23, 2019, and a size of 66,100 bytes. The Sequence Listing filed via EFS-Web is part of the specification and is hereby incorporated in its entirety by reference herein.

FIELD OF THE INVENTION

The present invention relates to PLAP (placental alkaline phosphatase)-CAR. The present invention is also directed to a method for treating PLAP-positive cancer cells by administering PLAP-CAR-T cells, PLAP-CAR-natural killer cells, or PLAP-CAR-macrophages to the patients.

BACKGROUND OF THE INVENTION

Immunotherapy is emerging as a highly promising approach for the treatment of cancer. T cells or T lymphocytes, the armed forces of our immune system, constantly look for foreign antigens and discriminate abnormal (cancer or infected cells) from normal cells. Genetically modifying T cells with CARs is the most common approach to design tumor-specific T cells. CAR-T cells targeting tumor-associated antigens (TAA) can be infused into patients (called adoptive cell transfer or ACT) representing an efficient immunotherapy approach. The advantage of CAR-T technology compared with chemotherapy or antibody is that reprogrammed engineered T cells can proliferate and persist in the patient ("a living drug").

CARs (Chimeric antigen receptors) usually consist of a monoclonal antibody-derived single-chain variable fragment (scFv) linked by a hinge and transmembrane domain to a variable number of intracellular signaling co-stimulatory domains: (i) CD28, Ox-40, CD137 (4-1BB), GITR or other co-stimulatory domains; and (ii) a single, cellular activating, CD3-zeta domain after co-stimulatory domains (FIG. 1). The evolution of CARs went from first generation (with no co-stimulatory domains) to second generation (with one co-stimulatory domain) to third generation CAR (with several co-stimulatory domains). Generating CARs with multiple costimulatory domains (the so-called $3^{rd}$ generation CAR) have led to increased cytolytic activity, and significantly improved persistence of CAR-T cells that demonstrate augmented antitumor activity.

Natural-killer (NK) cells are CD56+CD3− large granular lymphocytes that can kill virally infected and transformed cells, and constitute a critical cellular subset of the innate immune system. Unlike cytotoxic CD8+T lymphocytes, NK cells launch cytotoxicity against tumor cells without the requirement for prior sensitization, and can also eradicate MHC-I negative cells.

CAR-T cell therapy had successful clinical results in the treatment of hematological cancer patients [1-5]. Chimeric antigen receptor contains single chain fragment variant (ScFv) of antibody targeting cancer cell surface antigen fused to a hinge, transmembrane domain, co-stimulatory (CD28, 41-BB or other domains) and CD3 activation domain [1,6],[7,8]. Recently two CD19-CAR-T cell therapies (Kymriah and Yescarta) were approved by FDA for the treatment of hematological cancers based on their high response rate in acute lymphoblastic leukemia and other hematological cancers in clinical trials [3], [9-11]. There are also several other CAR-T cells that are tested in clinical trials such as CD22-CAR-T cells [12] for B-cell lymphoma, BCMA-CAR-T cells for multiple myeloma [13-14].

In terms of solid tumors, CAR-T cell therapy still has many challenges for targeting solid cancers due to on-target off-tumor effects, suppressive tumor microenvironment, decreased CAR-T cell access to the tumor, T cell exhaustion and low persistency [15], [16-18]. The main challenge with CAR-T cells targeting solid tumors is that most tumor solid tumor antigens are expressed in normal tissues.

PLAP

PLAP is a placental alkaline phosphatase that is encoded by ALPP gene. PLAP is a metalloenzyme enzyme that catalyzes the hydrolysis of phosphoric acid monoesters. PLAP is expressed mainly in placental and endometrial tissues, it is not expressed in normal tissues.

PLAP has high expression in placenta [19], and it is not expressed in most normal tissues except of testis [20]. It was found to be overexpressed in malignant seminoma, teratoma [20], [21], ovarian and cervical carcinoma [22], [23], [24], and colon adenocarcinoma [25]. PLAP was detected in lung, pancreas, stomach tumors [39]. PLAP was also detected among several other membrane-bound proteins in exosomes of non-small cell lung cancer patients with a potential to be prognostic marker [26].

Human PLAP is a 535 amino-acid glycosylated protein encoded by ALPP gene with 1-22 signaling peptide, then extracellular domain (23-506), 513-529 transmembrane domain (sequence is shown below, transmembrane domain is underlined) Uniprot database (www.uniprot.org/uniprot/P05187; NM_001632). Its sequence is shown below (SEQ ID NO: 1).

```
         10         20         30         40
MLGPCMLLLL LLLGLRLQLS LGTIPVEEEN PDFWNREAAE 50         60         70         80
ALGAAKKLQP AQTAAKNLII FLGDGMGVST VTAARILKGQ 90        100        110        120
KKDKLGPEIP LAMDRFPYVA LSKTYNVDKH VPDSGATATA 130        140        150        160
YLCGVKGNFQ TIGLSAAARF NQCNTTRGNE VISVMNRAKK 170        180        190        200
AGKSVGVVTT TRVQHASPAG TYAHTVNRNW YSDADVPASA 210        220        230        240
RQEGCQDIAT QLISNMDIDV ILGGGRKYMF RMGTPDPEYP 250        260        270        280
DDYSQGGTRL DGKNLVQEWL ARKQGARYVW NRTELMQASL 290        300        310        320
DPSVTHLMGL FEPGDMKYEI HRDSTLDPSL MEMTEAALRL 330        340        350        360
LSRNPRGFFL FVEGGRIDHG HHESRAYRAL TETIMFDDAI
```

```
         370         380         390         400
    ERAGQLTSEE DTLSLVTADH SHVFSFGGYP LRGSSIFGLA 410         420         430         440
    PGKARDRKAY TVLLYGNGPG YVLKDGARPD VTESESGSPE 450         460         470         480
    YRQQSAVPLD EETHAGEDVA VFARGPQAHL VHGVQEQTFI 490         500         510         520
    AHVMAFAACL EPYTACDLAP PAGTTDAAHP GRSVVPALLP

530
    LLAGTLLLLE TATAP
```

There are four distinct but related alkaline phosphatases: intestinal (ALPI) (NM_001631); placental; placental-like (ALPPL2) (NM_031313) which are all encoded by gene on at chromosome 2 and liver/bone/kidney (ALPL) (tissue-nonspecific) (NM_000478) encoded by gene on chromosome 1.

BRIEF DESCRIPTION OF THE DRAWINGS

FIGS. 6C(1) and 6C(2) show quantification of real-time cytotoxicity as described in Materials and Methods. Humanized PLAP-CAR-T specifically killed PALP-positive colon cancer cells, but not PALP-negative colon cancer cells. P<0.06, Student's t-test, increased cytotoxicity of PLAP-CAR-T cells versus Mock-CAR-T cells. FIGS. 6D(1) and 6D(2) show that PLAP-CAR-T cells secreted significant level of IFN-gamma, IL-2 and IL-6 versus Mock-CAR-T cells against PLAP-positive colon cancer cell lines and not against PLAP-negative colon cancer cell lines. p<0.05, Student's t-test.

FIGS. 8A(1)-8A(3) show that PLAP h5-CAR-T cells significantly killed PLAP-positive colon cancer cells (Caco-2 cells and Lovo cells), but not PLAP-negative colon cancer cells (HCT116).

FIG. 9A is the quantification of FACS data, which shows the PDL-1 expression in colon cancer cell lines before and after PLAP-CAR-T-treatment by FACS analysis. Addition of IFN-gamma (20/ng/ml) was used as a positive control for PDL-1 induction. PLAP-positive Lovo cells significantly induced PDL-1 expression compared with T and Mock-CAR-T cells in response to hPLAP-CAR-T cells while Caco-2, HCT116, HT29 cells did not. FIG. 9B shows the response of PDL-1 up-regulation to different doses of CAR-T cells. FIG. 9C shows the time and dose-dependent induction of PDL-1 in Lovo cancer cells induced by hPLAP-CAR-T cells.

DETAILED DESCRIPTION OF THE INVENTION

Definitions

Figure 1:
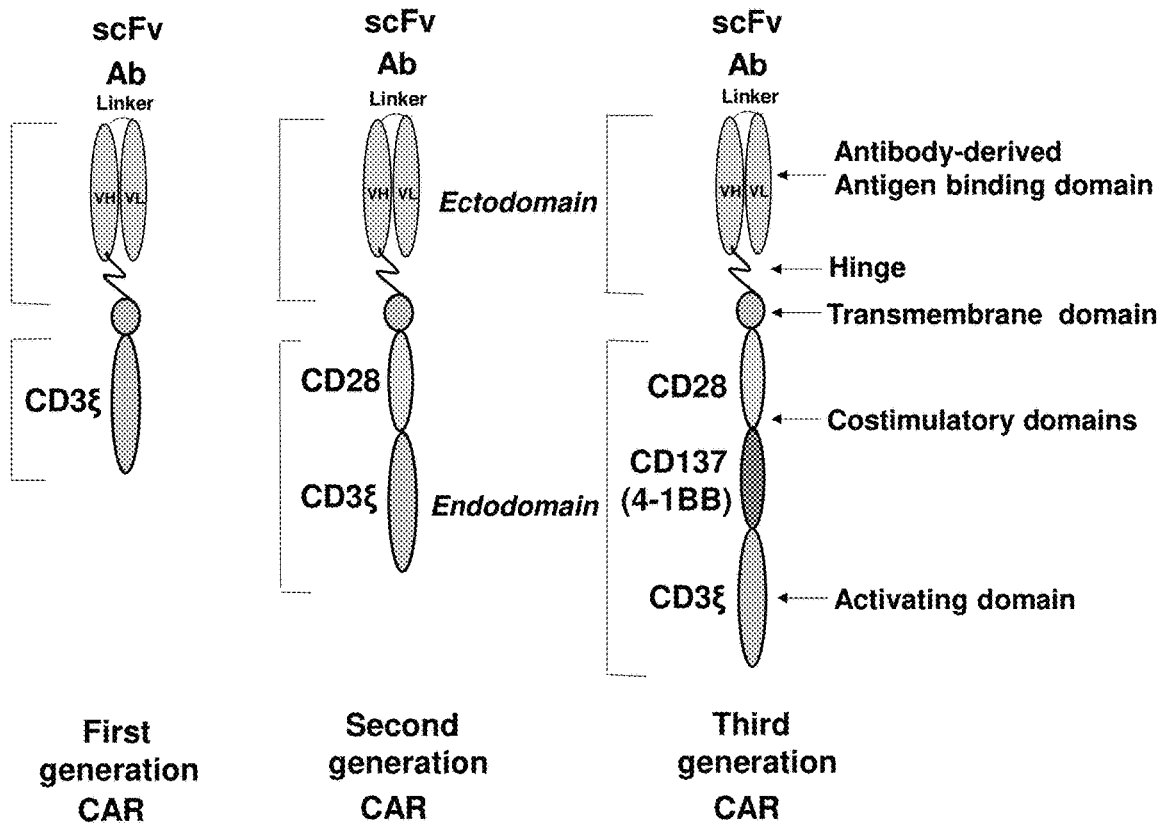
FIG. 1 shows the structure of CAR. On the left panel: the structure of first generation (no co-stimulation domains), on the middle panel: second generation (one co-stimulation domain CD28 or 4-BB) and on the right panel: third generation of CAR (two or several co-stimulation domains) are shown [7].

As used herein, "adoptive cell therapy" (ACT) is a treatment that uses a cancer patient's own T lymphocytes, or NK cells, or other hematopoietic cells such as macrophages, induced pluripotent cells, with anti-tumor activity, expanded in vitro and reinfused into the patient with cancer.

As used herein, "affinity" is the strength of binding of a single molecule to its ligand. Affinity is typically measured and reported by the equilibrium dissociation constant ($K_D$ or Kd), which is used to evaluate and rank order strengths of bimolecular interactions.

As used herein, a "chimeric antigen receptor (CAR)" means a fused protein comprising an extracellular domain capable of binding to an antigen, a transmembrane domain derived from a polypeptide different from a polypeptide from which the extracellular domain is derived, and at least one intracellular domain. The "chimeric antigen receptor (CAR)" is sometimes called a "chimeric receptor", a "T-body", or a "chimeric immune receptor (CIR)." The "extracellular domain capable of binding to an antigen" means any oligopeptide or polypeptide that can bind to a certain antigen. The "intracellular domain" means any oligopeptide or polypeptide known to function as a domain that transmits a signal to cause activation or inhibition of a biological process in a cell.

As used herein, a "domain" means one region in a polypeptide which is folded into a particular structure independently of other regions.

As used herein, a "single chain variable fragment (scFv)" means a single chain polypeptide derived from an antibody which retains the ability to bind to an antigen. An example of the scFv includes an antibody polypeptide which is formed by a recombinant DNA technique and in which Fv regions of immunoglobulin heavy chain (H chain) and light chain (L chain) fragments are linked via a spacer sequence. Various methods for preparing an scFv are known to a person skilled in the art.

As used herein, a "tumor antigen" means a biological molecule having antigenicity, expression of which causes cancer.

The inventors have discovered that PLAP is a unique tumor marker and that PLAP can be advantageously used to prepare PLAP-CAR T cells or PLAP-NK cells, which can be used for CAR-T cell therapy or CAR-NK cell therapy, because PLAP is not expressed in normal tissues. Unlike other tumor markers that are expressed in low levels in normal tissues, the advantage of PLAP target not expressed in most normal tissues but only in placenta and testis is that PLAP-CAR-T cells/PLAP-NK cells do not react against normal tissues and thus they are safe and have low toxicity.

The present invention provides CAR-T cells and NK cells that target PLAP tumor antigen which is highly overexpressed in many types of cancer such as ovarian, seminoma, and colon cancer. The PLAP-CAR-T cells and PLAP-NK cells of the present invention have high cytotoxic activity against several cancer cells: colon and ovarian cancer cell lines.

The present invention is directed to a chimeric antigen receptor fusion protein comprising from N-terminus to C-terminus: (i) a single-chain variable fragment (scFv) comprising $V_H$ and $V_L$, wherein scFv binds to human PLAP, (ii) a transmembrane domain, (iii) a co-stimulatory domain of CD28, and (iv) an activating domain.

In one embodiment, the PLAP antibody is a mouse antibody, and $V_H$ has the amino acid sequence of SEQ ID NO: 5 and $V_L$ has the amino acid sequence of SEQ ID NO: 6.

In one embodiment, the PLAP antibody is a humanized antibody, and $V_H$ has the amino acid sequence of SEQ ID NO: 16, 21, 26, 30, or 34, and $V_L$ has the amino acid sequence of SEQ ID NO: 22.

In one embodiment, the scFv comprises the amino acid sequence of SEQ ID NO: 8, 18, 23, 27, 31, or 35; or an amino acid sequence having at least 95%, 96%, 97%, 98%, or 99% sequence identity thereof, provided that the sequence variation is in the non-CDR framework regions.

In one embodiment, the CAR comprises the amino acid sequence of SEQ ID NO: 5, 15, 20, 25, 29, or 33; or an amino acid sequence having at least 95%, 96%, 97%, 98%, or 99% sequence identity thereof, provided that the sequence variation is not in the CDR regions.

The sequence variation, i.e., the amino acid changes are preferably of a minor amino acid change such as a conservative amino acid substitution. A conservative amino acid substitution is well-known to a person skilled in the art.

The present invention is directed to an adoptive cell therapy method for treating cancer, comprising the step of administering PLAP CAR-T cells, PLAP CAR-NK cells, or PLAP CAR-macrophages to a subject suffering from cancer, wherein the cancer is selected from the group consisting of colon cancer, lung cancer, pancreatic cancer, stomach cancer, testicular cancer, teratoma, seminoma, ovarian cancer, and cervical cancer, and the cancer is PLAP-positive.

Suitable antibody useful for PLAP CAR includes mouse PLAP antibody against PLAP and humanized PLAP antibody against PLAP. In one embodiment, the antibody has a high affinity against PLAP.

The CAR of the present invention comprises a single chain variable fragment (scFv) that binds specifically to PLAP. The heavy chain (H chain) and light chain (L chain) fragments of an anti-PLAP antibody are linked via a linker sequence. For example, a linker can be 5-20 amino acids. The scFv structure can be VL-linker-VH, or VH-linker-VL, from N-terminus to C-terminus.

The CAR of the present invention comprises a transmembrane domain which spans the membrane. The transmembrane domain may be derived from a natural polypeptide, or may be artificially designed. The transmembrane domain derived from a natural polypeptide can be obtained from any membrane-binding or transmembrane protein. For example, a transmembrane domain of a T cell receptor α or β chain, a CD3 zeta chain, CD28, CD3-epsilon, CD45, CD4, CD5, CD8, CD9, CD16, CD22, CD33, CD37, CD64, CD80, CD86, CD134, CD137, ICOS, CD154, or a GITR can be used. The artificially designed transmembrane domain is a polypeptide mainly comprising hydrophobic residues such as leucine and valine. It is preferable that a triplet of phenylalanine, tryptophan and valine is found at each end of the synthetic transmembrane domain. In preferred embodiments, the transmembrane domain is derived from CD28 or CD8, which give good receptor stability.

In the present invention, the co-stimulatory domain is selected from the group consisting of human CD28, 4-1BB (CD137), ICOS-1, CD27, OX 40 (CD137), DAP10, and GITR (AITR).

The endodomain (the activating domain) is the signal-transmission portion of the CAR. After antigen recognition, receptors cluster and a signal is transmitted to the cell. The most commonly used endodomain component is that of CD3-zeta (CD3 Z or CD3ζ), which contains 3 ITAMs. This transmits an activation signal to the T cell after antigen is bound. CD3-zeta may not provide a fully competent activation signal and additional co-stimulatory signaling may be needed. For example, one or more co-stimulating domains can be used with CD3-Zeta to transmit a proliferative/survival signal.

The CAR of the present invention may comprise a signal peptide N-terminal to the ScFv so that when the CAR is expressed inside a cell, such as a T-cell, NK cells, or macrophages, the nascent protein is directed to the endoplasmic reticulum and subsequently to the cell surface, where it is expressed. The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases. As an example, the signal peptide may derive from human CD8 or GM-CSF, or a variant thereof having 1 or 2 amino acid mutations provided that the signal peptide still functions to cause cell surface expression of the CAR.

The CAR of the present invention may comprise a spacer sequence as a hinge to connect scFv with the transmembrane domain and spatially separate antigen binding domain from the endodomain. A flexible spacer allows to the binding domain to orient in different directions to enable its binding to a tumor antigen. The spacer sequence may, for example, comprise an IgG1 Fc region, an IgG1 hinge or a CD8 stalk, or a combination thereof. A human CD28 or CD8 stalk is preferred.

The present invention provides a nucleic acid encoding the CAR described above. The nucleic acid encoding the CAR can be prepared from an amino acid sequence of the specified CAR by a conventional method. A base sequence encoding an amino acid sequence can be obtained from the aforementioned NCBI RefSeq IDs or accession numbers of GenBenk for an amino acid sequence of each domain, and the nucleic acid of the present invention can be prepared using a standard molecular biological and/or chemical procedure. For example, based on the base sequence, a nucleic acid can be synthesized, and the nucleic acid of the present invention can be prepared by combining DNA fragments which are obtained from a cDNA library using a polymerase chain reaction (PCR).

The nucleic acid encoding the CAR of the present invention can be inserted into a vector, and the vector can be introduced into a cell. For example, a virus vector such as a retrovirus vector (including an oncoretrovirus vector, a lentivirus vector, and a pseudo type vector), an adenovirus vector, an adeno-associated virus (AAV) vector, a simian virus vector, a vaccinia virus vector or a Sendai virus vector, an Epstein-Barr virus (EBV) vector, and a HSV vector can be used. As the virus vector, a virus vector lacking the replicating ability so as not to self-replicate in an infected cell is preferably used.

For example, when a retrovirus vector is used, the process of the present invention can be carried out by selecting a suitable packaging cell based on a LTR sequence and a packaging signal sequence possessed by the vector and preparing a retrovirus particle using the packaging cell. Examples of the packaging cell include PG13 (ATCC CRL-10686), PA317 (ATCC CRL-9078), GP+E-86 and GP+en-vAm-12, and Psi-Crip. A retrovirus particle can also be prepared using a 293 cell or a 293T cell having high transfection efficiency. Many kinds of retrovirus vectors produced based on retroviruses and packaging cells that can be used for packaging of the retrovirus vectors are widely commercially available from many companies.

The present invention provides T cells, or NK cells, or macrophages, modified to express the chimeric antigen receptor fusion protein as described above. CAR-T cells, CAR-NK cells, or CAR-macrophages of the present invention bind to a specific antigen via the CAR, thereby a signal is transmitted into the cell, and as a result, the cell is activated. The activation of the cell expressing the CAR is varied depending on the kind of a host cell and an intracellular domain of the CAR, and can be confirmed based on, for example, release of a cytokine, improvement of a cell proliferation rate, change in a cell surface molecule, or the like as an index.

T cells, or NK cells, or macrophages, modified to express the CAR can be used as a therapeutic agent for a disease. The therapeutic agent comprises the T cells expressing the CAR as an active ingredient, and may further comprise a suitable excipient. Examples of the excipient include pharmaceutically acceptable excipients known to a person skilled in the art.

This application demonstrates the efficacy of CAR-T cells targeting PLAP antigen that is overexpressed in colon cancer tumors. This application demonstrates that PLAP-CAR-T cells specifically decreases viability of PLAP-positive colon cancer cells but not PLAP-negative cancer cells. PLAP-CAR-T cells secrets significant level of IFN-gamma after co-incubation with PLAP-positive colon cancer cells but not after co-incubation with PLAP-negative cancer cells. This application demonstrates that PLAP-CAR-T cells significantly decreases Lovo (positive PLAP-colon cancer cells) xenograft tumor growth in vivo. There are no increase of AST, ALT or amylase enzyme levels in mouse blood and no decrease of mouse body weight after treating mice with hPLAP-CAR-T cells demonstrating no toxic effect of hPLAP-CAR-T cells in vivo. In addition, combination of hPLAP-CAR-T cells with PD-1 or LAG-3 antibodies increased efficacy of CAR-T cells against colon cancer cells.

The inventors found that PLAP-CAR-T cells significantly killed all PLAP-positive cancer cells, and did not kill PLAP-negative colon cancers. This implies high specificity of PLAP-CAR-T cells. In addition, Lovo and Caco-2 colon cancer cells differed in up-regulation of PDL-1 by CAR-T cells. Lovo colon cancer cell induced PDL-1 in response to PLAP-CAR-T cells, while Caco-2 cells did not. Both of cell lines were effectively killed by hPLAP-CAR-T cells independently of induction of PDL-1 expression. The humanized PLAP-CAR-T cells killed faster Lovo cells than Caco-2 cells and secreted more IFN-gamma against Lovo colon cancer cells than against Caco-2 cells. In addition, T cells and Mock CAR-T cells had more activity in Lovo cells that in Caco-2 cells. This show that hPLAP-CAR-T cells can overcome PDL-1 up-regulation in Lovo cells. This was shown when Lovo cells were pretreated with IFN-gamma to up-regulate PDL-1, PLAP-CAR-T cells effectively killed Lovo cells. Colon cancer with Kras mutations were shown to be resistant to therapies such as Cetuximab (ERBITUX®, monoclonal antibody) [40], while hPLAP-CAR-T cells effectively killed two different colon cancer cell lines: Lovo (codon 13 mutation: G13D) and LS123 (codon 12 mutation: G12D). This is another advantage of hPLAP-CAR-T cells against solid tumors with Kras mutations responsible for resistance to other therapies.

PLAP-CAR-T cells up-regulated PD-1 and LAG-3 after co-culturing with PLAP-positive colon cancer cell lines but did not increase with PLAP-negative colon cancer cell lines. The inventors have found dose-dependent up-regulation of PDL-1 in response to PLAP-CAR-T cells in Lovo colon cancer cell lines. PD-1, PDL-1 or LAG-3 antibody in combination with PLAP-CAR-T cells significantly increased CAR-T induced cytotoxicity and IFN-gamma secretion against Lovo cancer cells. Thus, checkpoint inhibitors can decrease exhaustion of CAR-T cells and provide basis for combination therapy.

PLAP scFv-(CD28, OX-40, 4-1BB, or GITR)-CD3 zeta CAR-T cells, CAR-NK cells, or CAR-macrophages can be used in combination with different chemotherapy: checkpoint inhibitors; targeted therapies, small molecule inhibitors, and antibodies.

Tags (Flag tag or other tags) conjugated PLAP scFv can be used for CAR generation.

Third generation CAR-T or other co-activation signaling domains can be used for the PLAP-scFv inside CAR.

Bispecific PLAP- and other antigens (EGFR, HER-2, VEGFR, NGFR) CAR-T cells, CAR-NK cells, or CAR-macrophages can be used for immunotherapy. The construct of the bispecific CAR-T cells contain a first scFv against PLAP, and a second scFv against a second tumor antigen. CAR-T cells with bispecific antibody can target cancer cells that overexpress two tumor antigens more effectively and specifically.

Combination of PLAP-CAR-T cells, CAR-NK cells, or CAR-macrophages with CAR-T cells, CAR-NK cells, or CAR-macrophages targeting other tumor antigens or tumor microenvironment (e.g. VEGFR-1-3), i.e., dual CAR-T cells, CAR-NK cells, or CAR-macrophages, can be used to enhance activity of monotherapy PLAP-CAR.

PLAP-CAR-T cells, CAR-NK cells, or CAR-macrophages can be used to activate phagocytosis and block "don't eat" signaling.

PLAP-CAR-NK cells are safe effector cells, as they may avoid the potentially lethal complications of cytokine storms, tumor lysis syndrome, and on-target, off-tumor effects.

Anti-PLAP antibody h2, h4 and h5 VH and VL sequences can be used as one arm of a bi-specific antibody.

Both PLAP-CAR-T cells and bi-specific antibodies containing anti-PLAP VH and VL can be used in combination with checkpoint inhibitors (PDL-1 antibody, PD-1 antibody, LAG-3 antibody, TIM-3 antibody, TIGIT antibody, and other antibodies), and with chemotherapies to improve efficacy against cancer cells.

The following examples further illustrate the present invention. These examples are intended merely to be illustrative of the present invention and are not to be construed as being limiting.

EXAMPLES

Example 1. Materials and Methods

Cells and Culture Medium

HEK293FT cells from AlStem (Richmond, CA) were cultured in Dulbeceo's Modified Eagle's Medium (DMEM) plus 10% FBS and 1% penicillin/streptomycin. Human peripheral blood mononuclear cells (PBMC) were isolated from whole blood obtained from the Stanford Hospital Blood Center, Stanford, CA according to IRB-approved protocol using FICOLL-PAQUE® (in vitro isolation of lymphocytes) solution (GE Healthcare). Colon cancer cell lines: PLAP-negative: SW620, HT29, HCT116 and PLAP-positive: Lovo, Caco-2, LS123 were obtained from Dr. Walter Bodmer (Oxford, UK), whose laboratory authenticated cell lines using SNPs, Sequenom MassARRAY iPLEX and HumanOmniExpress-24 BeadChip arrays, and tested for the absence of Mycoplasma as described [28-29]. The cell lines were cultured in DMEM plus 10% FBS and penicillin/streptomycin. The list of 117 colon cancer cell lines from W. Bodmer laboratory which were used for PLAP mRNA level detection is shown in supplementary The cell lines were additionally authenticated by FACS using cell-specific surface markers and cultured in a humidified 5% CO2 incubator.

Antibodies

Monoclonal PD-1 (EH122H7), PDL-1 (clone 29E2A3), TIGIT (clone A15152G), LAG3 (clone 7H2C65), CD62L (clone DREG-56), CD45RO (clone UCHL1), CD4 (clone RPA-T4) and CD8 (clone RPA-T8) antibodies antibodies were from Biolegend. PLAP antibody (clone H17E2) was obtained from *Thermo Fisher*. Other antibodies were described in [30].

CAR Constructs

The second generation CAR with CD8 alpha signaling peptide, PLAP Ab ScFv [21], CD8 hinge, CD28 co-stimulatory domain and CD3 activation domain was cloned down-stream of EF1 promoter into modified lentiviral vector pCD510 (Systems Bioscience). The same construct was generated with humanized PLAP ScFv (called humanized PLAP or PLAPh2, h4 (clone 2 or 4), and Mock control with either ScFv of intracellular protein or Mock control with 45 amino-acid sequence containing three epitopes of transferrin antibody, called (Mock-CAR). The mouse PLAP-CAR was generated by Synbio. The humanized PLAP ScFv sequences was synthesized by IDT as GBLOCK® nucleic acid sequence with Nhe I and Xho I restriction sites flanking ScFv, and sub-cloned into these sites in lentiviral vector between CD8 alpha signaling peptide and CD8 hinge sequences.

Humanization of PLAP

Humanization of PLAP was performed as described in [31]. The human frames from human antibody clones with highest homology were used for humanized pairs using bioinformatics in silico methods as described [32,33]. Mouse CDR were inserted into these clones and different humanized ScFv variants were used for generating CAR constructs and performing CAR-T cell functional tests.

Lentivirus Preparation in 293FT Cells

The lentiviral CAR constructs were used for generation of lentivirus by transfecting 293 FT cells using transfection agent (Alstem) and Lentivirus Packaging Mix as described [34]. The lentiviral titers in pfu/ml were detected by RT-PCR using the Lenti-X qRT-PCR kit (Takara) according to the manufacturer's protocol and the 7900HT thermal cycler (Thermo Fisher).

Transduction with CAR Lentivirus and CAR-T Cell Expansion

AIM V® (serum-free medium) ALBUMAX® (bovine serum albumin)

PBMC were resuspended at $1\times10^6$ cells/ml in AIM V® (serum-free medium) ALBUMAX® (bovine serum albumin medium) (*Thermo Fisher*) containing 10% FBS with 300 U/ml IL-2 (*Thermo Fisher*). PBMC were activated with CD3/CD28 DYNABEADS® (microspheres, *Invitrogen*), and cultured in 24-well plates. CAR lentivirus was added to the PBMC cultures at 24 and 48 hours using TransPlus transduction enhancer (*AlStem*), as described [30,31,34]. The CAR-T cells were cultured and expanded for 14 days by adding fresh medium to maintain the cell density at $1\times10^6$ cells/ml.

Fluorescence-Activated Cell Sorting (FACS) Analysis

To detect CAR expression, $5\times10^5$ cells were suspended in 1×PBS plus 0.5% BSA buffer and incubated on ice with human serum (Jackson Immunoresearch, West Grove, PA) for 10 min. Then allophycocyanin (APC)-labeled anti-CD3 (eBioscience, San Diego, CA), 7-aminoactinomycin D (7-AAD, BioLegend, San Diego, CA), anti-F(ab)2 or its isotype control were added, and the cells were incubated on ice for 30 min. Then cells were rinsed with buffer, and analyzed on a FACSCalibur (BD Biosciences) first for light scatter versus 7-AAD staining, then the 7-AAD-negative live gated cells were plotted for CD3 staining versus F(ab)2 staining or isotype control staining. For FACS with colon cancer cell lines to detect PLAP levels mouse monoclonal PLAP antibody (H17E2) from Ximbio (London, UK) was used, and analysis was performed on FACSCalibur.

Blitz ForteBio Binding Assay

The binding of PLAP antibody with recombinant PLAP extracellular domain protein from Sino Biological was performed using Blitz ForteBio system as described [30]. In brief, anti-mouse-capture (AMC) biosensors were soaked in kinetics buffer (PBS, 0.1% Tween, 0.05% BSA) for 10 min and then with mouse anti-PLAP antibody at 0.1 mg/mL in same buffer for 30 min. After washing, biosensors were used to bind the PLAP antigen at different concentrations. The Kd was detected with Blitz system software.

Real-Time Cytotoxicity Assay (RTCA)

Adherent colon cancer target cells (10,000 cells per well) were seeded into 96-well E-plates (Acea Biosciences, San Diego, CA) and cultured overnight using the impedance-based real-time cell analysis (RTCA) iCELLigence system (Acea Biosciences). After 20-24 hours, the medium was replaced with 1×105 effector cells (CAR-T cells, Mock CAR-T cells or non-transduced T cells) in AIM V° ALBUMAX® medium containing 10% FBS, in triplicate. In some experiments checkpoint protein antibodies PD-1, LAG-3 or isotype at 10 µg/ml were added to the effector cells either alone or in combination with CAR-T cells. In some series of experiments target cells were pre-treated with 20 ng/ml of IFN-γ for 24 h. The cells were monitored for 1-2 days with the RTCA system, and impedance (proportional to cell index) was plotted over time. Cytotoxicity was calculated as (impedance of target cells without effector cells—impedance of target cells with effector cells)×100/impedance of target cells without effector cells.

ELISA Assay for Cytokine Secretion

The target cells were cultured with the effector cells (CAR-T cells or non-transduced T cells) at in U-bottom 96-well plates with AIM V® ALBUMAX® medium plus 10% FBS, in triplicate. After 16 h the supernatant was removed and centrifuged to remove residual cells. In some experiments, supernatant after RTCA assay was used for ELISA cytokine assays. The supernatant was transferred to a new 96-well plate and analyzed by ELISA for human cytokines using kits from Thermo Fisher according to the manufacturer's protocol.

Mouse In Vivo Xenograft Study

Six-week old male NSG mice (Jackson Laboratories, Bar Harbor, ME) were housed in accordance with the Institutional Animal Care and Use Committee (IACUC) protocol. Each mouse was injected subcutaneously with 2×10$^6$ colon cancer cells in sterile 1×PBS. The CAR-T cells (1×10$^7$ CAR-T cells/mice) were injected intravenously into mice at days 1, 7 and 13. Tumor sizes were measured with calipers twice-weekly and tumor volume (in mm$^3$) was determined using the formula $W^2L/2$, where W is tumor width and L is tumor length. At the end 0.1 ml of blood was collected and used for analysis of toxicology markers.

Toxicology Markers.

Mouse serum samples were processed with clinical chemistry analyzer (Beckman-Coulter AU680) by IDEX Bioanalytics (West Sacramento, CA) for detection levels of toxicology markers: ALT (alanine aminotransferase), AST (aspartate aminotransferase), amylase in U/ml.

Primary Tumor Samples

Samples with different types of normal tissues or tumor tissues were obtained from archived slides of Promab (Richmond, CA). The TMA slide with 106 primary colon cancer adenocarcinoma was obtained from Biomax (Rockville, MD) and used for IHC with PLAP antibody.

Immunohistochemistry (IHC) Staining

The primary tumor tissue or normal tissue section slides or primary TMA slides were incubated in xylene twice for 10 min, then hydrated in alcohol and rinsed in 1xPBS. Heat-induced antigen retrieval was performed using a pressure cooker for 20 min in 10 mM citrate buffer, pH 6.0. The slides were rinsed with PBS, incubated in a 3% $H_2O_2$ solution for 10 min, then rinsed again with 1xPBS, and incubated in goat serum for 20 min. The tissue section slides were incubated with mouse monoclonal PLAP (H17E2) primary antibody overnight at 4° C. or 1.5 hours at 37° C. The slides were rinsed 3 times with PBS, incubated with biotin-conjugated secondary antibody for 10 min, rinsed with PBS, incubated with streptavidin-conjugated peroxidase for 10 min, and rinsed 3 times with 1xPBS buffer. The slides were incubated in DAB substrate solution for 2-5 min under the microscope. The reaction was stopped by washing in water, counterstained with hematoxylin, rinsed with water, and dehydrated in 75%, 80%, 95% and 100% ethanol and xylene. For negative control isotype antibody was used, and for positive control placenta samples were used. Images were acquired on the Motic DMB5-2231PL microscope using Images Plus 2.0. software (Motic, Xiamen, China). PLAP expression correlation with survival free prognosis was performed using R2 Genomics Analysis and Visualization platform (2platform.com/r2.amc.nl).

Example 2. The Sequence of Mouse PLAP-CD28-CD3Zeta CAR

Figure 2:
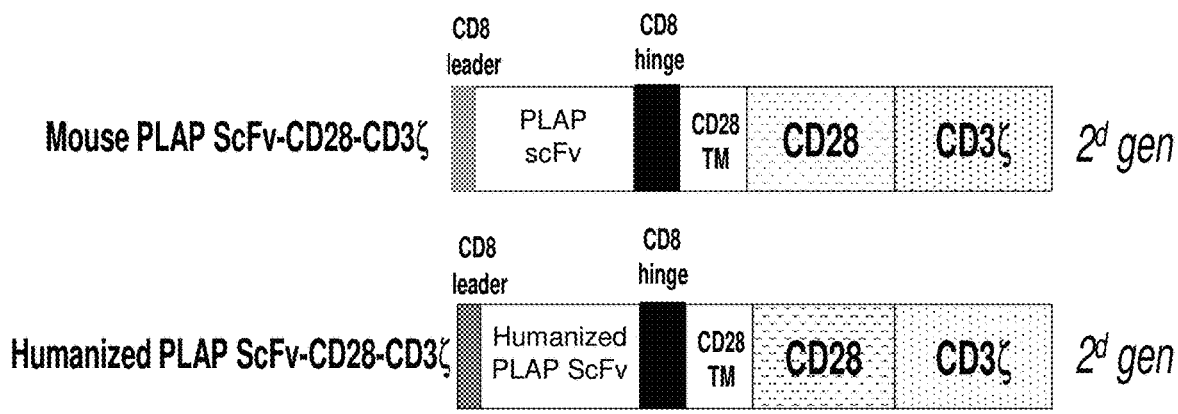
FIG. 2 shows the structure of mouse and humanized PLAP-CAR constructs.

The CAR structures were: Human CD8 signaling peptide, mouse scFv or humanized derived from antibody H17E2 ($V_H$-Linker-3x(GGGGS)-$V_L$), CD8 hinge, CD28 transmembrane, co-activation domain, CD3 zeta activation domain (FIG. 2). The sequence of lentiviral vector with CAR construct inside Eco R1 and Xho I site is shown below. The scFv is flanked with Nhe I and Xho I sites for potential re-cloning to other constructs. The nucleotide sequence of PLAP-CD28-CD3 is shown below,

```
SEQ ID NO: 2, tctagagccgccacc-flanking vector sequence starting with Xba I site (italics):
```

SEQ ID NO: 3 (Mouse PLAP CAR, called PMC262), starting with ATG and ending with a stop codon TAA (underlined), signaling peptide is in bold, VH with CDRs 1, 2, 3, bold underlined; linker in italics, VL with CDR 1,2,3 in bold, underlined); ScFV is flanked by 5' Nhe and 3' Xho sites, small font

```
ATGGCCTTACCAGTGACCGCCTTGCTCCTGCCGCTGGCCTTGCTGCTCCA

CGCCGCCAGGCCGgctagcCAGGTGCAGCTGAAGGAGTCAGGACCTGGCC

TGGTGGCGCCCTCACAGAGCCTGTCCATCACATGCACTGTCTCAGGGTTC

TCATTAACCAGTTATGGTGTAAGCTGGGTTCGCCAGCCTCCAAGAAGGG
```

```
TCTGGAGTGGCTGGGAGTAATATGGGAAGACGGGAGCACAAATTATCATT
CAGCTCTCATATCCAGACTGAGCATCAACAAGGATAACTCCAAGAGCCAA
GTTTTCTTAAAACTGAACAGTCTGCAAACTGATGACACAGCCACGTACTA
CTGTGCCAAACCCCACTACGGTAGCAGCTACGTGGGGGCTATGGAATACT
GGGGTCAAGGAACCTCAGTCACCGTCTCCTCA
GGTGGCGGTGGTTCTGGTGGCGGTGGTTCTGGTGGCGGTGGTTCT
GAC ATC CAG ATG ACT CAG TCT CCA GCC TCC CTA ACT
GCA TCT GTG GGA GAA ACT GTC ACCATC ACC TGT CGA
GCA AGT GAA AAT ATT TAC AGT TAT GTA GCA TGG TAT
CAG CAG AAA CAGGGA AAA TCT CCT CAG TTC CTG GTC
TAT AAT GCA AAA TCC TTA GCA GAG GGT GTG CCA
TCAAGG TTC AGT GGC AGY GGA TCA GGC ACA CAG TTT
TCT CTG AAG ATC AAC AGC CTG CAG CCTGAA GAT TTT
GGG AAT TAT TAC TGT CAA CAT CAT TAT GTT AGT CCG
TGG ACG TTC GGT GGAGGC ACC AAG CTG GAA ATC AGA
CGG ctcgagAAGCCCACCACGACGCCAGCGCCGCGACCACCAACACCGG
CGCCCACCATCGCGTCGCAGCCCCTGTCCCTGCGCCCAGAGGCGAGCCGG
CCAGCGGCGGGGGGCGCAGTGCACACGAGGGGGCTGGACTTCGCCAGTGA
Taagcccttttgggtgctggtggtggttggtggagtcctggcttgctata
gcttgctagtaacagtggcctttattattttctgggtgaggagtaagagg
agcaggctcctgcacagtgactacatgaacatgactccccgccgccccgg
gcccacccgcaagcattaccagccctatgccccaccacgcgacttcgcag
cctatcgctccAGAGTGAAGTTCAGCAGGAGCGCAGACGCCCCCGCGTAC
CAGCAGGGCCAGAACCAGCTCTATAACGAGCTCAATCTAGGACGAAGAGA
GGAGTACGATGTTTTGGACAAGAGACGTGGCCGGGACCCTGAGATGGGGG
GAAAGCCGCAGAGAAGGAAGAACCCTCAGGAAGGCCTGTACAATGAACTG
CAGAAAGATAAGATGGCGGAGGCCTACAGTGAGATTGGGATGAAAGGCGA
GCGCCGGAGGGGCAAGGGGCACGATGGCCTTTACCAGGGTCTCAGTACAG
CCACCAAGGACACCTACGACGCCCTTCACATGCAGGCCCTGCCCCCTCGC
TAA
```

SEQ ID NO: 4: tagGAATTC flanking vector with EcoR I site (*italics*)

SEQ ID NO: 5 is the amino acid sequence of SEQ ID NO: 3 (mouse PLAP-CD28-CD3zeta CAR): signaling peptide-VH-linker (in italics smaller font GSSSSx3)-VL-h-CD28-CD3. Sequence in bold is mouse PLAP scFv; CDR 1,2,3 underlined; VH-linker in italics-VL.

(SEQ ID NO: 5)
M A L P V T A L L L P L A L L L H A A R P A S Q V
Q L K E S G P G L V A P S Q S L S I T C T V S G <u>F</u>
<u>S L T S Y G V S</u> W V R Q P P R K G L E W L G V <u>I W</u>
<u>E D G S T N Y H S A L I S</u> R L S I N K D N S K S Q
V F L K L N S L Q T D D T A T Y Y C A K <u>P H Y G S</u>
<u>S Y V G A M E Y</u> W G Q G T S V T V S S
*GGGGSGG GGSGGGGS* D I Q M T Q S P A S
L T A S V G E T V T I T C <u>R A S E N I Y S Y V A</u> W
Y Q Q K Q G K S P Q F L V Y <u>N A K S L A</u> E G V P S
R F S G X G S G T Q F S L K I N S L Q P E D F G N
Y Y C <u>Q H H Y V S P W T</u> F G G G T K L E I R R L E
K P T T T P A P R P P T P A P T I A S Q P L S L R
P E A S R P A A G G A V H T R G L D F A S D K P F
W V L V V V G G V L A C Y S L L V T V A F I I F W
V R S K R S R L L H S D Y M N M T P R R P G P T R
K H Y Q P Y A P P R D F A A Y R S R V K F S R S A
D A P A Y Q Q G Q N Q L Y N E L N L G R R E E Y D
V L D K R R G R D P E Met G G K P Q R R K N P Q E
G L Y N E L Q K D M A E A Y S E I G M K G E R R
R G K G H D G L Y Q G L S T A T K D T Y D A L H M
Q A L P P R

Mouse VH (with underlined CDR 1, 2, 3),
(SEQ ID NO: 6)
Q V Q L K E S G P G L V A P S Q S L S I T C T V S
G <u>F S L T S Y G V S</u> W V R Q P P R K G L E W L G V
<u>I W E D G S T N Y H S A L I S</u> R L S I N K D N S K
S Q V F L K L N S L Q T D D T A T Y Y C A K <u>P H Y</u>
<u>G S S Y V G A M E Y</u> W G Q G T S V T V S S Mouse VL (with underlined CDR 1, 2, 3),
(SEQ ID NO: 7)
D I Q M T Q S P A S L T A S V G E T V T I T C <u>R A</u>
<u>S E N I Y S Y V A</u> W Y Q Q K G K S P Q F L V Y <u>N</u>
<u>A K S L A</u> E G V P S R F S G X G S G T Q F S L K I
N S L Q P E D F G N Y Y C <u>Q H H Y V S P W T</u> F G G
G T K L E I R R Mouse PLAP scFv,
(SEQ ID NO: 8)
Q V Q L K E S G P G L V A P S Q S L S I T C T V S
G <u>F S L T S Y G V S</u> W V R Q P P R K G L E W L G V
<u>I W E D G S T N Y H S A L I S</u> R L S I N K D N S K
S Q V F L K L N S L Q T D D T A T Y Y C A K <u>P H Y</u>
<u>G S S Y V G A M E Y</u> W G Q G T S V T V S S *GGGG*
*SGGGGSGGGGS* D I Q M T Q S P A S L T A S
V G E T V T I T C <u>R A S E N I Y S Y V A</u> W Y Q Q K
Q G K S P Q F L V Y <u>N A K S L A</u> E G V P S R F S G
X G S G T Q F S L K I N S L Q P E D F G N Y Y C <u>Q</u>
<u>H H Y V S P W T</u> F G G G T K L E I R R The scheme of CAR construct is shown below, which shows the sub-domain sequences of SEQ ID NO: 3.

<huCD8 signal peptide>
SEQ ID NO: 9
ATGGCCTTACCAGTGACCGCCTTGCTCCTGCCGCTGGCCTTGCTGCTCCA

CGCCGCCAGGCCG

<NheI restriction site>
GCTAGC

<Mouse PLAP scFv (VH-linker-VL)>
SEQ ID NO: 10
ATGGCCTTACCAGTGACCGCCTTGCTCCTGCCGCTGGCCTTGCTGCTCCA CGCCGCCAGGCCGgctagcCAGGTGCAGCTGAAGGAGTCAGGACCTGGCC

TGGTGGCGCCCTCACAGAGCCTGTCCATCACATGCACTGTCTCAGGGTTC

TCATTAACCAGTTATGGTGTAAGCTGGGTTCGCCAGCCTCCAAGAAAGGG

TCTGGAGTGGCTGGGAGTAATATGGGAAGACGGGAGCACAAATTATCATT

CAGCTCTCATATCCAGACTGAGCATCAACAAGGATAACTCCAAGAGCCAA

GTTTTCTTAAAACTGAACAGTCTGCAAACTGATGACACAGCCACGTACTA

CTGTGCCAAACCCCACTACGGTAGCAGCTACGTGGGGGCTATGGAATACT

GGGGTCAAGGAACCTCAGTCACCGTCTCCTCA*GGTGGCGGTGGTTCT*

*GGTGGCGGTGGTTCTGGTGGCGGTGGTTCT*

GAC ATC CAG ATG ACT CAG TCT CCA GCC TCC CTA ACT

GCA TCT GTG GGA GAA ACT GTC ACCATC ACC TGT CGA GCA

AGT GAA AAT ATT TAC AGT TAT GTA GCA TGG TAT CAG

CAG AAA CAGGGA AAA TCT CCT CAG TTC CTG GTC TAT AAT

GCA AAA TCC TTA GCA GAG GGT GTG CCA TCAAGG TTC AGT

GGC AGY GGA TCA GGC ACA CAG TTT TCT CTG AAG ATC

AAC AGC TTG CAG CCTGAA GAT TTT GGG AAT TAT TAC TGT

CAA CAT CAT TAT GTT AGT CCG TGG ACG TTC GGT GGAGGC

ACC AAG CTG GAA ATC AGA CGG

<XhoI restriction site>
CTCGAG

<CD8>
SEQ ID NO: 11
AAGCCCACCACGACGCCAGCGCCGCGACCACCAACACCGGCGCCCACCAT

CGCGTCGCAGCCCCTGTCCCTGCGCCCAGAGGCGAGCCGGCCAGCGGCGG

GGGGCGCAGTGCACACGAGGGGGCTGGACTTCGCCAGTGATaagccc

<CD28 TM/activation>
SEQ ID NO: 12
TTTTGGGTGCTGGTGGTGGTTGGTGGAGTCCTGGCTTGCTATAGCTTGCT

AGTAACAGTGGCCTTTATTATTTTCTGGGTGAGGAGTAAGAGGAGCAGGC

TCCTGCACAGTGACTACATGAACATGACTCCCCGCCGCCCCGGGCCCACC

CGCAAGCATTACCAGCCCTATGCCCCACCACGCGACTTCGCAGCCTATCG

CTCC

<CD3zeta>
SEQ ID NO: 13
AGAGTGAAGTTCAGCAGGAGCGCAGACGCCCCCGCGTACCAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGCTAATAG

<EcoRI restriction site>
Gaattc

Example 3. PLAP CAR with Humanized Antibody h1

SEQ ID NO: 14 (human h1 PLAP CAR), starting with ATG and ending with a stop codon TAA (underlined). The sequence starts with a signaling peptide, then the humanized PLAP scFv h1. The nucleotide sequence has the same structure as SEQ ID NO: 2 except the scFv portion. The bold sequence is humanized h1 PLAP-1 scFv (CDRs 1, 2, 3 are underlined). Different nucleotides in humanized frame regions compared with mouse are underlined but not bolded.

(SEQ ID NO: 14)
ATGGCCTTACCAGTGACCGCCTTGCTCCTGCCGCTGGCCTTGCTGCTCCA

CGCCGCCAGGCCGgctagcCAGGTCCAACTGCAGGAGAGCGGTCCAGGTC

TTGTGAGACCTAGCCAGACCCTGAGCCTGACCTGCACCGTGTCTGGCTTC

ACCTTCACCAGTTATGGTGTAAGCTGGGTGAGACAGCCACCTGGACGAGG

TCTTGAGTGGATTGGAGTAATATGGGAAGACGGGAGCACAAATTATCATT

CAGCTCTCATATCCAGAGTGACAATGCTGGTAGACACCAGCAAGAACCAG

TTCAGCCTGAGACTCAGCAGCGTGACAGCCGCCGACACCGCGGTCTATTA

TTGTGCAAGACCCCACTACGGTAGCAGCTACGTGGGGGCTATGGAATACT

GGGGTCAAGGCAGCCTCGTCACAGTCTCCTCA*GGTGGCGGTGGTTCT*

*GGTGGCGGTGGTTCTGGTGGCGGTGGTTCT*

GAC ATC CAG ATG ACC CAG AGC CCA AGC AGC CTG AGC

GCC AGC GTG GGT GAC AGA GTG ACC

ATC ACC TGT CGA GCA AGT GAA AAT ATT TAC AGT TAT

GTA GCA TGG TAC CAG CAG AAG

CCA GGT AAG GCT CCA AAG CTG CTG ATC TAC AAT GCA

AAA TCC TTA GCA GAG GGT GTG CCA AGC

AGA TTC AGC GGT AGC GGT AGC GGT ACC GAC TTC ACC

TTC ACC ATC AGC AGC CTC CAG

CCA GAG GAC ATC GCC ACC TAC TAC TGC CAA CAT CAT

TAT GTT AGT CCG TGG ACG TTC GGC CAA

GGG ACC AAG GTG GAA ATC AAA CGT ctcgagAAGCCCACCACGACGCCAGCGCCGCGACCACCAACACCGGCGCC

CACCATCGCGTCGCAGCCCCTGTCCCTGCGCCCAGAGGCGAGCCGGCCAG

CGGCGGGGGGCGCAGTGCACACGAGGGGGCTGGACTTCGCCAGTGATaag cccttttgggtgctggtggtggttggtggagtcctggcttgctatagctt -continued
```
gctagtaacagtggcctttattattttctgggtgaggagtaagaggagca ggctcctgcacagtgactacatgaacatgactccccgccgccccgggccc acccgcaagcattaccagccctatgccccaccacgcgacttcgcagccta tcgctccAGAGTGAAGTTCAGCAGGAGCGCAGACGCCCCCGCGTACCAGC

AGGGCCAGAACCAGCTCTATAACGAGCTCAATCTAGGACGAAGAGAGGAG

TACGATGTTTTGGACAAGAGACGTGGCCGGGACCCTGAGATGGGGGAAA

GCCGCAGAGAAGGAAGAACCCTCAGGAAGGCCTGTACAATGAACTGCAGA

AAGATAAGATGGCGGAGGCCTACAGTGAGATTGGGATGAAAGGCGAGCGC

CGGAGGGGCAAGGGGCACGATGGCCTTTACCAGGGTCTCAGTACAGCCAC

CAAGGACACCTACGACGCCCTTCACATGCAGGCCCTGCCCCCTCGCTAA
```

SEQ ID NO: 15 is humanized h1 PLAP-1 CAR amino-acid sequence; it has the same structure as mouse PLAP-CAR except the scFv portion; sequence in bold is humanized h1 PLAP-1 ScFv, CDR 1, 2, 3 are in italics and underlined; linker are in a smaller font; different amino-acids in CDR regions in regular font; different amino-acids from mouse sequence in frame region are underlined.

(SEQ ID NO: 15)
M A L P V T A L L L P L A L L L H A A R P A S Q V

Q L Q E S G P G L V R P S Q T L S L T C T V S

G *F T F T S Y G V S* W V R Q P P G R G L E W I G

*A L I S* R V T M L V D T S K N Q F S L R L S S V T

A A D T A V Y Y C A *R P H Y G S S Y V G A M E Y*

W G Q G S L V T V S S GGGGSGGGGSGGGGS

D I Q M T Q S P S S L S A S V G D R V T I T C

*R A S E N I Y S Y V A* A W Y Q Q K P G K A P K L L I Y

*N A K S L A* E G V P S R F S G S G S G T D F T F T

I S S L Q P E D I A T Y C *Q H H Y V S P W* T F G Q G

T Y K V E I K R L E K P T T T P A P R P P T P A P

T I A S Q P L S L R E A S R P A A G G A V H T R P

G L D F A S D K P F W V L V V V G G V L A C Y S L

L V T V A F I I F W V R S K R S R L L H S D Y M N

M T P R R P G P T R K H Y Q P Y A P P R D F A A Y

R S R V K F S R S A D A P A Y Q Q G Q N Q L Y N E

L N L G R R E E Y D V L D K R R G R D P E M G G K

P Q R R K N P Q E G L Y N E L Q K D K M A E A Y S

E I G M K G E R R R G K G H D G L Y Q G L S T A T

K D T Y D A L H M Q A L P P R

Humanized h1 PLAP-1 VH
(SEQ ID NO: 16)
Q V Q L Q E S G P G L V R P S Q T L S L T C T V S

G F T F *T S Y G* V S W V R Q P P G R G L E W I G V

*I W E D G S T* N Y H S A L I S R V T M L V D T S K

N Q F S L R L S S V T A A D T A V Y Y C

A R *P H Y G S S Y V G A M E Y* W G Q G S L V T V S S

Humanized h1 PLAP-1 VL
(SEQ ID NO: 17)
D I Q M T Q S P S S L S A S V G D R V T I T C R A

S *E N I Y S Y* V A W Y Q Q K P G K A P K L L I Y N

A K S L A E G V P S R F S G S G S G T D F T F T I

S S L Q P E D I A T Y Y C *Q H H Y V S P W T F* G Q

G T K V E I K R

Humanized h1 PLAP-1 scFv
(SEQ ID NO: 18)
Q V Q L Q E S G P G L V R P S Q T L S L T C T V S

G F T F *T S Y G* V S W V R Q P P G R G L E W I G V

*I W E D G S T* N Y H S A L I S R V T M L V D T S K

N Q F S L R L S S V T A A D T A V Y Y C A R

*P H Y G S S Y V G A M E Y* W G Q G S L V T V S S

*GGGGSGGGGSGGGGS* D I Q M T Q S P S S

L S A S V G D R V T I T C R A S *E N I Y S Y* V A W

Y Q Q K P G K A P K L L I Y N A K S L A E G V P S

R F S G S G S G T D F T F T I S S L Q P E D I A T

Y Y C *Q H H Y V S P W T F* G Q G T K V E I K R

Example 4. PLAP CAR with Humanized Antibody h2

The bioinformatics approach was performed to generate additional humanized versions of PLAP CAR. The sequences were codon-optimized for higher expression of CAR.

The sequence starts with a signaling peptide (underlined, codon optimized), then the humanized PLAP scFv (bold). The nucleotide sequence has the same structure as SEQ ID NO: 3, except the scFv portion. The bold sequence is humanized PLAP-h2 (PMC409) scFv, the rest is same structure as mouse PLAP-CAR (SEQ ID NO: 5).

Humanized PLAP h2- CAR. Nucleotide sequence (codon optimized),
SEQ ID NO: 19
ATGGCCTTACCAGTGACCGCCTTGCTCCTGCCGCTGGCCTTGCTGCTCCA CGCCGCCAGGCCGgctagc

CAG GTG CAG CTT CAG GAA AGT GGA CCG GGC CTT GTC

AAA CCG TCA GAG ACC CTT TCA CTG ACT TGC ACTGTA AGT

GGT TTC TCC CTG ACA AGC TAC GGA GTC TCC TGG ATA

CGC CAG CCA GCG GGG AAA GGG CTT GAGTGG ATC GGT GTG

ATC TGG GAA GAC GGG AGT ACA AAC TAT CAC TCA GCA

CTC ATT AGT CGA GTA ACA ATGTCC GTT GAC ACT TCC AAG

AAT CAA TTC AGT TTG AAA CTG TCT AGT GTG ACG GCT

GCG GAT ACA GCG GTTTAT TAC TGT GCC AGG CCT CAT TAC

```
GGA AGT TCT TAT GTT GGT GCA ATG GAG TAT TGG GGA

GCC GGC ACAACT GTC ACT GTG AGC TCC GGC GGG GGC GGA

AGT GGG GGA GGA GGC TCA GGC GGA GGT GGA AGT GAT

ATACAG ATG ACC CAG AGT CCT AGC TCA CTC TCT GCG TCC

GTA GGG GAC CGG GTA ACC ATC ACA TGC CGC GCCAGC GAG

AAT ATA TAC AGT TAC GTT GCA TGG TAC CAG CAA AAA

CCT GGC AAG GCG CCG AAG CTG TTG ATCTAC AAC GCC AAA

AGT CTC GCT TCC GGG GTC CCC AGC CGA TTT TCT GGC

TCA GGT AGT GGC ACA GAT TTCACA CTC ACA ATA AGC TCT

CTC CAG CCC GAA GAC TTT GCG ACG TAC TAC TGC CAG

CAT CAT TAT GTT AGTCCT TGG ACG TTT GGC GGA GGC ACA

AAA TTG GAA ATA AAA ctcgagAAGCCCACCACGACGCCAGCGCCGCGACCACCAACACCGGCGCC

CACCATCGCGTCGCAGCCCCTGTCCCTGCGCCCAGAGGCGAGCCGGCCAG

CGGCGGGGGGCGCAGTGCACACGAGGGGGCTGGACTTCGCCAGTGATaag ccctttgggtgctggtggtggttggtggagtcctggcttgctatagctt gctagtaacagtggcctttattattttctgggtgaggagtaagaggagca ggctcctgcacagtgactacatgaacatgactccccgccgccccgggccc acccgcaagcattaccagccctatgccccaccacgcgacttcgcagccta tcgctccAGAGTGAAGTTCAGCAGGAGCGCAGACGCCCCCGCGTACCAGC

AGGGCCAGAACCAGCTCTATAACGAGCTCAATCTAGGACGAAGAGAGGAG

TACGATGTTTTGGACAAGAGACGTGGCCGGGACCCTGAGATGGGGGAAA

GCCGCAGAGAAGGAAGAACCCTCAGGAAGGCCTGTACAATGAACTGCAGA

AAGATAAGATGGCGGAGGCCTACAGTGAGATTGGGATGAAAGGCGAGCGC

CGGAGGGGCAAGGGCACGATGGCCTTTACCAGGGTCTCAGTACAGCCAC

CAAGGACACCTACGACGCCCTTCACATGCAGGCCCTGCCCCCTCGCTAA
```

The humanized PLAP h2 CAR amino-acid sequence is shown in SEQ ID NO: 20. It has the same structure as Mouse PLAP-CAR except the scFv portion; sequence in bold is humanized PLAP ScFV consisting from VL-linker-VL.

(SEQ ID NO: 20)
M A L P V T A L L L P L A L L L H A A R P A S Q V
Q L Q E S G P G L V K P S E T L S L T C T V S G F
S L T S Y G V S W I R Q P A G K G L E W I G V I W
E D G S T N Y H S A L I S R V T M S V D T S K N Q
F S L K L S S V T A A D T A V Y Y C A R P H Y G S
S Y V G A M E Y W G A G T T V T V S S G G G G S G
G G G S G G G G S D I Q M T Q S P S S L S A S V G
D R V T I T C R A S E N I Y S Y V A W Y Q Q K P G
K A P K L L I Y N A K S L A S G V P S R F S G S G
S G T D F T L T I S S L Q P E D F A T Y Y C Q H H
Y V S P W T F G G G T K L E I K L E K P T T T P A
P R P P T P A P T I A S Q P L S L R P E A S R P A
A G G A V H T R G L D F A S D K P F W V L V V V G
G V L A C Y S L L V T V A F I I F W V R S K R S R
L L H S D Y M N M T P R R P G P T R K H Y Q P Y A
P P R D F A A Y R S R V K F S R S A D A P A Y Q Q
G Q N Q L Y N E L N L G R R E E Y D V L D K R R G
R D P E M G G K P Q R R K N P Q E G L Y N E L Q K
D K M A E A Y S E I G M K G E R R R G K G H D G L
Y Q G L S T A T K D T Y D A L H M Q A L P P R

Humanized PLAP h2 VH
(SEQ ID NO: 21)
Q V Q L Q E S G P G L V K P S E T L S L T C T V S
G F S L T S Y G V S W I R Q P A G K G L E W I G V
I W E D G S T N Y H S A L I S R V T M S V D T S K
N Q F S L K L S S V T A A D T A V Y Y C A R P H Y
G S S Y V G A M E Y W G A G T T V T V S S Humanized PLAP h2 VL, CDR 1, 2, 3, underlined
(SEQ ID NO: 22)
DIQMTQSPSSLSASVGDRVTITC<u>RASENIYSYVA</u>WYQQKPGKAPKLLIY<u>N</u>
<u>AKSLAS</u>GVPSRFSGSGSGTDFTLTISSLPEDFATYYC<u>QHHYVSPWT</u>FGG
GTKLEIK Humanized PLAP h2 scFv
(SEQ ID NO: 23)
Q V Q L Q E S G P G L V K P S E T L S L T C T V S
G F S L T S Y G V S W I R Q P A G K G L E W I G V
I W E D G S T N Y H S A L I S R V T M S V D T S K
N Q F S L K L S S V T A A D T A V Y Y C A R P H Y
G S S Y V G A M E Y W G A G T T V T V S S G G G G
S G G G G S G G G G S D I Q M T Q S P S S L S A S
V G D R V T I T C R A S E N I Y S Y V A W Y Q Q K
P G K A P K L L I Y N A K S L A S G V P S R F S G
S G S G T D F T L T I S S L Q P E D F A T Y Y C Q
H H Y V S P W T F G G G T K L E I K Example 5. PLAP CAR with Humanized Antibody h4

The humanized PLAP h4 CAR (PMC410) codon optimized nucleotide sequence starts with a signaling peptide (underlined, SEQ ID NO: 9, codon optimized), then the humanized PLAP scFv (bold). The bold sequence is humanized PLAP-h4 (PMC410) scFv, SEQ ID NO: 24 is the humanized PLAP h4-CAR nucleotide sequence (codon optimized).
<u>ATGGCCTTACCAGTGACCGCCTTGCTCCTGCCGCTGGCCTTGCTGCTCCA</u>
<u>CGCCGCCAGGCCG</u>gctagc
CAG GTT CAA CTT CAA GAA TCA GGA CCG GGC TTG GTT

```
AAA CCT TCC GAA ACT CTG AGC CTT ACT TGT ACAGTG TCT

GGT GGA TCT ATT ACG AGC TAC GGA GTA AGT TGG ATC

CGG CAA CCA CCC GGG AAA GGG CTC GAATGG ATA GGG GTG

ATA TGG GAG GAT GGT TCA ACC AAC TAC CAT AGC GCT

CTG ATC AGC CGG GTG ACC ATTAGT GTC GAC ACT TCC AAA

AAC CAG TTT TCA TTG AAG CTC TCA AGC GTA ACT GCG

GCG GAT ACC GCC GTATAC TAT TGT GCG CGG CCA CAT TAC

GGG TCC TCT TAT GTT GGG GCG ATG GAA TAT TGG GGG

GCA GGT ACAACG GTC ACG GTG TCT TCA GGA GGA GGA GGG

TCA GGT GGT GGT GGT TCA GGA GGC GGG GGT AGC GAC

ATACAG ATG ACT CAA AGC CCC TCT TCA CTG TCT GCA TCA

GTC GGG GAC AGA GTC ACA ATA ACC TGC AGA GCGAGC GAG

AAT ATC TAC TCT TAT GTA GCC TGG TAT CAG CAA AAA

CCC GGC AAG GCG CCG AAA TTG CTC ATCTAT AAT GCG AAA

TCC TTG GCC AGT GGG GTC CCA TCA CGG TTC AGT GGC

TCC GGC TCT GGA ACC GAT TTCACA CTC ACA ATC TCT AGC

CTC CAG CCC GAA GAC TTC GCC ACA TAC TAT TGC CAA

CAT CAC TAT GTC AGCCCA TGG ACA TTT GGG GGA GGT ACG

AAA CTT GAA ATT AAA ctcgagAAGCCCACCACGACGCCAGCGCCGCGACCACCAACACCGGCGCC

CACCATCGCGTCGCAGCCCCTGTCCCTGCGCCCAGAGGCGAGCCGGCCAG

CGGCGGGGGCGCAGTGCACACGAGGGGGCTGGACTTCGCCAGTGATaag ccctttgggtgctggtggtggttggtggagtcctggcttgctatagctt gctagtaacagtggcctttattattttctgggtgaggagtaagaggagca ggctcctgcacagtgactacatgaacatgactccccgccgccccgggccc acccgcaagcattaccagccctatgccccaccacgcgacttcgcagccta tcgctccAGAGTGAAGTTCAGCAGGAGCGCAGACGCCCCCGCGTACCAGC

AGGGCCAGAACCAGCTCTATAACGAGCTCAATCTAGGACGAAGAGAGGAG

TACGATGTTTTGGACAAGAGACGTGGCCGGGACCCTGAGATGGGGGGAAA

GCCGCAGAGAAGGAAGAACCCTCAGGAAGGCCTGTACAATGAACTGCAGA

AAGATAAGATGGCGGAGGCCTACAGTGAGATTGGGATGAAAGGCGAGCGC

CGGAGGGGCAAGGGGCACGATGGCCTTTACCAGGGTCTCAGTACAGCCAC

CAAGGACACCTACGACGCCCTTCACATGCAGGCCCTGCCCCCTCGCTAAt ag

SEQ ID NO: 25 is the humanized PLAP h4 CAR amino-
acid sequence: ScFv sequence is in bold.
M A L P V T A L L L P L A L L L H A A R P A S Q V

Q L Q E S G P G L V K P S E T L S L T C T V S G G

S I T S Y G V S W I R Q P P G K G L E W I G V I W

E D G S T N Y H S A L I S R V T I S V D T S K N Q

F S L K L S S V T A A D T A V Y Y C A R P H Y G S
```

```
S Y V G A M E Y W G A G T T V T V S S G G G G S G

G G G S G G G G S D I Q M T Q S P S S L S A S V G

D R V T I T C R A S E N I Y S Y V A W Y Q Q K P G

K A P K L L I Y N A K S L A S G V P S R F S G S G

S G T D F T L T I S S L Q P E D F A T Y Y C Q H H

Y V S P W T F G G G T K L E I K L E K P T T T P A

P R P P T P A P T I A S Q P L S R P E A S R P A

A G G A V H T R G L D F A S D K P F W V L V V V G

G V L A C Y S L L V T V A F I I F W V R S K R S R

L L H S D Y M N M T P R R P G P T R K H Y Q P Y A

P P R D F A A Y R S R V K F S R A D A P A Y Q Q

G Q N Q L Y N E L N L G R R E E Y D V L D K R R G

R D P E M G G K P Q R R K N P Q E G L Y N E L Q K

D K M A E A Y S E I G M K G E R R R G K G H D G L

Y Q G L S T A T K D T Y D A L H M Q A L P P R

Humanized PLAP-h4 VH (SEQ ID NO: 26). CDR 1, 2, 3
underlined
Q V Q L Q E S G P G L V K P S E T L S L T C T V S G <u>G S I T S Y G</u> V S W I R Q P P G K G L E W I G <u>V</u>

<u>I W E D G S T N Y H S A L I</u> S R V T I S V D T S K

N Q F S L K L S S V T A A D T A V Y Y C A R <u>P H Y</u>

<u>G S S Y V G A M E Y</u> W G A G T T V T V S S

Humanized PLAP-h4 VL (SEQ ID NO: 22)

Humanized PLAP-h4 scFv (SEQ ID NO: 27)
```

Example 6. PLAP CAR with Humanized Antibody h3

SEQ ID NO: 28 is the humanized PLAP-h3 (PMC407)
nucleotide sequence:
<u>ATGGCCTTACCAGTGACCGCCTTGCTCCTGCCGCTGGCCTTGCTGCTCCA</u>

<u>CGCCGCCAGGCCG</u>gctagc

```
CAG GTT CAA TTG CAA GAA TCA GGC CCT GGG CTT GTT

AAG CCG TCA GAG ACG CTT TCA CTG ACC TGT ACCGTG AGC

GGG TTC AGC CTC ACT TCC TAT GGT GTT TCT TGG ATA

CGA CAA CCA CCC GGA AAG GGC CTG GAATGG ATC GGG GTC

ATT TGG GAA GAT GGA TCC ACA AAC TAC AAT CCT TCA

CTT AAA TCC CGA GTT ACT ATCTCT GTT GAC ACC AGT AAA

AAT CAA TTC AGT CTC AAA CTG TCC AGT GTG ACA GCC

GCC GAC ACA GCA GTCTAC TAT TGC GCT CGC CCA CAT TAC

GGC TCC AGC TAC GTT GGG GCG ATG GAA TAT TGG GGA

GCT GGT ACCACA GTC ACG GTT AGT AGT GGA GGA GGT GGT

TCC GGG GGA GGG GGG AGC GGC GGA GGT GGA TCT GAT
```

```
ATCCAG ATG ACT CAG TCT CCA AGT TCC CTT TCT GCA AGC
GTA GGT GAT CGA GTC ACT ATC ACA TGC AGG GCGTCC GAG
AAC ATA TAC AGT TAT GTT GCA TGG TAC CAA CAG AAG
CCA GGT AAA GCG CCT AAG CTG CTT ATTTAT AAC GCT AAA
TCT CTT GCT TCT GGG GTA CCA TCC CGA TTC TCA GGG
TCT GGA AGT GGC ACT GAT TTCACG TTG ACT ATT TCC TCC
CTT CAA CCG GAG GAT TTT GCA ACG TAC TAC TGT CAG
CAT CAT TAT GTC AGCCCG TGG ACG TTC GGT GGC GGC ACG
AAA CTT GAG ATT AAA
ctcgagAAGCCCACCACGACGCCAGCGCCGCGACCACCAACACCGGCGCC
CACCATCGCGTCGCAGCCCCTGTCCCTGCGCCCAGAGGCGAGCCGGCCAG
CGGCGGGGGCGCAGTGCACACGAGGGGGCTGGACTTCGCCAGTGATaag
cccttttgggtgctggtggtggttggtggagtcctggcttgctatagctt
gctagtaacagtggcctttattattttctgggtgaggagtaagaggagca
ggctcctgcacagtgactacatgaacatgactcccgccgccccgggccc
acccgcaagcattaccagccctatgccccaccacgcgacttcgcagccta
tcgctccAGAGTGAAGTTCAGCAGGAGCGCAGACGCCCCCGCGTACCAGC
AGGGCCAGAACCAGCTCTATAACGAGCTCAATCTAGGACGAAGAGAGGAG
TACGATGTTTTGGACAAGAGACGTGGCCGGGACCCTGAGATGGGGGGAAA
GCCGCAGAGAAGGAAGAACCCTCAGGAAGGCCTGTACAATGAACTGCAGA
AAGATAAGATGGCGGAGGCCTACAGTGAGATTGGGATGAAAGGCGAGCGC
CGGAGGGGCAAGGGGCACGATGGCCTTTACCAGGGTCTCAGTACAGCCAC
CAAGGACACCTACGACGCCCTTCACATGCAGGCCCTGCCCCCTCGCTAAt
ag
```

SEQ ID NO: 29 is the PLAP h3 CAR amino-acid
sequence (ScFv sequence bold).
M A L P V T A L L L P L A L L L H A A R P A S Q V
Q L Q E S G P G L V K P S E T L S L T C T V S G F
S L T S Y G V S W I R Q P P G K G L E W I G V I W
E D G S T N Y N P S L K S R V T I S V D T S K N Q
F S L K L S S V T A A D T A V Y Y C A R P H Y G S
S Y V G A ME Y W G A G T T V T V S S G G G G S G G
G G S G G G G S D I Q M T Q S P S S L S A S V G D
R V T I T C R A S E N I Y S Y V A W Y Q Q K P G K
A P K L L I Y N A K S L A S G V P S R F S G S G S
G T D F T L T I S S L Q P E D F A T Y Y C Q H H Y
V S P W T F G G G T K L E I K L E K P T T T P A P
R P P T P A P T I A S Q P L S L R P E A S R P A A
G G A V H T R G L D F A S D K P F W V L V V V G G
V L A C Y S L L V T V A F I I F W V R S K R S R L
L H S D Y M N M T P R R P G P T R K H Y Q P Y A P
P R D F A A Y R S R V K F S R S A D A P A Y Q Q G Q N Q L Y N E L N L G R R E E Y D V L D K R R G R
D P E M G G K P Q R R K N P Q E G L Y N E L Q K D
K M A E A Y S E I G M K G E R R R G K G H D G L Y
Q G L S T A T K D T Y D A L H M Q A L P P R Humanized PLAP-h3 VH, SEQ ID NO: 30.
Q V Q L Q E S G P G L V K P S E T L S L T C T V S
G <u>F S L T S Y G V S</u> W I R Q P P G K G L E W I G
<u>V I W E D G S T N Y *N P S L K S*</u> R V T I S V D T S
K N Q F S L K L S S V T A A D T A V Y Y C A R <u>P H</u>
<u>Y G S S Y V G A ME</u> Y W G A G T T V T V S S Humanized PLAP h3 VL, SEQ ID NO: 22

Humanized PLAP h3 scFv, SEQ ID NO: 31

Example 7. PLAP CAR with Humanized Antibody h5

SEQ ID NO: 32 is the humanized PLAP-h5 scFv
nucleotide sequence, which is inserted between Xho
and NheI sites:
```
CAG GTC CAG CTG CAA GAA TCA GGA CCA GGA CTG GTA
AAG CCG TCC GAA ACG CTC AGT TTG ACG TGC ACCGTG TCA
GGC GGC AGT ATA ACA TCC TAC GGG GTC AGC TGG ATC
CGC CAA CCG CCT GGG AAA GGC CTC GAATGG ATA GGG GTG
ATT TGG GAA GAC GGG AGT ACA AAC TAC AAT CCG AGT
TTG AAG AGC CGC GTG ACG ATAAGC GTT GAC ACA AGT AAG
AAC CAG TTT AGT CTC AAA CTC TCC AGT GTA ACA GCT
GCT GAT ACA GCA GTGTAC TAC TGC GCT CGA CCT CAC TAT
GGC TCT AGT TAC GTC GGA GCT ATG GAA TAC TGG GGG
GCT GGC ACTACA GTT ACT GTG AGT TCC GGT GGC GGA GGA
TCT GGT GGC GGT GGT TCC GGT GGG GGA GGA TCC GAC
ATACAG ATG ACG CAG TCC CCA AGT AGC TTG AGC GCA TCA
GTA GGA GAC AGA GTC ACC ATT ACA TGC CGA GCT TCC
GAG AAC ATC TAC AGT TAC GTA GCT TGG TAT CAG CAA
AAA CCG GGG AAA GCA CCT AAA CTT CTC ATCTAC AAC GCA
AAA AGT CTG GCG AGT GGG GTT CCC TCA AGG TTC TCT
GGA AGC GGG AGC GGA ACG GAT TTTACT CTG ACT ATT AGT
AGT TTG CAA CCA GAA GAC TTT GCC ACG TAC TAC TGT
CAG CAT CAC TAT GTC TCCCCT TGG ACG TTC GGA GGA GGG
ACC AAG CTC GAA ATC AAA (SEQ ID NO: 31)
```
Humanized PLAPh5 CAR amino-acid sequence (SEQ ID
NO: 33)
M A L P V T A L L L P L A L L L H A A R P A S Q V
Q L Q E S G P G L V K P S E T L S L T C T V S G G
S I T S Y G V S W I R Q P P G K G L E W I G V I W -continued

EDGSTNYNPSLKSRVTISVDTSKNQ

FSLKLSSVTAADTAVYYCARPHYGS

SYVGAMEYWGAGTTVTVSSGGGGSG

GGGSGGGGSDIQMTQSPSSLSASVG

DRVTITCRASENIYSYVAWYQQKPG

KAPKLLIYNAKSLASGVPSRFSGSG

SGTDFTLTISSLQPEDFATYYCQHH

YVSPWTFGGGTKLEIKLEKPTTTPA

PRPPTPAPTIASQPLSRPEASRPA

AGGAVHTRGLDFASDKPFWVLVVVG

GVLACYSLLVTVAFIIFWVRSKRSR

LLHSDYMNMTPRRPGPTRKHYQPYA

PPRDFAAYRSRVKFSRSADAPAYQQ

GQNQLYNELNLGRREEYDVLDKRRG

RDPEMGGKPQRRKNPQEGLYNELQK

DKMAEAYSEIGMKGERRRGKGHDGL

YQGLSTATKDTYDALHMQALPPR

Humanized PLAP-h5 VH, SEQ ID NO: 34. CDR 1, 2, 3, underlined.
QVQLQESGPGLVKPSETLSLTCTVS*GSITSYG*VSWIRQPPGKGLE

*WIGVIWEDGSTNYNPSLKS*RVTISVDTSKNQFSLKLSSVTAADTAVYYCA

RPHYGSSYVGAMEYWGAGTTVTVSS

Humanized PLAP h5 VL, SEQ ID NO: 22

Humanized PLAP h5 scFv, SEQ ID NO: 35
QVQLQESGPGLVKPSETLSLTCTVS

GGSITSYGVSWIRQPPGKGLEWIGV

IWEDGSTNYNPSLKSRVTISVDTSK

NQFSLKLSSVTAADTAVYYCARPHY

GSSYVGAMEYWGAGTTVTVSSGGGG

SGGGGSGGGGSDIQMTQSPSSLSAS

VGDRVTITCRASENIYSYVAWYQQK

PGKAPKLLIYNAKSLASGVPSRFSG

SGSGTDFTLTISSLQPEDFATYYCQ

HHYVSPWTFGGGTKLEIK

Example 8. PLAP has Negative Expression in Most Normal Tissues and Expressed in Gastro-Intestinal Cancers We performed IHC staining with PLAP antibody on placenta, testis, colon cancer, ovarian cancer and other normal or malignant tissues from different types of cancer. Placenta had highest staining, testis, colon and ovarian cancer were positive, while other type of cancer (breast, lung, prostate cancer) were negative as well as normal tissues: pancreas, tonsil, rectum, muscle, esophagus, brain and other tissues. In addition, we evaluated mRNA expression of PLAP expression in silico across 1457 different malignant cell lines, including 63 colon cancer cell lines using the Cancer Cell Line Encyclopedia (CCLE). Expression of PLAP was high in gastro-intestinal (GI) cancers: cancers of esophagus, upper aerodigestive organs, stomach, pancreatic and colon cancers. We also performed analysis using Genotype-Tissue Expression (GTEx) database of PLAP expression in nonmalignant normal tissues. PLAP mRNA had minimal expression in many normal tissues (many had 0 TMP (transcript per million kb) mRNA level. In contrast when we analyzed EpCAM as a positive control, its expression was medium-high in many normal tissues with medium expression in colon 445 TMP (transcript per million kb), small intestine 391 and in thyroid 259. Thus, PLAP has negative expression in most normal tissues in contrast to other tumor-associated markers.

Figure 3:
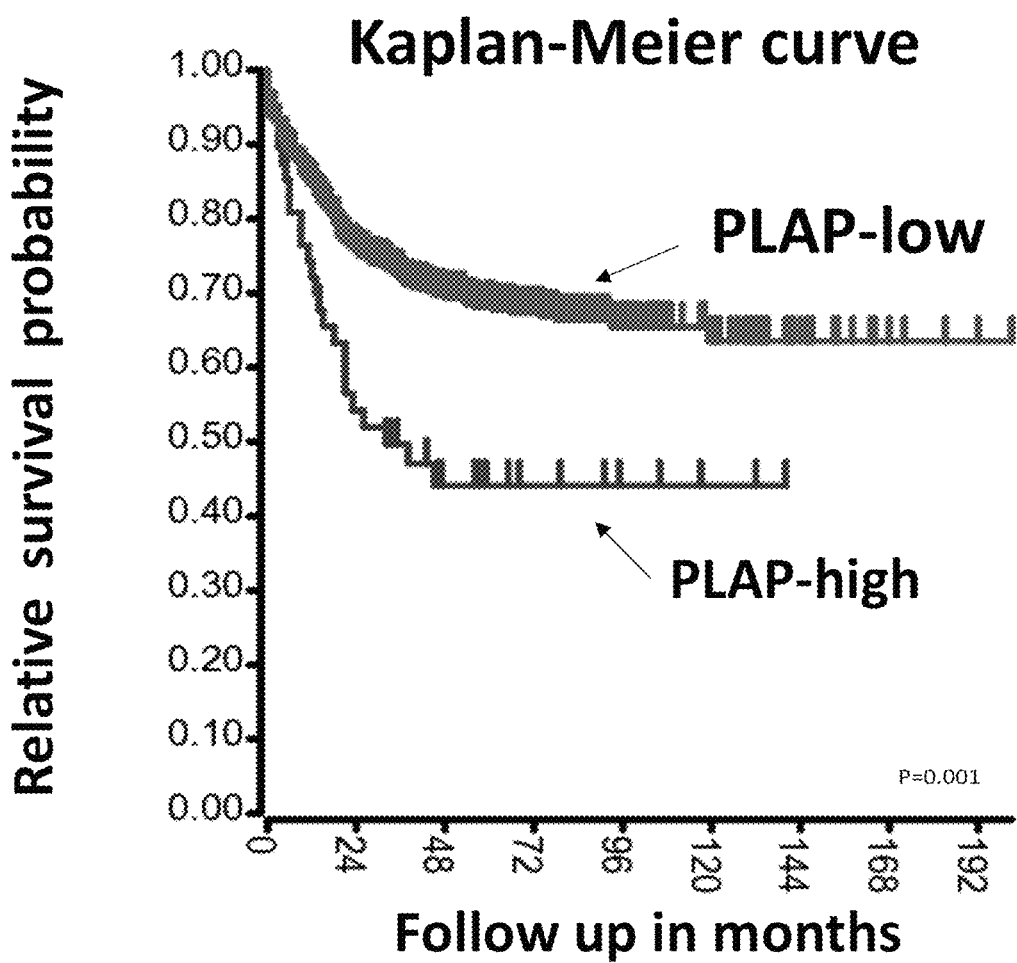
FIG. 3 shows relapse free survival probability vs. months in follow up in patients with high and low PLAP expression.

Example 9. PLAP is Expressed in Primary Colon Tumors and Colon Cancer Cell Lines We performed IHC staining with mouse PLAP antibody using 106 primary colon cancer tumors, and found PLAP expression in 25 of 106 samples that is 23.8% of all colon cancer tumors. We also tested PLAP expression by R2 genomics analysis and visualization platform in 557 primary colon cancer tumors and performed correlation with patient outcome (FIG. 3). Patients with high PLAP expression had shorter survival than patients with low PLAP expression demonstrating that PLAP expression can correlate with poor prognosis in colon cancer. These data show that PLAP is overexpressed in primary colon cancer tumors.

Figure 4A:
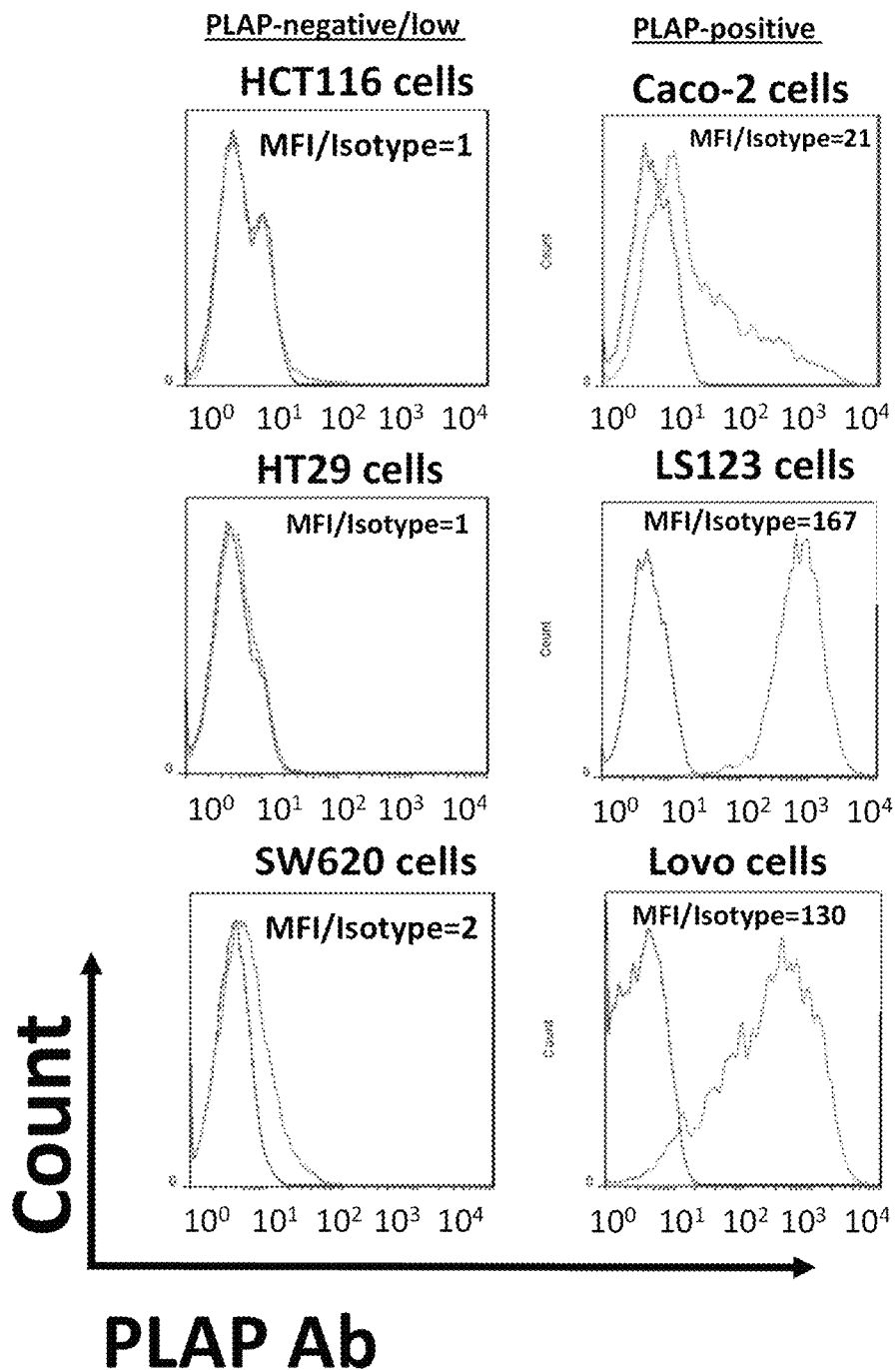
FIG. 4A shows expression of PLAP in several colon cancer cell lines by FACS analysis. PLAP-negative and PLAP-positive cell lines are shown. MFI (Mean fluorescent intensity)/isotype ratio is shown for each cell line.
Figure 4B:
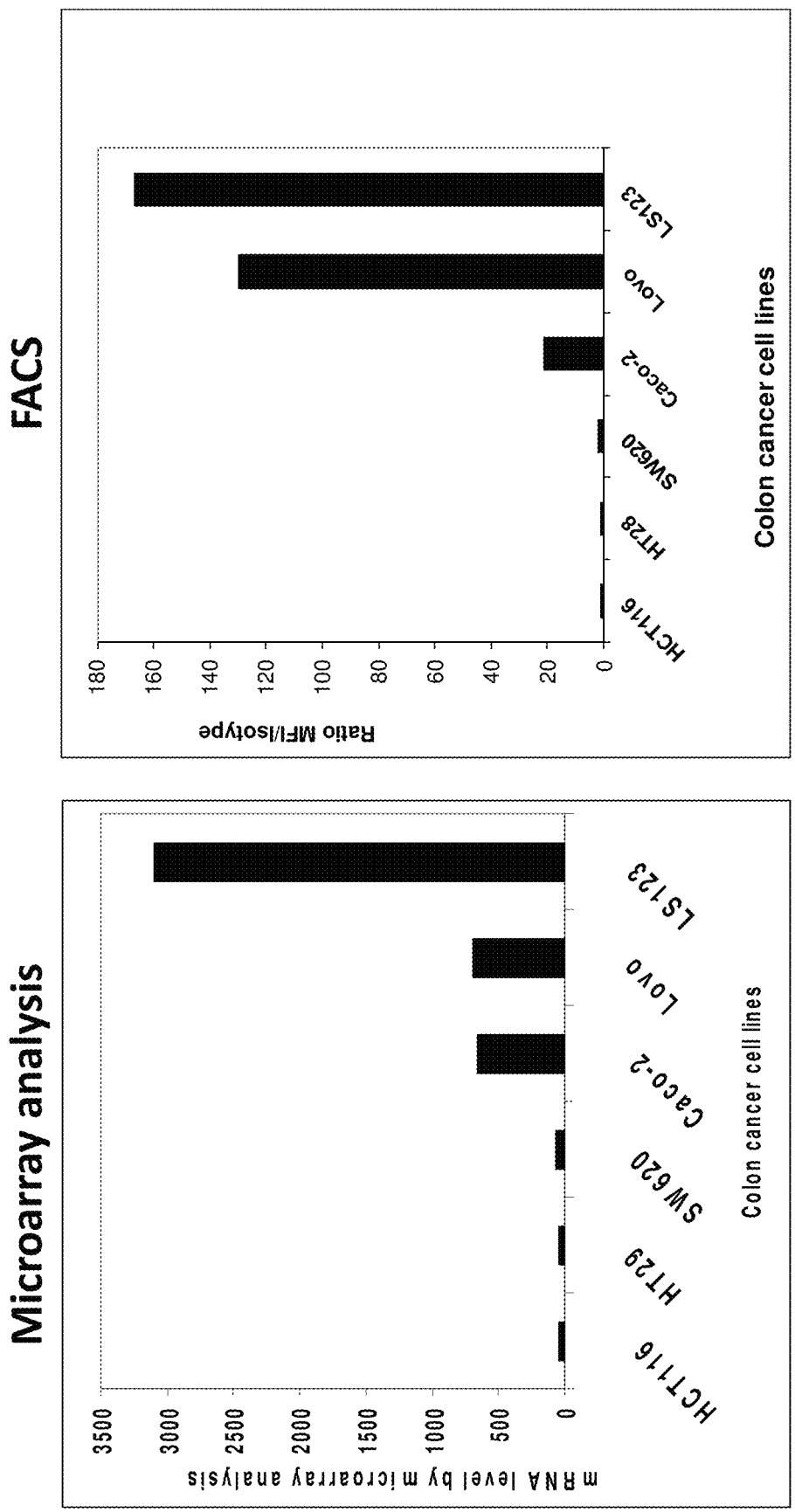
FIG. 4B shows three positive and three negative cell lines by mRNA and protein. PLAP-negative: HCT116, SW620 and HT-29 cell lines; and PLAP-positive: Lovo, Caco-2, LS123 cell lines.

In addition, we tested PLAP mRNA level in 117 colon cancer cell lines using microarray assay, and detected that 21.3% of colon cancer cell lines expressed PLAP mRNA. We performed FACS assay and detected PLAP in colon cancer cell lines with high PLAP mRNA expression: Lovo, Caco-2 and LS123 cell lines (FIG. 4A). We detected minimal PLAP expression in PLAP-negative colon cancer cell lines such as HCT116, HT-29 and SW620 cell lines (FIG. 4B). Thus, PLAP mRNA and PLAP protein levels corresponded to each other (FIG. 4B). To confirm specificity of PLAP antibody H17E2 we detected that it recognized purified recombinant PLAP protein with Kd=3.2 nM by BLI BLITZ analysis. PLAP antibody H17E2 also recognized PLAP protein expressed in 293 cells. Thus, PLAP is expressed in colon cancers and PLAP antibody detects PLAP antigen suggesting that it can be used for CAR-T therapy.

Figure 5A:
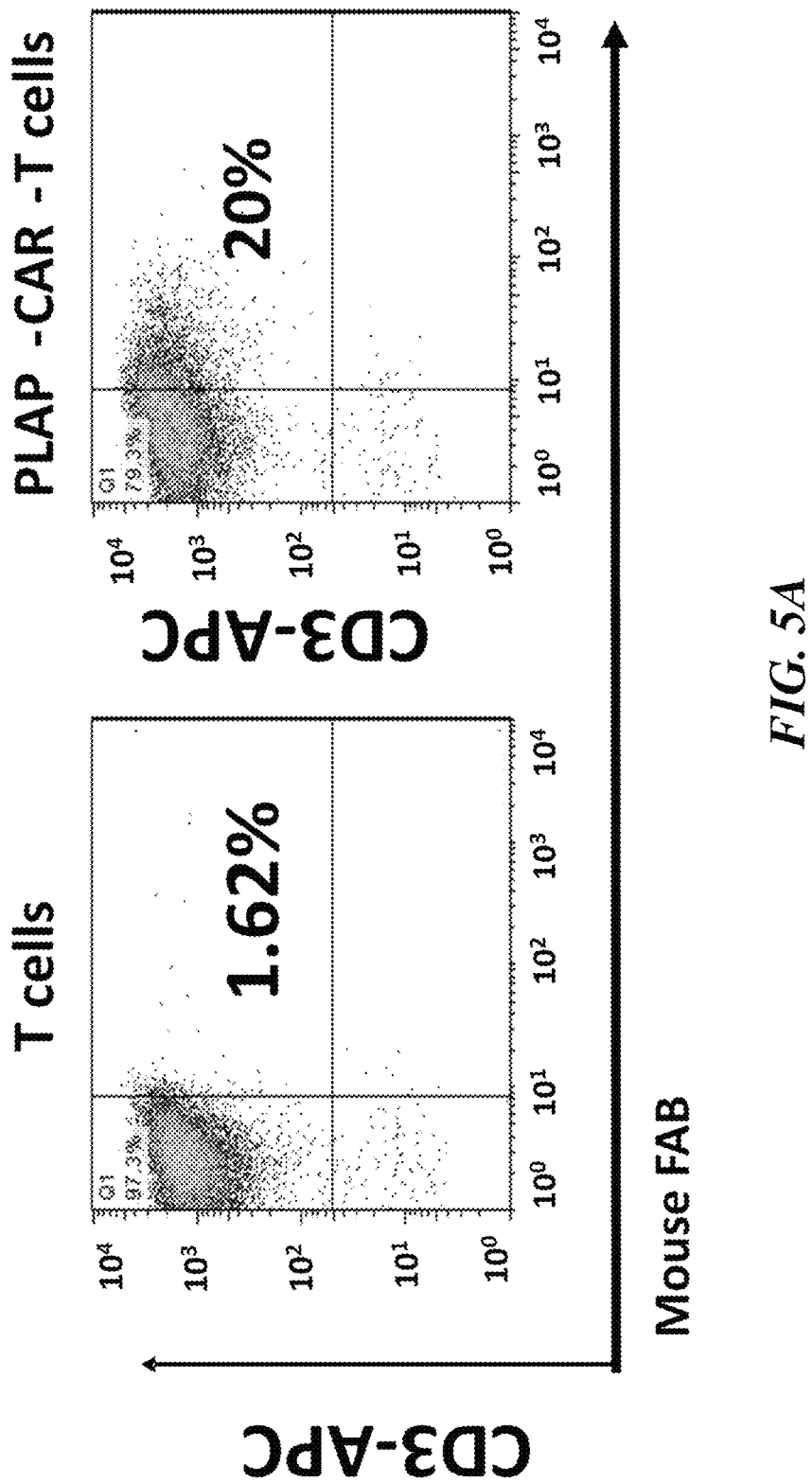
FIG. 5A shows that PLAP-CAR-T cells specifically killed PLAP-positive colon cancer cells more significantly compared to T and Mock-CAR-T cells. Real-time cytotoxicity assay (RTCA) was used as described in Materials and Methods. CAR-T cells to target cells ratio (E:T) is 10:1.

Example 10. PLAP-CAR-T Cells Specifically Kill PLAP-Positive Cells but not PLAP-Negative Cells We designed second generation CAR construct using mouse monoclonal PLAP antibody ScFv, CD8 alpha hinge, CD28 transmembrane and co-stimulatory domain and CD3 activation domain (FIG. 2). We prepared lentiviral PLAP-CAR and Mock CAR with intracellular protein ScFv, and transduced T cells to generate CAR-T cells. The PLAP-CAR-T cells had >200-fold expansion that was similar as Mock-CAR-T cells or T cells. CAR-T positive cells were detected by FACS with mouse FAB antibody (FIG. 5A).

Figure 5B:
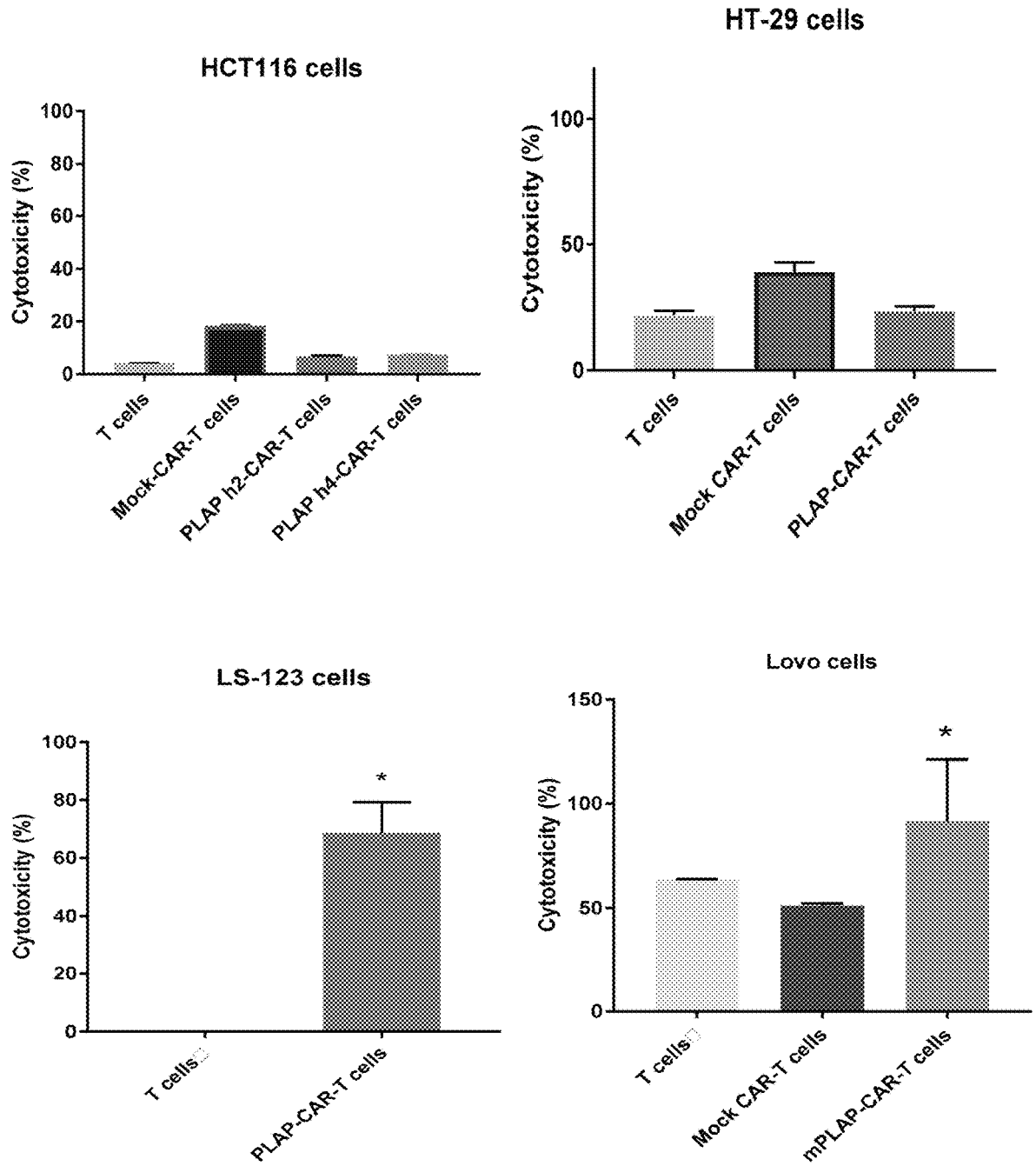
FIG. 5B shows that PLAP-CAR-T cells had significant killing activity compared with normal T cells against Lovo and LS-123 colon cancer target cells but did not have significant killing activity with PLAP-negative HCT116 and HT29 colon cancer cell lines.
Figure 5C:
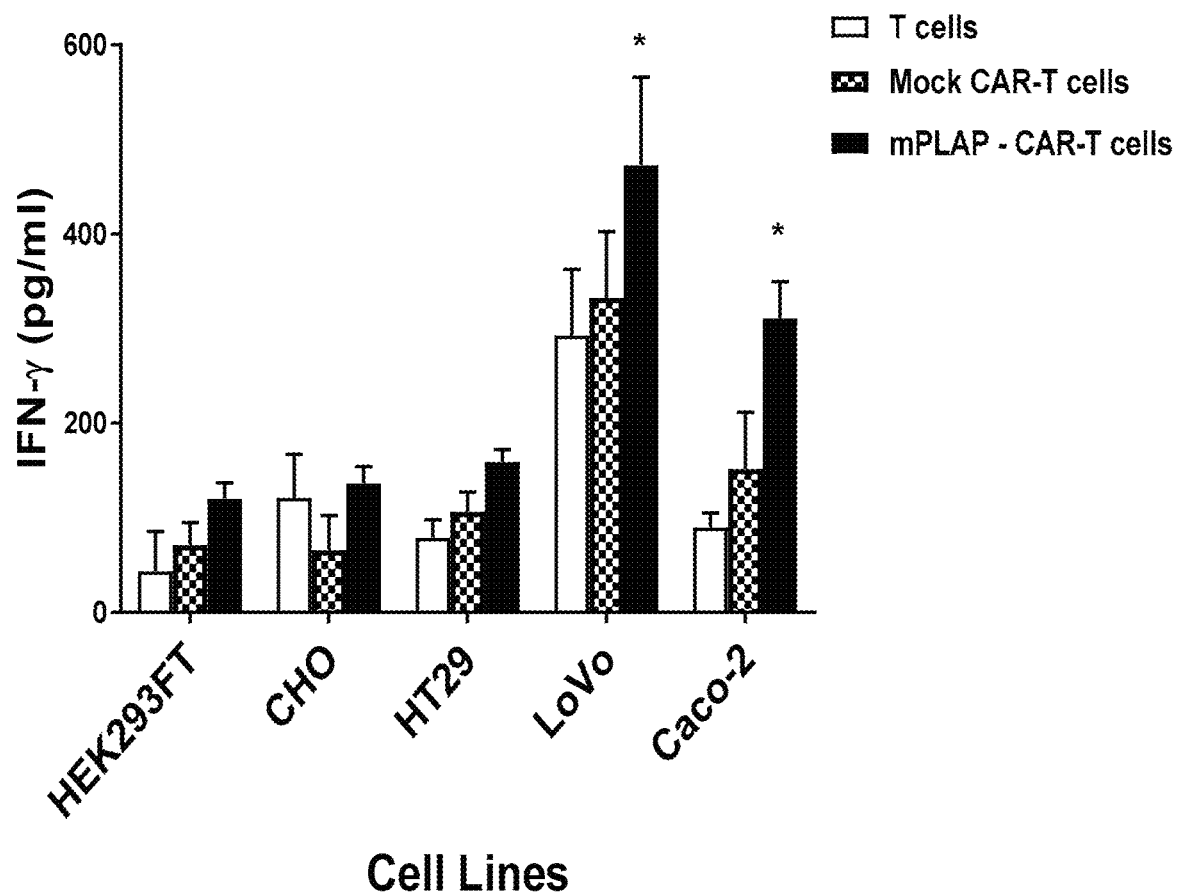
FIG. 5C shows that CAR-T secreted significant level of IFN-gamma against PLAP-positive cells. Bars show average level of IFN-gamma from three independent experiments. p<0.05, Student's t-test.

PLAP-CAR-T cells were used in a Real-time cytotoxicity assay (RTCA) with PLAP-positive target colon cancer cell lines: Lovo, and LS-123; and with PLAP-negative colon cancer cell lines: HT29, and HCT116. PLAP-CAR-T cells had significant killing activity compared with normal T cells against Lovo and LS-123 colon cancer target cells but did not have significant killing activity with PLAP-negative HCT116 and HT29 colon cancer cell lines (FIG. 5B). In addition, all CAR-T cells cell lines secreted significant level of IFN-gamma against PLAP-positive target colon cancer cells but not against PLAP-negative colon cancer cells (FIG. 5C). There were also no significant secretion of IFN-gamma against normal 293 and CHO cell lines (FIG. 5C). These data show specific functional activity of PLAP-CAR-T cells against PLAP-positive colon cancer cell lines.

Figure 6A:
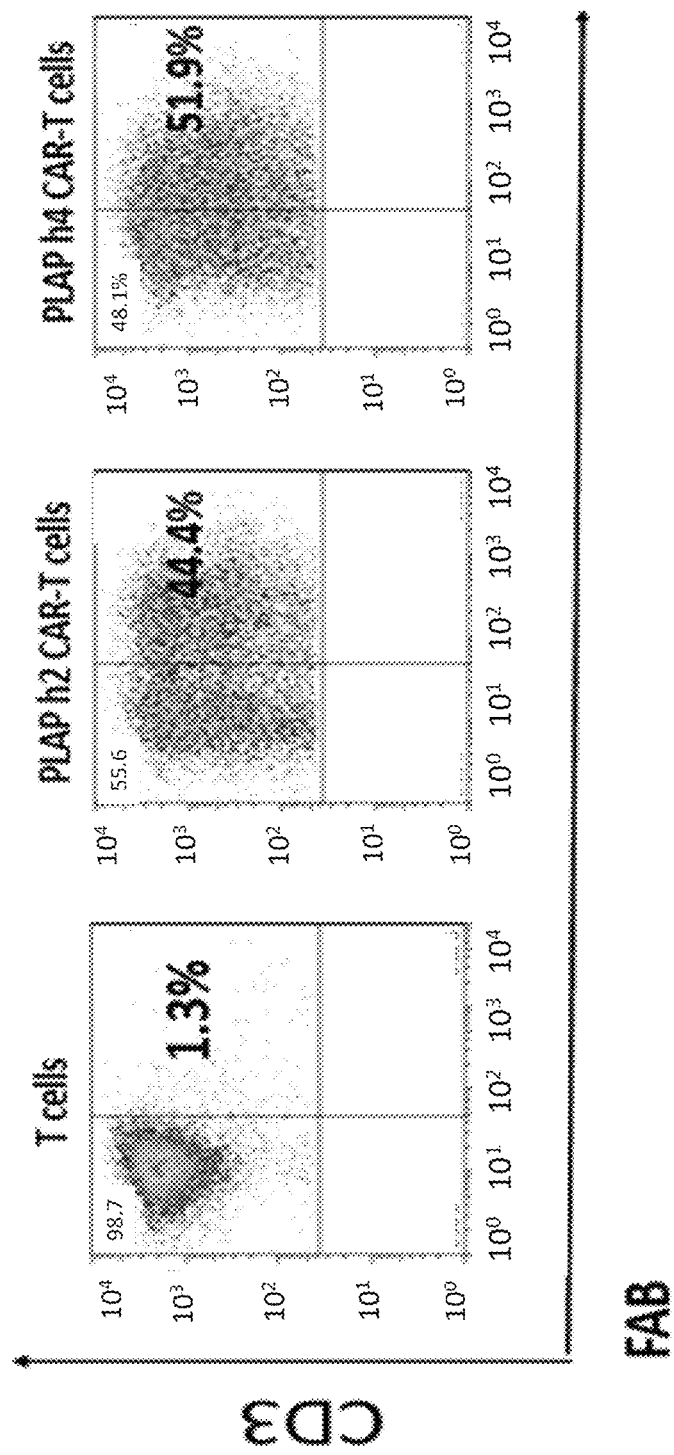
FIG. 6A shows that PLAP h2- and PLAPh4-CAR-T positive cells were detected with FAB antibody by FACS.
Figure 6B:
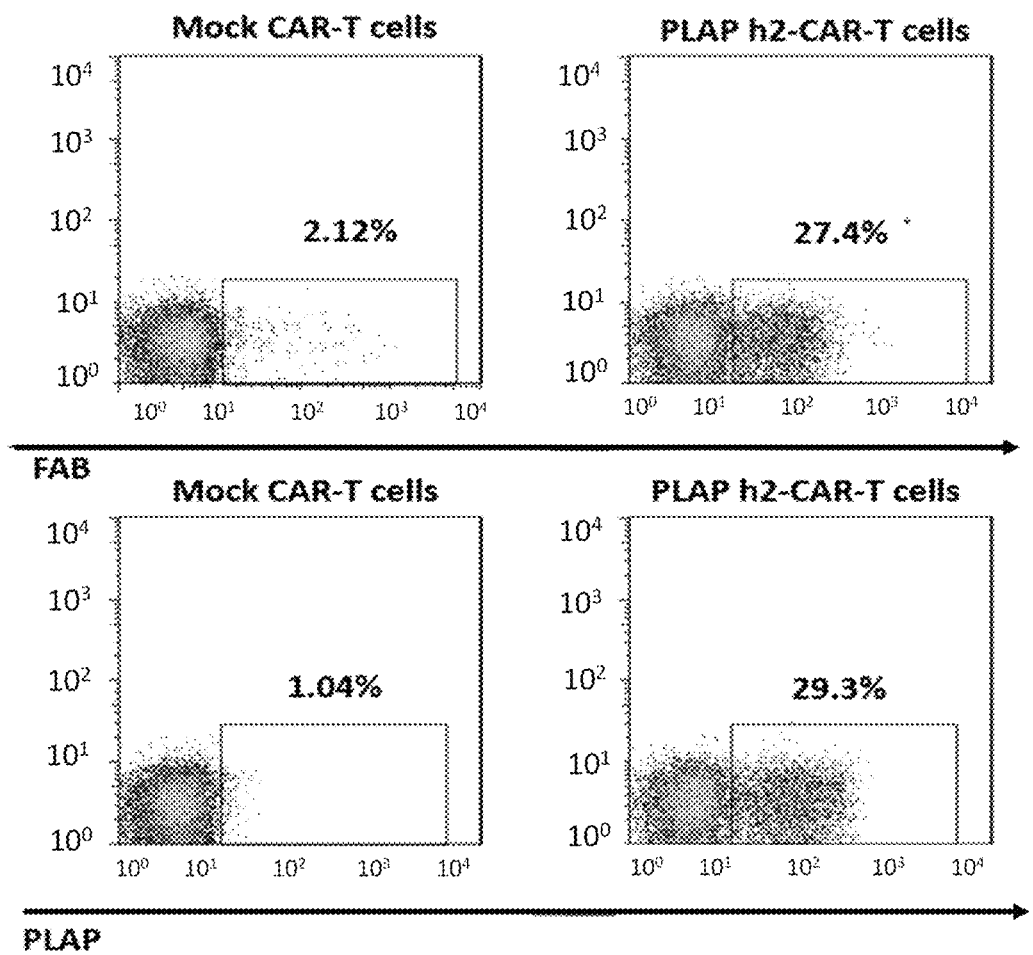
FIG. 6B shows that PLAP CAR-T positive cells were detected by FACS with biotinylated recombinant PLAP protein.

Example 11. Humanized PLAP-CAR-T Cells (h2 and h4) Specifically Kill PLAP-Positive Cells To improve mPLAP-CAR-T cells, we humanized mouse PLAP ScFv, and generated humanized PLAP-CAR cells (FIG. 2). The humanized PLAP h2 had 44.1% and PLAP h4 CAR-T cells had 50.6% of CAR-positive cells which were detected by FACS with FAB antibody (FIG. 6A). To confirm specificity of PLAP-CAR-T cells to PLAP antigen, we performed FACS using biotinylated PLAP recombinant protein (FIG. 6B). Biotinylated PLAP protein recognized PLAP-CAR as well as FAB antibody demonstrating specific binding of humanized PLAP-ScFv to PLAP antigen (FIG. 6B).

PLAP-CAR-T cells (h2 and h4) significantly killed PLAP-positive cells compared to Mock control CAR-T cells and did not kill significantly PLAP-negative cells in RTCA assay (FIG. 6C). In addition, PLAP-CAR-T cells secreted significant level of IFN-gamma, IL-2 and IL-6 against PLAP-positive colon cancer cells but not against PLAP-negative colon cancer cells (FIG. 6D). These data show that humanized PLAP-CAR-T cells specifically and effectively killed PLAP-positive colon cancer cells.

Figure 7A:
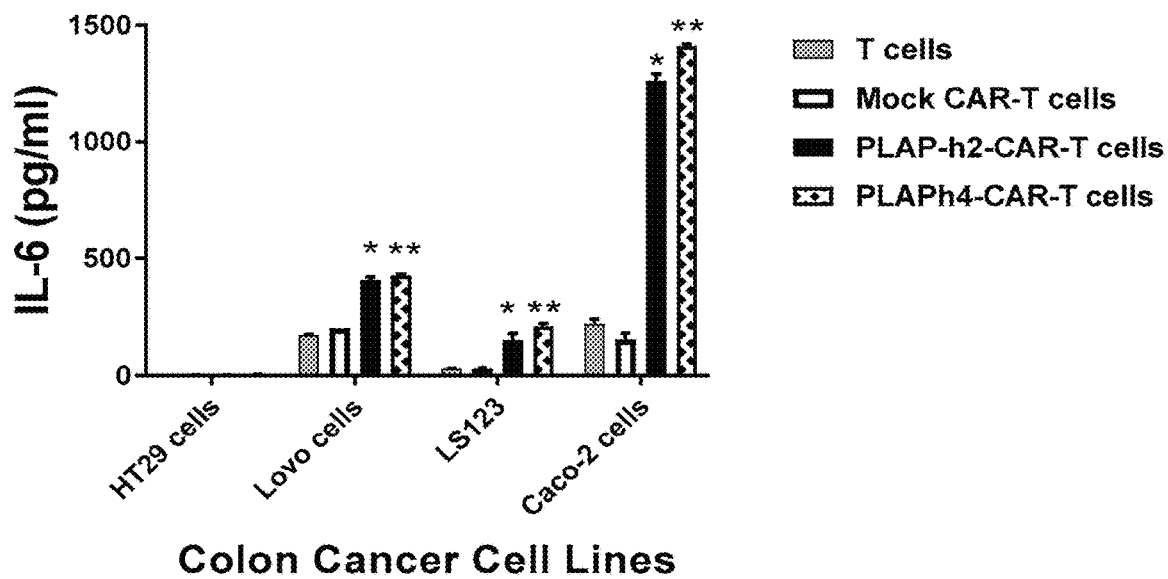
FIG. 7A shows that humanized PLAP-CAR-T cells significantly decreased Lovo xenograft tumor growth. The volume of CAR-T cell-treated tumors was significantly less than with Mock control treated cells. p<0.05, Student's t-test.
Figure 7A:
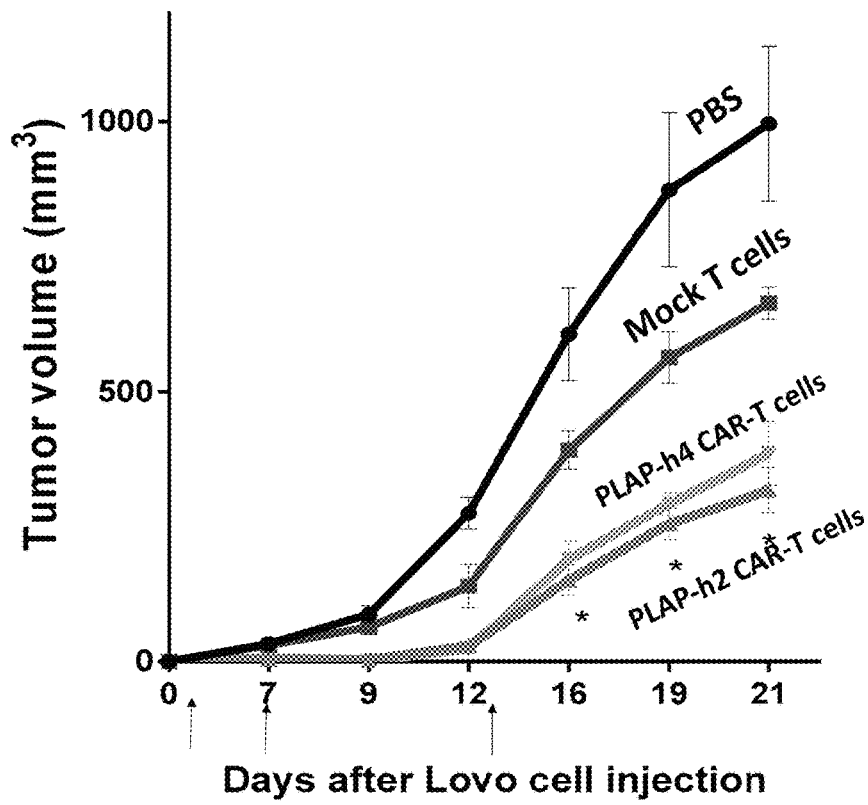
Figure 7B:
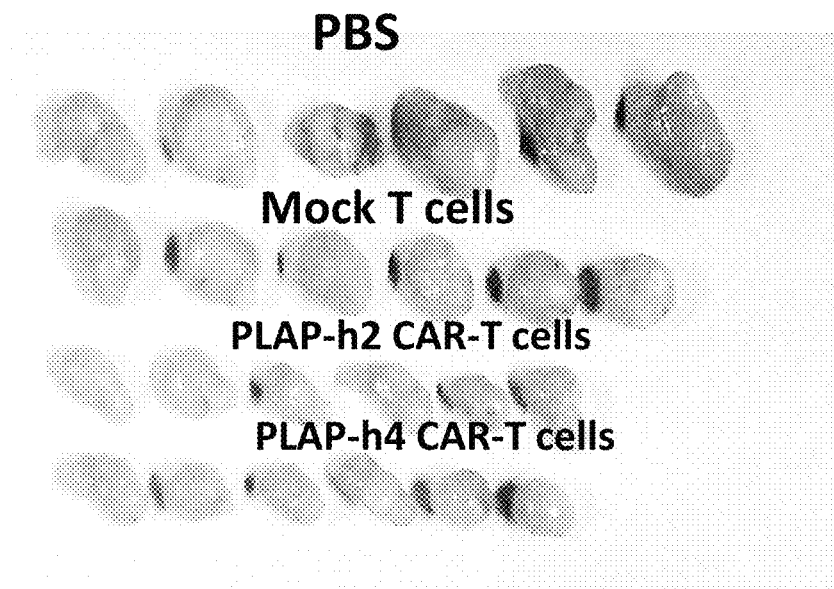
FIG. 7B shows that the size of humanized PLAP-CAR-T cell treated tumors was significantly less than in control mice. p<0.05, Student's t-test.
Figure 7C:
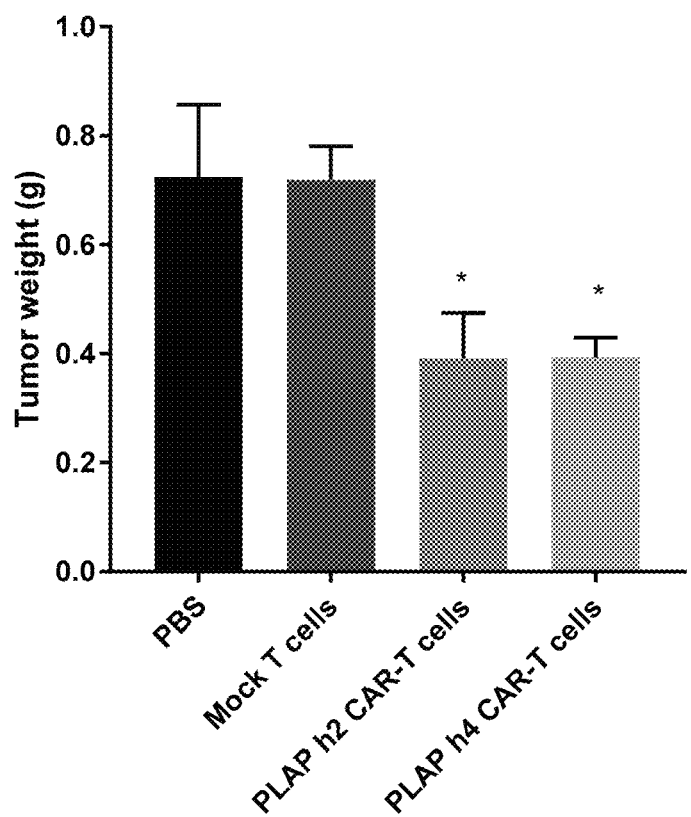
FIG. 7C shows that tumor weight was significantly less in hPLAP-CAR-T treated mice than in control mice. P<0.05, Student's t-test.

Example 12. Humanized PLAP-CAR-T Cells (h2 and h4) Significantly Decrease Colon Cancer Xenograft Tumor Growth We analyzed PLAP-CAR-T cell efficacy in Lovo xenograft mouse model in vivo (FIG. 7). Lovo cancer cells were injected subcutaneously into NSG mice, and then CAR-T cells were injected at days 1, 7 and 13. Humanized PLAP h2 and PLAPh4-CAR-T cells significantly decreased Lovo xenograft tumor growth (FIG. 7A). The tumor size (FIG. 7B) and tumor weight (FIG. 7C) were significantly reduced by humanized PLAP-CAR-T cells. The mice body weight did not decrease by PLAP-CAR-T cells suggesting negative toxicity of CAR-T cells. Human T cells and CAR-T cells were detected in mouse blood with anti-human CD3 antibody at day 16 demonstrating persistence of humanized PLAP-CAR-T cells in vivo.

Figure 7D:
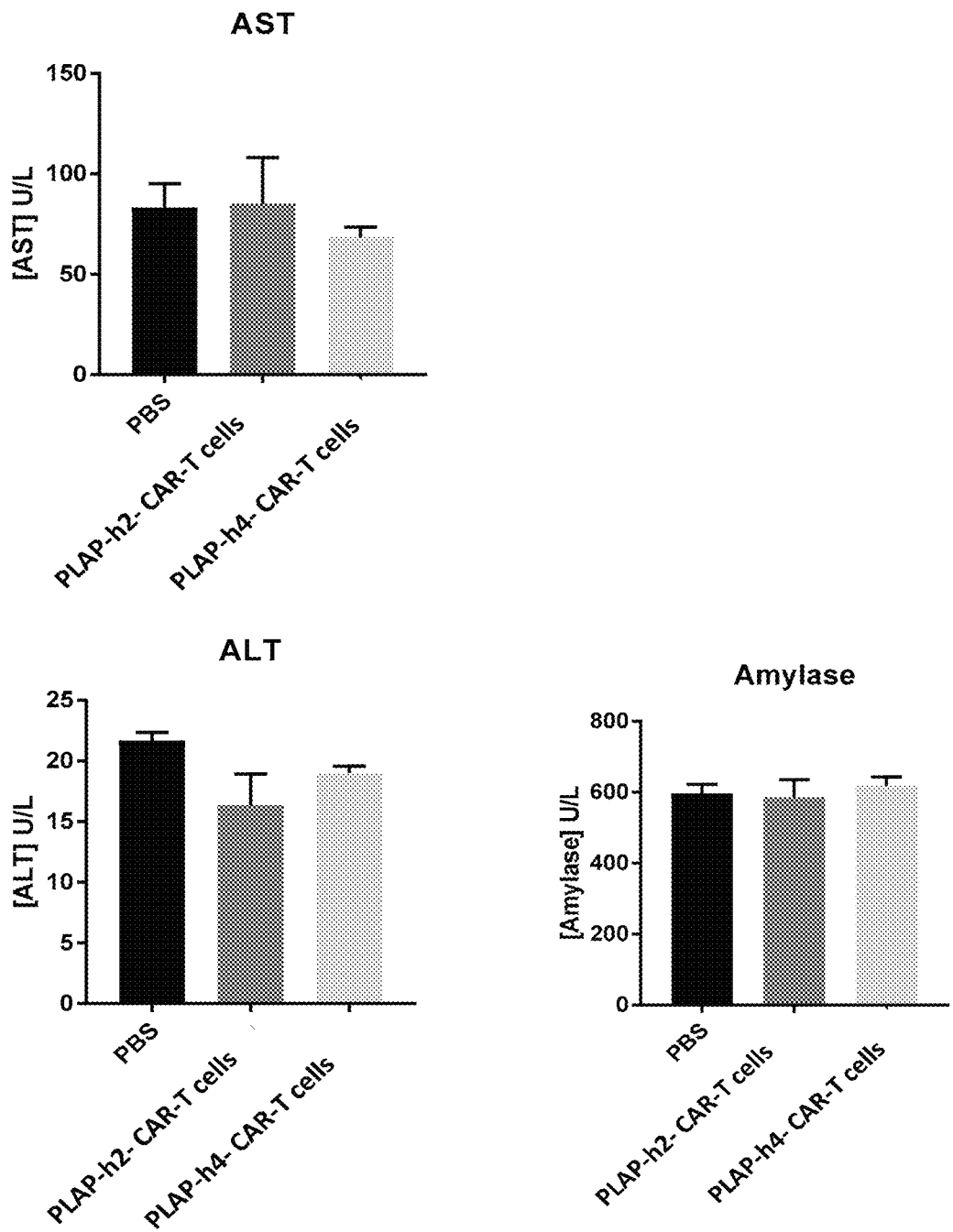
FIG. 7D shows that AST, ALT, and amylase levels were not significantly affected in blood serum of humanized PLAP-CAR-T cell treated mice. The samples were analyzed as described in Materials and Methods.

To test toxicity of CAR-T cells, we performed analysis of several enzymes from mouse blood serum: AST, ALT and amylase (FIG. 7D). There were no toxic effects of PLAP-CAR-T cells on these enzymes (FIG. 7D) suggesting no toxicity of PLAP-CAR-T cells in vivo. Thus, PLAP-CAR-T cells have high efficacy with no toxicity in vivo.

Example 13. Humanized PLAP-CAR-T Cells (h5) Specifically Kill PLAP-Positive Cells Real-time cytotoxicity assay (RCTA) and IFN-γ assay were performed according to Example 1.

Figure 8B:
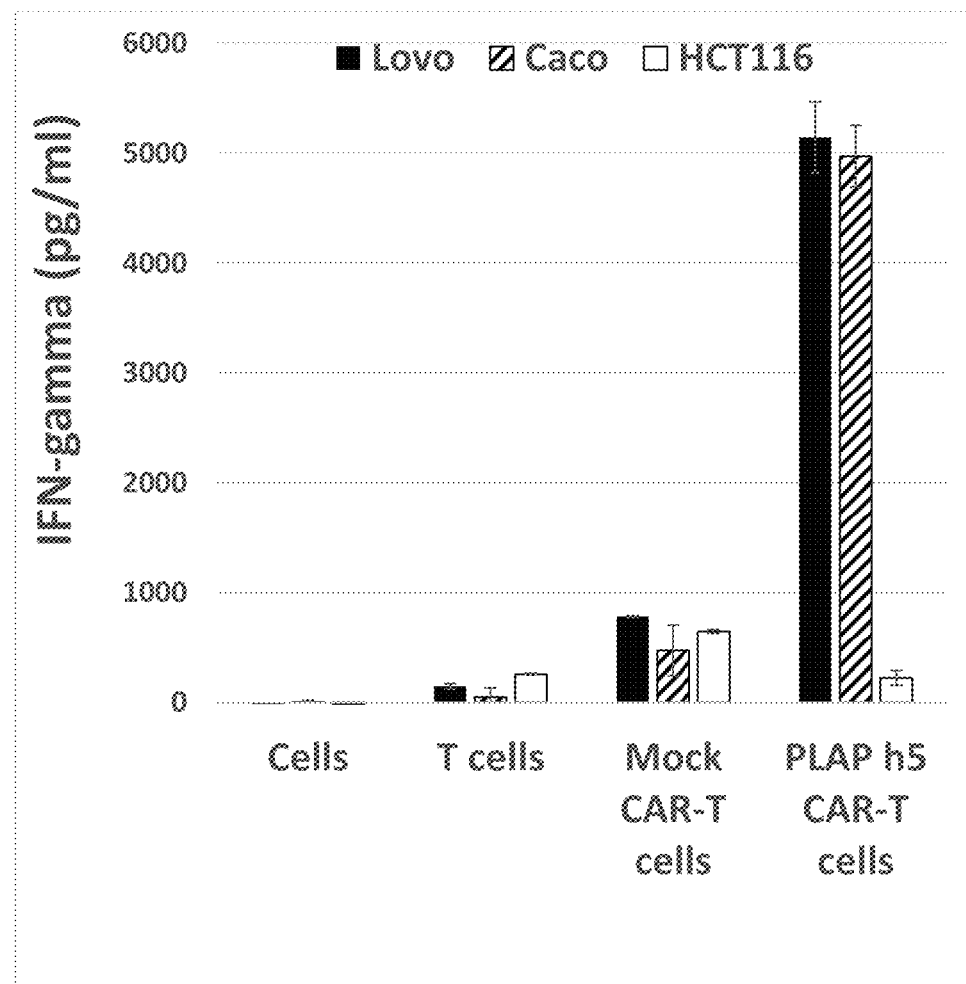
FIG. 8B shows that PLAP h5-CAR-T cells secreted significant higher level of IFN-γ, against PLAP-positive colon cancer cells (Caco-2 cells and Lovo cells), but not PLAP-negative colon cancer cells (HCT116).

FIG. 8A shows that PLAP h5-CAR-T cells significantly killed PLAP-positive colon cancer cells (Caco-2 cells and Lovo cells) compared to T cells and target cells alone. PLAP h5-CAR-T cells (h5) did not kill PLAP-negative colon cancer cells (HCT116) by RTCA. FIG. 8B shows that PLAP h5-CAR-T cells secreted significant higher level of IFN-γ, against PLAP-positive colon cancer cells (Caco-2 cells and Lovo cells), but not against PLAP-negative colon cancer cells (HCT116).

These data show that humanized PLAP h5-CAR-T cells specifically and effectively killed PLAP-positive colon cancer cells and specifically secreted IFN-gamma against PLAP-positive colon cancer cell line.

Example 14. Combination of PLAP-CAR-T Cells with Checkpoint Inhibitors Increased Activity of CAR-T Cells We tested expression of PDL-1 on colon cancer target cells in response to hPLAP-CAR-T cells when we co-cultured them for 24 hours (FIG. 9A). We also used IFN-γ, a known agent to induce PDL-1 in cancer cells [35] as a positive control for PDL-1 induction. The PLAP-negative cells HT29 and HCT116 cells activated PDL-1 in response to hPLAP-CAR-T cells similarly in response to T cells, Mock-CAR-T cells and IFN-γ (FIG. 9A). In contrast, PLAP-positive Lovo cells significantly up-regulated PDL-1 in response to CAR-T cells versus T and Mock CAR-T cells and more than in response to IFN-gamma (FIG. 9A). Caco-2 cells did not activate PDL-1 in response to IFN-gamma and also to PLAP-CAR-T cells (FIG. 9A). These data show that CAR-T cells caused significant up-regulation of PDL-1 in PLAP-positive cancer cells and that PLAP-positive cancer cells differ in their up-regulated PDL-1 levels, and that PLAP-CAR-T cells did not cause significant up-regulation of PDL-1 in PLAP-negative target colon cancer cells compared with Mock-Car-T cells and non-transduced T cells.

Since Lovo cells activated PDL-1 significantly more in response to PLAP-CAR-T cells than in response to IFN-gamma (FIG. 9A), we focused on PDL-1 up-regulation in this cell line in more detail. The expression of PDL-1 was low at one and 4 hours after addition of CAR-T cells and resulted in significant up-regulation of PDL-1 at 24 hours (FIG. 9B), and its level did not increase more at 49 hours (not shown). We added different doses of PLAP-CAR-T cells to Lovo cells, co-cultured for 24 hours, and detected dose-dependent response in terms of PDL-1 up-regulation in Lovo colon cancer target cells in response to hPLAP CAR-T cells (FIG. 9C). PDL-1 was significantly up-regulated even at small dose of PLAP-CAR-T cells added to target cancer cells (Effector to target cell ratio, E:T=0.3:1) (FIG. 9C).

Figure 9E:
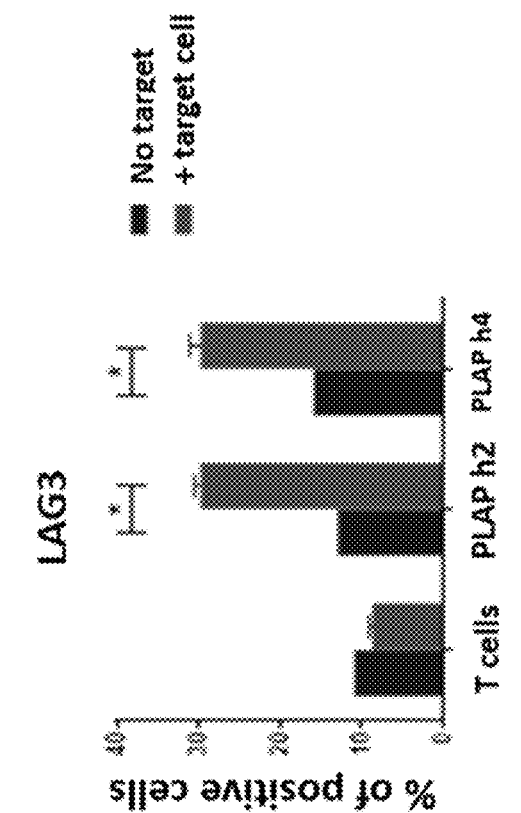
FIG. 9E shows that LAG-3 expression was upregulated after co-incubation with PLAP-positive cells. LAG-3 level is significantly up-regulated versus Mock or CAR-T cells without target cells. p<0.05, Student's t-test.
Figure 9D:
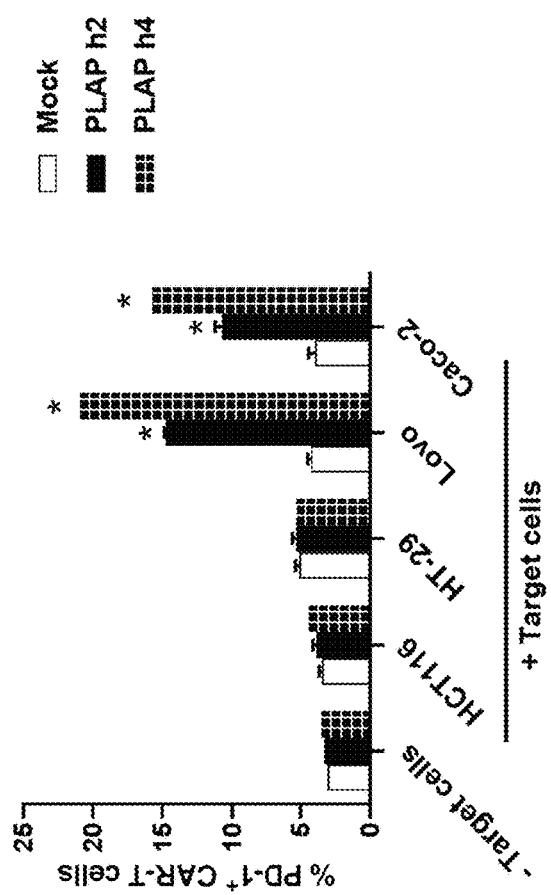
FIG. 9D shows that PD-1 expression was induced in CAR-T cells after co-incubation with PLAP-positive target cells. FACS analysis is shown with PD-1 antibody before and after co-incubation with target cells. PD-1 level is significantly increased. p<0.05, Student's t-test.

To evaluate up-regulation of checkpoint proteins in CAR-T cells after co-incubation with colon cancer cells, we tested several checkpoint proteins: PD-1, TIM-3, TIGIT and LAG-3. Only PD-1 was significantly up-regulated in CAR-T cells after co-culture with PALP-positive colon cancer target cells than before co-culture (FIG. 9D). PD-1 protein level was up-regulated in co-culture with PLAP-positive cells (Caco-2 and Lovo cells) but not with PLAP-negative HCT116 and HT29 cells (FIG. 9D). LAG-3 was also significantly upregulated after co-culture with Lovo cancer cell line (FIG. 9E). Thus, PLAP-positive target cells up-regulated PDL-1, and PLAP-CAR-T cells up-regulated PD-1 or LAG-3 expression.

Figure 9G:
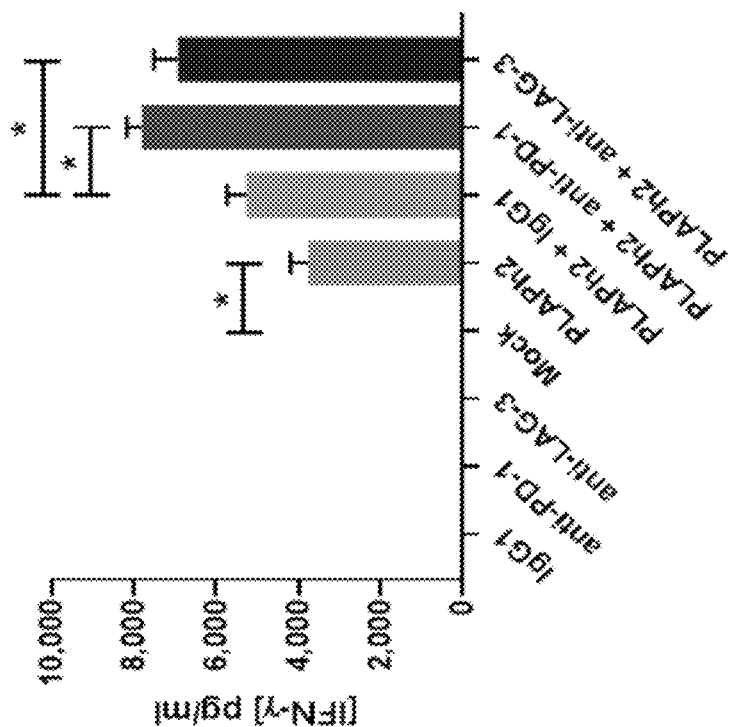
FIG. 9G shows that the secretion of IFN-gamma by PLAP-CAR-T cells in combination with PD-1 or LAG-3 antibody significantly increased versus PLAP-CAR-T cells alone or antibodies alone. *p<0.05, Student's one-tailed t-test vs PLAP-CAR-T cells plus isotype antibody.
Figure 9F:
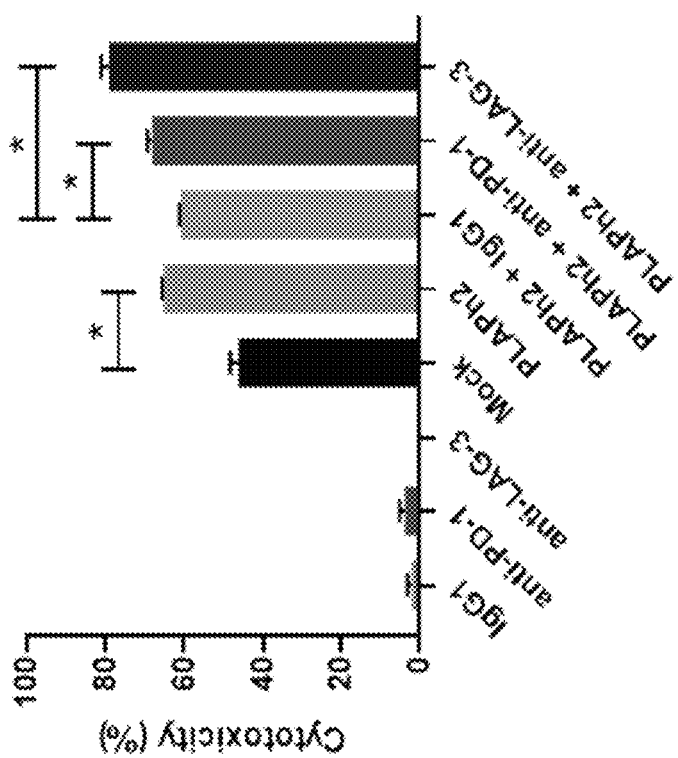
FIG. 9F shows that the combination of PLAP-CAR-T cells with PD-1 or LAG-3 antibody increases cytotoxicity of CAR-T cells against target cells. RTCA assay was performed with PLAPh2-CAR-T cells at 3:1 either alone or in combination with PD-1 or PDL-1 antibody. Quantification of RTCA is shown after overnight co-incubation with Lovo target cells.

To test checkpoint inhibitors in combination with PLAP-CAR-T cells, we used PLAP-h2-CAR-T cells in combination with either PD-1 antibody or LAG-3 antibody and performed RTCA assay with Lovo target cells (FIG. 9F). There was significant up-regulation of cytotoxicity PLAP-CAR-T cells in combination with PD1 or LAG3 antibody versus PLAP-CAR-T cells alone with isotype antibody or versus PD-1 or LAG3 antibody alone (FIG. 9F). The combination of PLAP-CAR-T cells with either PD-1 antibody, or LAG-3 antibody significantly increased secretion of IFN-gamma versus each treatment alone in Lovo cells (FIG. 9G). The increased secretion of IFN-gamma was also observed when PLAP-CAR-T cells with PD-1 antibody were co-cultured with pre-treated IFN-g to up-regulate PDL-1 before treatment confirming data above (not shown). Thus, combination of hPLAP-CAR-T cells with checkpoint inhibitors (PD1 or LAG3 antibodies) can be an effective approach to induce efficacy of PLAP-CAR-T cells with increased IFN-gamma secretion against colon cancers.

REFERENCES

1. Eshhar, Z., et al. *Cancer J* 2014, 20, 123-126.
2. Maus, M. V., et al. *Clin Cancer Res* 2016, 22, 1875-1884.
3. Locke, F. L., et al. *Lancet Oncol* 2019, 20, 31-42.
4. Locke, F. L., et al. *Mol Ther* 2017, 25, 285-295.
5. Grupp, S. A. *Best Pract Res Clin Haematol* 2014, 27, 222-228.
6. Eshhar, Z., et al. *Br J Cancer Suppl* 1990, 10, 27-29.
7. Golubovskaya, V., et al. *Cancers* (Basel) 2016, 8.
8. Golubovskaya, V. *Cancers* (Basel) 2017, 9.
9. June, C. H., et al. *Science* 2018, 359, 1361-1365.
10. Fraietta, J. A., et al. *Nature* 2018, 558, 307-312.
11. Fraietta, J. A., et al. *Nat Med* 2018, 24, 563-571.
12. Fry, T. J., et al. *Nat Med* 2018, 24, 20-28.
13. Carpenter, R. O., et al. *Clin Cancer Res* 2013, 19, 2048-2060.
14. Cohen, A. D., et al. *J Clin Invest* 2019, 130.
15. Anurathapan, U., et al. *Cytotherapy* 2014, 16, 713-733.
16. Beatty, G. L., et al. *Oncoimmunology* 2014, 3, e970027.
17. Chen, N., et al. *Oncoimmunology* 2017, 6, e1273302.
18. Gilham, D. E., et al. *Trends Mol Med* 2012, 18, 377-384.
19. Durbin, H., et al. *Int J Cancer* Suppl 1988, 2, 50-58.
20. Tucker, D. F., et al. *Br J Cancer* 1985, 51, 631-639.
21. Epenetos, A. A., et al. *Br J Cancer* 1985, 51, 641-644.
22. Epenetos, A. A., et al. *Lancet* 1985, 2, 350-353.
23. Orsaria, M., et al. *Cancer Biomark* 2016, 17, 479-486.
24. Vergote, I. B., et al. *Tumour Biol* 1992, 13, 168-174.
25. Harmenberg, U., et al. *Tumour Biol* 1991, 12, 237-248.
26. Sandfeld-Paulsen, B., et al. *Mol Oncol* 2016, 10, 1595-1602.
27. Kalyan, A., et al. *J Gastrointest Oncol* 2018, 9, 160-169.
28. Bacac, M., et al. *Clin Cancer Res* 2016, 22, 3286-3297.
29. Hsia, L. T., et al. *Proc Natl Acad Sci USA* 2016, 113, E2162-2171.
30. Berahovich, R., et al. *Cancers* (Basel) 2018, 10.
31. Golubovskaya, V., et al. *Cancers* (Basel) 2017, 9.
32. Almagro, J. C., et al. *Front Biosci* 2008, 13, 1619-1633.
33. Gilliland, G. L., et al. *Methods Mol Biol* 2012, 841, 321-349.
34. Berahovich, R., et al. *Front Biosci* (Landmark Ed) 2017, 22, 1644-1654.
35. Rozman, P., et al. *Cytokine Growth Factor Rev* 2018, 41, 40-53.
36. Waks, A. G., et al. *Pathol Res Pract* 2019, 215, 251-255.
38. Kosmas, C., et al. *Oncology* 1998, 55, 435-446.
39. Muensch, H. A., et al. *Cancer* 1986, 58, 1689-1694.
40. Dunn, E. F., et al. *Oncogene* 2011, 30, 561-574.

---

What is claimed is:

1. A chimeric antigen receptor (CAR) comprising from N-terminus to C-terminus:
   (i) a single-chain variable fragment (scFv) comprising VH and VL, wherein scFv binds to PLAP (placental alkaline phosphatase), VH has the amino acid sequence of SEQ ID NO: 21, and VL has the amino acid sequence of SEQ ID NO: 22,
   (ii) a transmembrane domain,
   (iii) a co-stimulatory domain of CD28, OX-40, GITR, or 4-1BB, and
   (iv) an activating domain.

2. The CAR of claim 1, wherein the scFv comprises SEQ ID NO: 23.

3. The CAR of claim 1, wherein the activating domain is CD3 zeta.

4. The CAR of claim 1, wherein the co-stimulatory domain is CD28.

5. The CAR of claim 1, having the amino acid sequence of SEQ ID NO: 20.

6. A nucleic acid sequence encoding the CAR of claim 1.

7. An antibody or antigen-binding fragment thereof comprising VL having the amino acid sequence of SEQ ID NO: 22, and VH having the amino acid sequence of SEQ ID NO: 21.

* * * * *